(12) United States Patent
Lee et al.

(10) Patent No.: US 10,041,113 B2
(45) Date of Patent: Aug. 7, 2018

(54) APPARATUS, SYSTEM, AND METHOD USING IMMISCIBLE-FLUID-DISCRETE-VOLUMES

(71) Applicant: APPLIED BIOSYSTEMS, LLC, Carlsbad, CA (US)

(72) Inventors: Linda G. Lee, Palo Alto, CA (US); Sam L. Woo, Redwood City, CA (US); Congcong Ma, Foster City, CA (US); Richard T. Reel, Hayward, CA (US); Mark F. Oldham, Emerald Hills, CA (US); David M. Cox, Foster City, CA (US); Benjamin G. Schroeder, San Mateo, CA (US); Jon M. Sorenson, Alameda, CA (US); Willy Wiyatno, Union City, CA (US)

(73) Assignee: Applied Biosystems, LLC, Carlsbad, CA (US)

(*) Notice: Subject to any disclaimer, the term of this patent is extended or adjusted under 35 U.S.C. 154(b) by 0 days.

(21) Appl. No.: 14/925,656

(22) Filed: Oct. 28, 2015

(65) Prior Publication Data

US 2016/0194697 A1  Jul. 7, 2016

Related U.S. Application Data

(60) Division of application No. 12/557,488, filed on Sep. 10, 2009, now Pat. No. 9,194,772, which is a continuation of application No. 11/507,735, filed on Aug. 22, 2006, now abandoned.

(60) Provisional application No. 60/818,197, filed on Jun. 30, 2006, provisional application No. 60/731,133, filed on Oct. 28, 2005, provisional application No. 60/710,167, filed on Aug. 22, 2005.

(51) Int. Cl.
| | | |
|---|---|---|
| *C12Q 1/68* | (2018.01) | |
| *C12P 19/34* | (2006.01) | |
| *C12Q 1/6869* | (2018.01) | |
| *B01L 3/00* | (2006.01) | |
| *F15C 5/00* | (2006.01) | |
| *F16K 99/00* | (2006.01) | |
| *G01N 35/08* | (2006.01) | |
| *G01N 1/14* | (2006.01) | |
| *C12Q 1/6806* | (2018.01) | |
| *C12Q 1/6874* | (2018.01) | |
| *G01N 27/447* | (2006.01) | |
| *B01L 3/02* | (2006.01) | |
| *B01L 7/00* | (2006.01) | |

(52) U.S. Cl.
CPC ...... *C12Q 1/6869* (2013.01); *B01L 3/502715* (2013.01); *B01L 3/502784* (2013.01); *C12Q 1/6806* (2013.01); *C12Q 1/6874* (2013.01); *F15C 5/00* (2013.01); *F16K 99/0001* (2013.01); *F16K 99/0011* (2013.01); *F16K 99/0013* (2013.01); *G01N 1/14* (2013.01); *G01N 27/44743* (2013.01); *G01N 27/44769* (2013.01); *G01N 35/08* (2013.01); *B01J 2219/0036* (2013.01); *B01J 2219/0061* (2013.01); *B01J 2219/00353* (2013.01); *B01J 2219/00364* (2013.01); *B01J 2219/00608* (2013.01); *B01J 2219/00612* (2013.01); *B01J 2219/00619* (2013.01); *B01J 2219/00626* (2013.01); *B01J 2219/00637* (2013.01); *B01J 2219/00653* (2013.01); *B01J 2219/00657* (2013.01); *B01J 2219/00659* (2013.01); *B01L 3/0293* (2013.01); *B01L 7/52* (2013.01); *B01L 2200/0673* (2013.01); *B01L 2200/10* (2013.01); *B01L 2300/0864* (2013.01); *B01L 2300/0867* (2013.01); *B01L 2400/0421* (2013.01); *B01L 2400/0487* (2013.01); *F16K 2099/0084* (2013.01); *Y10T 137/0318* (2015.04); *Y10T 137/4259* (2015.04); *Y10T 137/85978* (2015.04); *Y10T 137/85986* (2015.04); *Y10T 137/86863* (2015.04); *Y10T 436/2575* (2015.01)

(58) Field of Classification Search
CPC ............ C12Q 1/6869; C12Q 2535/101; C12Q 1/6806; C12Q 1/6874; B01J 2219/00353; B01J 2219/0036; B01J 2219/00364; B01J 2219/00608; B01J 2219/0061; B01J 2219/00612; B01J 2219/00619; B01J 2219/00626; B01J 2219/00
USPC .......................................... 435/91.2, 6.1, 61
See application file for complete search history.

(56) References Cited

U.S. PATENT DOCUMENTS

| | | |
|---|---|---|
| 3,640,822 A | 2/1972 | Hrdina |
| 3,743,103 A | 7/1973 | Isreeli |
| 3,960,020 A | 6/1976 | Gordon et al. |
| 4,253,846 A | 3/1981 | Smythe et al. |

(Continued)

FOREIGN PATENT DOCUMENTS

| | | |
|---|---|---|
| WO | 2004/002627 | 1/2004 |
| WO | 2005/073410 | 8/2005 |

OTHER PUBLICATIONS

Anderson et al., Nucleic Acids Research, vol. 28, No. 12, pp. 1-6, 2000.*

(Continued)

*Primary Examiner* — Cynthia B Wilder

(57) ABSTRACT

Various embodiments of the teachings relate to a system or method for sample preparation or analysis in biochemical or molecular biology procedures. The sample preparation can involve small volume processed in discrete portions or segments or slugs, herein referred to as discrete volumes. A molecular biology procedure can be nucleic acid analysis. Nucleic acid analysis can be an integrated DNA amplification/DNA sequencing procedure.

18 Claims, 50 Drawing Sheets

(56) References Cited

U.S. PATENT DOCUMENTS

| | | | |
|---|---|---|---|
| 4,271,123 | A | 6/1981 | Curry et al. |
| 4,528,158 | A | 7/1985 | Gilles et al. |
| 4,574,850 | A | 3/1986 | Davis et al. |
| 4,610,170 | A | 9/1986 | Ekholm et al. |
| 4,908,112 | A | 3/1990 | Pace |
| 5,092,972 | A | 3/1992 | Ghowsi |
| 5,134,079 | A | 7/1992 | Cusack |
| 5,149,658 | A | 9/1992 | Cassaday |
| 5,739,036 | A | 4/1998 | Parris |
| 5,843,767 | A | 12/1998 | Beattie et al. |
| 5,848,107 | A | 12/1998 | Philips |
| 5,884,649 | A | 3/1999 | Proudman |
| 5,942,443 | A | 8/1999 | Parce et al. |
| 5,961,800 | A | 10/1999 | McBride et al. |
| 6,143,496 | A | 11/2000 | Brown et al. |
| 6,258,324 | B1 | 7/2001 | Yiu |
| 6,432,814 | B1 | 8/2002 | Steiner et al. |
| 6,485,905 | B2 | 11/2002 | Hefti |
| 6,508,273 | B1 | 1/2003 | Van Den Berg |
| 6,626,416 | B2 | 9/2003 | Sharma et al. |
| 6,638,760 | B1* | 10/2003 | Chen ................. C12Q 1/6834 435/287.1 |
| 6,719,535 | B2 | 4/2004 | Rakestraw et al. |
| 6,895,964 | B2 | 5/2005 | McAuliffe et al. |
| 6,908,770 | B1 | 6/2005 | McDevitt et al. |
| 7,041,481 | B2 | 5/2006 | Anderson |
| 7,955,864 | B2 | 6/2011 | Cox et al. |
| 2001/0049148 | A1 | 12/2001 | Wolk et al. |
| 2002/0159919 | A1 | 10/2002 | Churchill |
| 2003/0006140 | A1 | 1/2003 | Vacca et al. |
| 2003/0013200 | A1 | 1/2003 | Pai et al. |
| 2003/0145894 | A1 | 8/2003 | Burns |
| 2003/0162213 | A1 | 8/2003 | Fuller et al. |
| 2003/0194709 | A1 | 10/2003 | Yang |
| 2003/0199081 | A1* | 10/2003 | Wilding ................. B01D 61/18 435/287.2 |
| 2003/0213905 | A1 | 11/2003 | Lennon et al. |
| 2004/0014239 | A1 | 1/2004 | Wolk et al. |
| 2004/0058450 | A1 | 3/2004 | Pamula et al. |
| 2004/0180346 | A1 | 9/2004 | Anderson et al. |
| 2004/0185484 | A1 | 9/2004 | Costa et al. |
| 2004/0188254 | A1 | 9/2004 | Spaid |
| 2004/0194562 | A1 | 10/2004 | Brockman et al. |
| 2004/0234966 | A1 | 11/2004 | Bryning et al. |
| 2004/0241721 | A1 | 12/2004 | Gjerde et al. |
| 2004/0248144 | A1 | 12/2004 | Mir |
| 2005/0130173 | A1 | 6/2005 | Leamon et al. |
| 2005/0172476 | A1 | 8/2005 | Stone et al. |
| 2005/0223822 | A1 | 10/2005 | Ozbal |
| 2005/0227264 | A1* | 10/2005 | Nobile ................. B01F 3/0807 435/6.16 |
| 2006/0003439 | A1 | 1/2006 | Ismagilov |
| 2006/0037657 | A1 | 2/2006 | Shibata et al. |
| 2006/0056904 | A1 | 3/2006 | Haselton et al. |
| 2006/0163385 | A1 | 7/2006 | Link et al. |
| 2007/0039866 | A1 | 2/2007 | Schroeder et al. |
| 2007/0054266 | A1 | 3/2007 | Sato et al. |
| 2007/0068573 | A1 | 3/2007 | Cox |
| 2007/0122314 | A1 | 5/2007 | Strand et al. |
| 2007/0141593 | A1 | 6/2007 | Lee |
| 2007/0195127 | A1 | 8/2007 | Ahn |
| 2008/0023330 | A1 | 1/2008 | Viovy et al. |
| 2010/0209916 | A1 | 8/2010 | Zon |
| 2011/0171748 | A1 | 7/2011 | Cox et al. |

OTHER PUBLICATIONS

Curcio et al. Analytical Chemistry, vol. 75, No. 1, pp. 1-7, WEB publication date: Nov. 28, 2003.*
Hashimoto et al., Nucleic Acid Research, vol. 31, No. 8 e41, pp. 1-17, 2003.*
Obeid et al., Critical Reviews in Clinical Laboratory Sciences, 41 (5-6), pp. 429-465, Jan. 2004.*
Miller et al. Promega Notes Magazine No. 60, p. 02 (pp. 1-4 Standard page size), 1996.*
Dittrich et al., Anal. Bioanal. Chem 382: 1771-1782, (Year: Jun. 2005).*
Song et al., Angrew. Chem. Int. Ed. 43: 7, 768-772 (Year: 2003).*
Nia and Zare, Annu. Rev. Biomol. Strutt. 26: 567-596, (Year: 1997).*
Extended European Search Report dated Nov. 3, 2010 for European Application No. 06802016.3.
Ajdari, A. "DropLet ControL for Microfluidics", *Science*, vol. 309, www.sciencemag.org, Aug. 2005, 887-888.
Auroux, Pierre-Alain et al., "Miniaturised nucleic acid analysis", *Lab on a Chip, Royal Society of Chemistry, Cambridge*, vol. 4, 2004, 534-546.
Burns, et al., "Microfabricated Structures for Integrated DNA Analysis", *Proc. Natl. Acad. Sci.*, vol. 93, May 1996, 5556-5561.
Chiou, J. et al., "A Closed-Cycle Capillary Polymerase Chain Reaction Machine", *Analytical Chemistry, American Chemical Society*, vol. 73, No. 9, 2001, 2018-2021.
Curcio, Mario et al., "Continuous segmented-Flow Polymerase Chain Reaction for High-Throughput Miniaturized DNA Amplification", *Anal. Chem*, vol. 75(1), American Chemical Society, 2003, 1-7.
Hashimoto, et al., "On-line integration of PCR and cycle sequencing in capillaries: from human genomic DNA directly to called bases", *Nucleic Acids Research*; vol. 31, No. 8, 2003, 1-17.
Obeid, P.J. et al., "Microfabricated systems for nucleic acid analysis", *Critical Reviews in Clinical Laboratory Sciences, CRC Press*, Boca Raton, FL, vol. 41 , No. 5-6, Jan. 1, 2004, 429-465.
International Search Report dated Jan. 17, 2008 for International Application No. PCT/US06/32640.
Written Opinion of International Searching Authority dated Jan. 17, 2008 from International Application No. PCT/US06/32640.
Schneegass, et al., "Miniaturized flow-through PCR with different template types in a silicon chip thermocycler", *Lab on a Chip*; vol. (1), 2001, 42-49.
Thorsen, et al., "Dynamic Pattern Formation in a Vesicle-Generating Microfiuidic Device", *Physical Review Letters*, vol. 86, No. 18, Apr. 30, 2001, 4163-4166.
Waters, L.C. et al., "Microchip Device for Cell Lysis, Multiplex PCR Amplification, and Electrophoretic Sizing", *Analytical Chemistry*, vol. 70, No. 1, American Chemical Society, Columbus, US, 1998, 158-162.

\* cited by examiner

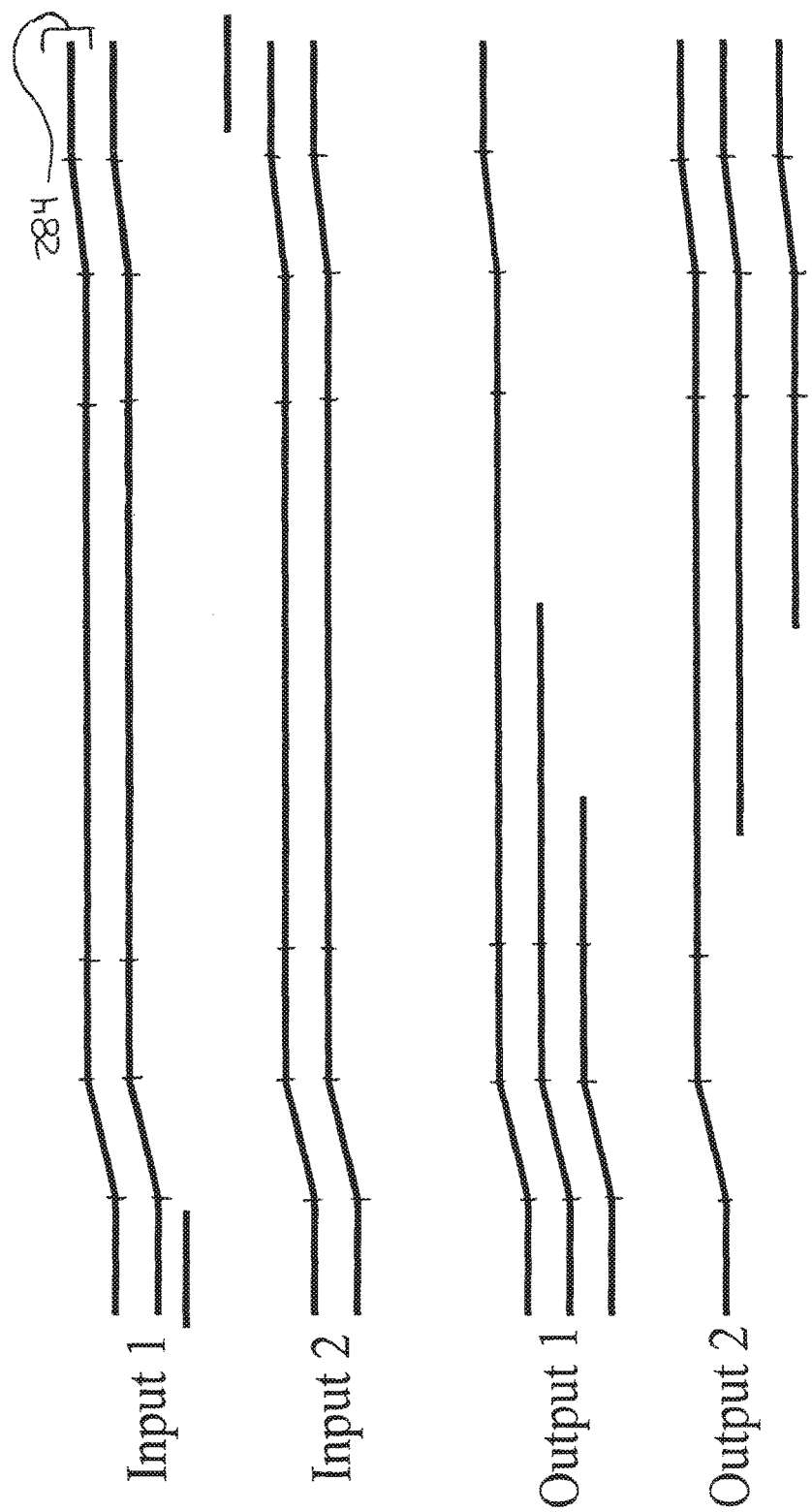

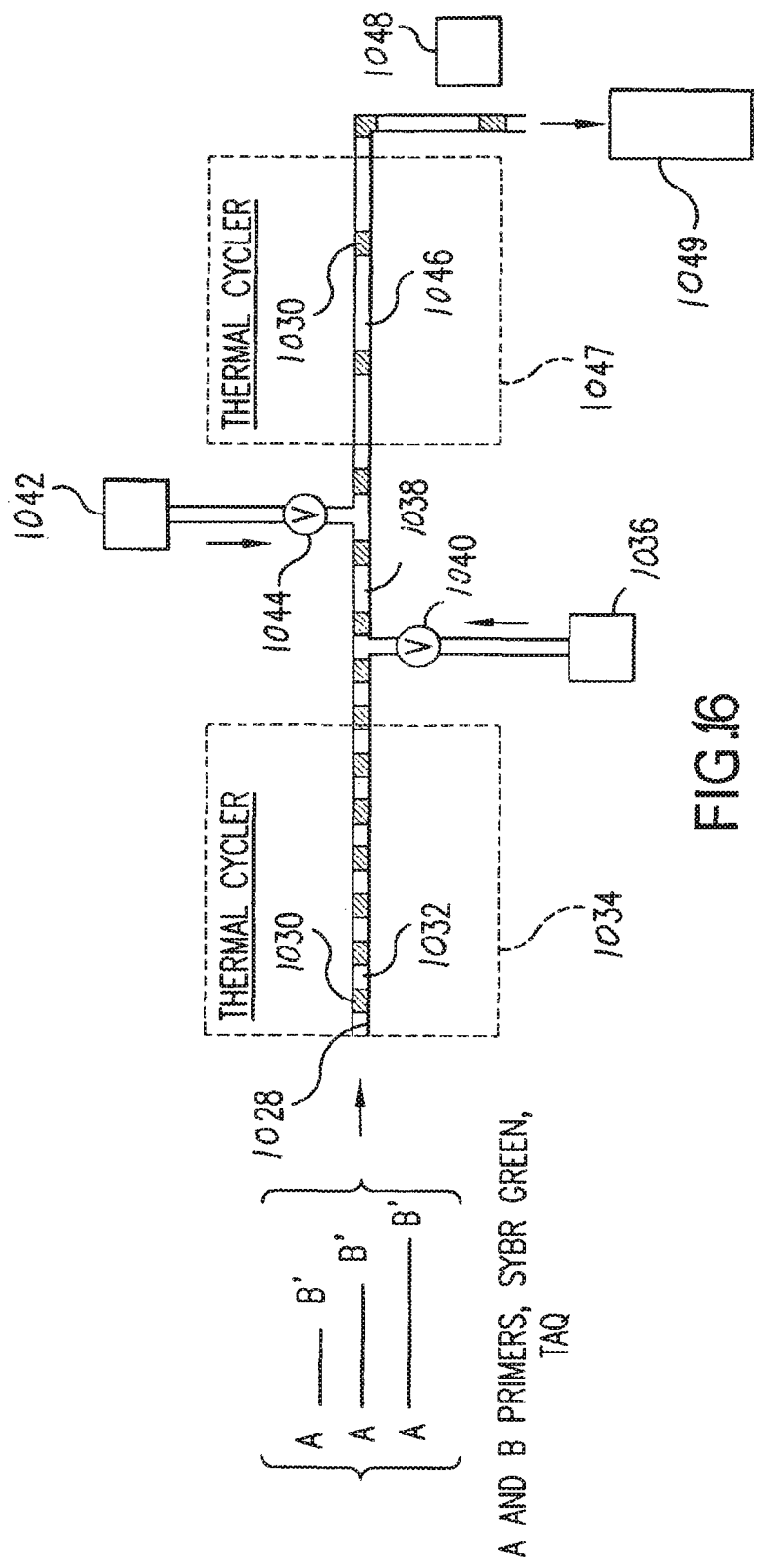

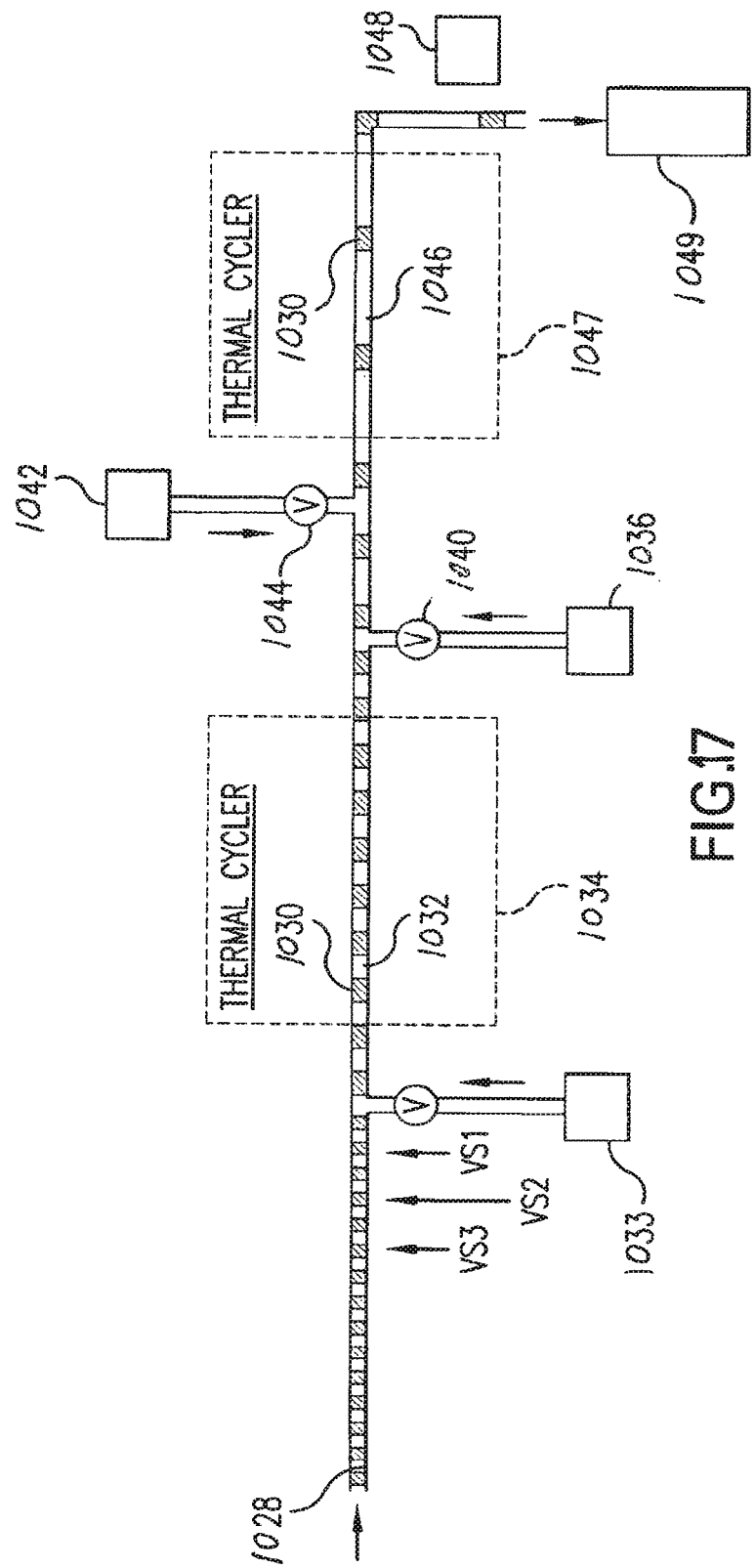

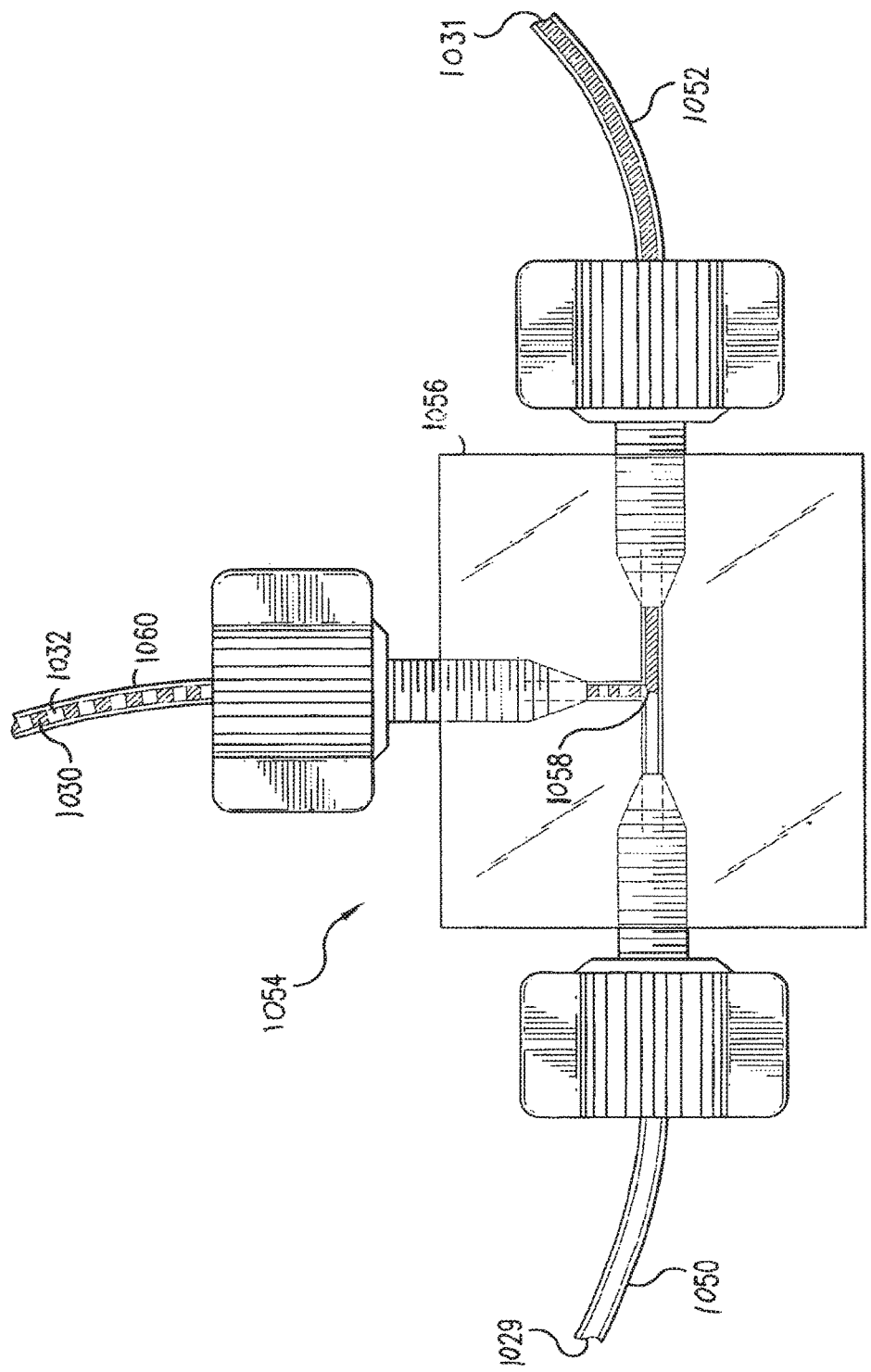

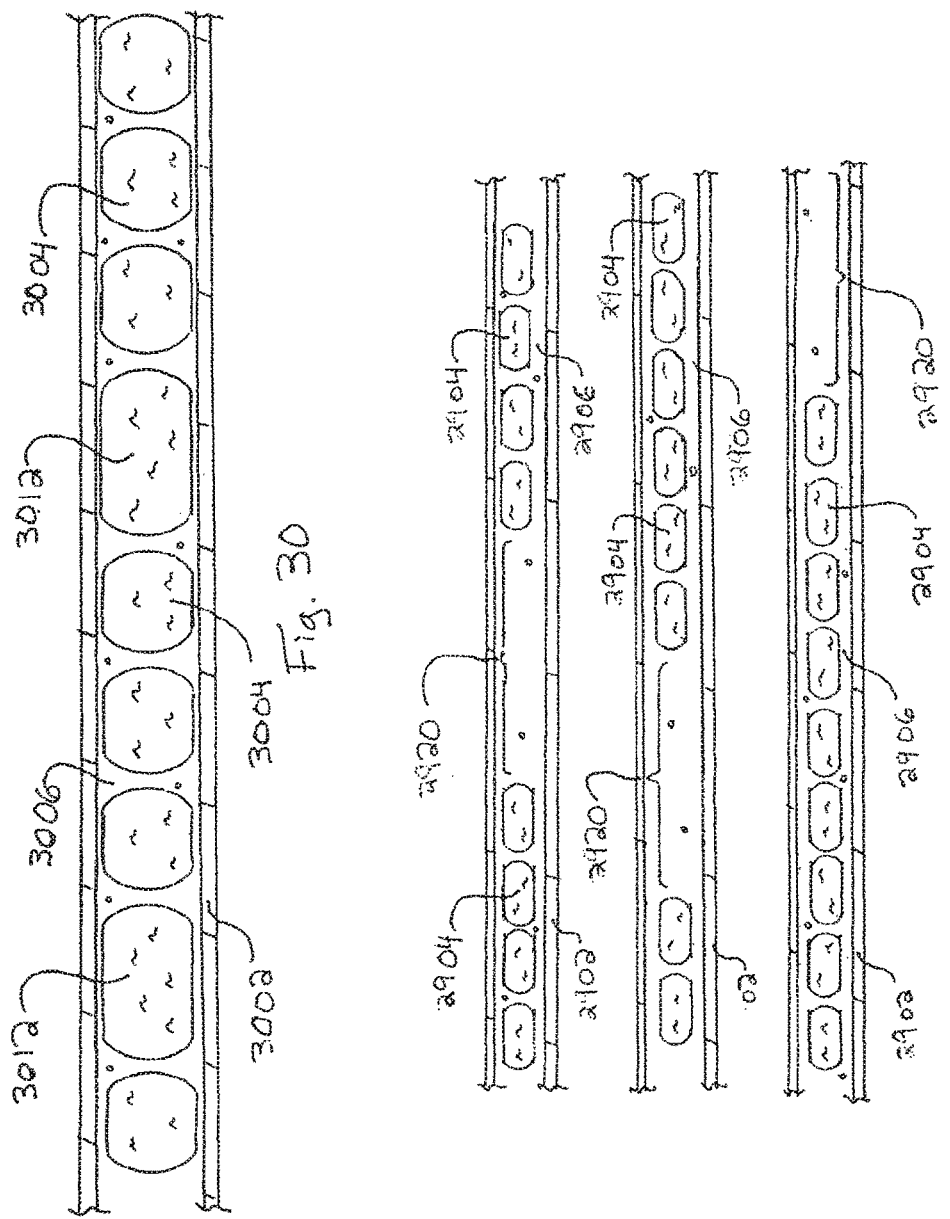

APPARATUS, SYSTEM, AND METHOD USING IMMISCIBLE-FLUID-DISCRETE-VOLUMES

CROSS-REFERENCE TO RELATED APPLICATIONS

The present application is a Divisional of U.S. patent application Ser. No. 12/557,488, filed Sep. 10, 2009, which is a Continuation of U.S. patent application Ser. No. 11/507,735, filed on Aug. 22, 2006, which claims the benefit of earlier filed U.S. Provisional Patent Application No. 60/710,167, filed Aug. 22, 2005, U.S. Provisional Patent Application No. 60/731,133, filed Oct. 28, 2005, and U.S. Provisional Patent Application No. 60/818,197, filed Jun. 30, 2006, which are incorporated herein in their entireties by reference.

INTRODUCTION

The section headings used herein are solely for organization purposes and are not to be construed as limiting the subject matter described in any way.

Various embodiments of the present teachings relate to a system or method for sample preparation for biochemical or molecular biology procedures involving micro sample volumes. A molecular biology procedure can comprise a nucleic acid analysis. A nucleic acid analysis can be an integrated DNA amplification/DNA sequencing method or a system for performing the methods.

SUMMARY

Various embodiments of the present teachings relate to systems, apparatus, and/or methods for sample processing that can be used for biochemical or molecular biology procedures involving different volumes, for example, small volumes such as micro-liter sized volumes or smaller.

According to the present teachings, the system can comprise an apparatus for processing discrete volumes of at least a first fluid in contact with a second fluid, wherein the first and second fluids are immiscible with each other, for example, discrete volumes of an aqueous liquid (herein "aqueous immiscible-fluid-discrete-volumes"), spaced-apart from one another by a spacing fluid that is immiscible with the immiscible-fluid-discrete-volumes. An immiscible-fluid-discrete-volume can be a partitioned segment in which molecular biology procedures can be performed. As used herein, an immiscible-fluid-discrete-volume can be one of many structures, three of which are: a fluid segment, a slug, and an emulsified droplet. In some embodiments, immiscible-fluid-discrete-conduits are formed and/or processed in a conduit.

This paragraph defines a conduit as it is used herein. A conduit can be any device in which an immiscible-fluid-discrete-volume can be generated, conveyed, and/or flowed. For example, a conduit as defined herein can comprise any of a duct, a tube, a pipe, a channel, an open top channel, a closed channel, a capillary, a hole or another passageway in a solid structure, or a combination of two or more of these, as long as the spaces defined by the respective solid structures are in fluid communication with one another. A conduit can comprise two or more tubes or other passageways connected together, or an entire system of different passageways connected together. An exemplary conduit can comprise an immiscible-fluid-discrete-volume-forming tube, thermal spirals, valve passageways, a processing conduit, junctions, and the like components all connected together to form one or more fluid communications therethrough, which system is also referred to herein as a main processing conduit. Examples of solid structures with holes or passageways therein that can function as conduits are manifolds, T-junctions, Y-junctions, rotary valves, and other valves. Thus, when connected to conduits, such structures can be considered part of a conduit as defined herein.

This paragraph defines a fluid segment, as it is used herein. A fluid segment is a discrete volume that has significant contact with the conduit wall(s), such that a cross-sectional area of the fluid segment is the same size and shape as a cross-sectional area of the conduit it contacts. At least a portion of a fluid segment fully fills the cross-sectional area of the conduit, such that the immiscible fluid adjacent it in the conduit can not flow past the fluid segment. The entire longitudinal length of the fluid segment does not necessarily contact the conduit or channel walls.

This paragraph defines a slug as used herein. A slug is a discrete volume that has at least a portion, which has approximately the same cross-sectional shape as the conduit in which it exists, but a smaller size. The smaller size is due to the insignificant contact, if any, of the slug with the conduit wall(s). A slug can have a cross-sectional dimension between approximately 0.5 and approximately 1.0 times the maximum dimension of a cross sectional area of the conduit. If the conduit has a circular cross section, the cross-sectional area of a slug can be concentric with the conduit's cross-sectional area, but it does not have to be, such as, for example, when the conduit is horizontal and, due to different specific gravities, one fluid rises toward the top of the cross-sectional area of the conduit under the influence of gravity. A slug can be free of contact with the conduit walls. A slug can have "feet" that appear as nibs or bumps along an otherwise smoothly appearing round surface. It is theorized that the "feet" at the bottom of the slug have contact with the conduit wall. In contrast to a fluid segment, the contact a slug can have with the conduit wall(s) still permits the immiscible fluid adjacent it in the conduit to flow past the slug.

The "slugs" processed by the teachings herein, separated by spacing fluid, can merge together to form larger slugs of liquid, if contacted together. The ability of the slugs, for example, aqueous slugs, described and taught herein, to merge together with each other, facilitates the downstream addition of aqueous reagents to the slugs.

This paragraph defines an emulsified droplet, as used herein. An emulsified droplet is a discrete volume that has no contact with the walls of the conduit. The size of an emulsified droplet is not necessarily constrained by the conduit, and examples of emulsified droplets described in the prior art range in size from about 1 femtoliter to about 1 nanoliter. The shape of an emulsified droplet is not constrained by the conduit, and due to the difference in surface-energies between it and the continuous phase liquid in which it is dispersed, it is generally spherical. It can have a maximum dimension that is not equal to, nor approximately equal to, but much less than the maximum dimension of the cross-sectional area of the conduit, for example, 20%, 10%, 5% or less. An emulsified droplet will not merge upon contact with another emulsified droplet to form a single, larger discrete volume, without external control. Put another way, an emulsified droplet is a stable discontinuous phase in a continuous phase.

A conduit can contain more than one emulsified droplet, but not more than one slug or fluid segment, at any cross-sectional location. Thus, a first emulsified droplet does not necessarily impede the movement of a second emulsified droplet past it, where as a fluid segment and a slug necessarily do not permit the passage of another fluid segment or slug past them, respectively. If two fluid segments are separated by a fluid with which the first and second of the two fluids is each immiscible, then the immiscible fluid also forms a discrete volume. It is likely that it has significant contact with the conduit walls and thus is another fluid segment.

Whether two immiscible fluids, when present in a conduit, form fluid segments of the first and second of the two immiscible fluids, slugs of the first immiscible fluid, or emulsified droplets of the first immiscible fluid, depends on at least the method of introduction of each fluid into the conduit, the relative surface energies of the first immiscible fluid, the second immiscible fluid, the conduit material, the contact angle each fluid forms with the other fluid and the conduit material, and the volume of the discrete volume of the first immiscible fluid. Thus, it is recognized that these definitions are merely reference points on a continuum, the continuum of the shape and size of discrete volumes of a first immiscible fluid in a conduit, and discrete volumes will exist that, when described, fall between these definitions.

Large scale sequencing projects can involve cloning DNA fragments in bacteria, picking and amplifying those fragments, and performing individual sequencing reactions on each clone. Standard sequencing reactions can be performed in 5 μl to 20 μl reaction volumes, even though only a small fraction of the sequencing product can be analyzed in a capillary when using electro-kinetic injection. Such cloning and standard sequencing protocols can be time consuming and use relatively large sample and reagent volumes. The relatively large volumes can be wasteful in terms of expensive consumable reagents.

An alternative to standard approaches can use smaller volumes, for example, 0.25 μl sample reaction volumes generated in aqueous immiscible-fluid-discrete-volumes, in partitioned sample portions, or other small volumes. It is possible to generate the aqueous immiscible-fluid-discrete-volumes separated by oil or other non-aqueous fluids in conduits. Using the methods and/or systems provided in this application, one can perform, for example, polymerase chain reaction (PCR) amplification of single DNA molecules to obtain, for example, amplicons. The amplified DNA or amplicons can then be used in sequencing reaction and then be sequenced in small volumes. Other manipulations of nucleic acids or proteins can also be accomplished, for example, DNA hybridization reactions or antibody-antigen binding assays.

According to various embodiments, a method is provided that comprises: amplifying a nucleic acid in at least one conduit to form an amplicon, the at least one conduit comprising an inner wall; attaching the amplicon to the inner wall to form an attached amplicon; and detecting the attached amplicon or an attached derivative thereof, in the at least one conduit. Detecting can comprise detecting a label or dye directly attached to a molecule of interest or detecting free label or dye resulting from incorporation of a molecule of interest into the amplified nucleic acid.

According to various embodiments, a method is provided that comprises contacting an aqueous sample fluid in a conduit with a non-aqueous spacing fluid that is immiscible with the aqueous sample, to form a plurality of discrete volumes of the aqueous sample fluid separated from one another by the non-aqueous spacing fluid, the aqueous sample fluid comprising a plurality of target nucleic acid sequences, wherein at least one of the discrete volumes comprises a first discrete volume that contains at least one target nucleic acid sequence. The method can comprise amplifying the at least one target nucleic acid sequence in the first discrete volume in the conduit to form an amplicon, and subjecting the amplicon to a nucleic acid sequencing reaction in the conduit.

According to various embodiments, a method is provided that comprises flowing a first fluid and a second fluid into a conduit, the first fluid and the second fluid being immiscible with respect to one another, wherein the first fluid contains a plurality of target molecules and the maximum cross-sectional dimension of the conduit is such that a plurality of immiscible-fluid-discrete-volumes of the first fluid are formed in the conduit and separated from one another by the second fluid. At least one of the immiscible-fluid-discrete-volumes of the first fluid can contain a single target molecule.

According to various embodiments, a system is provided that comprises at least one conduit comprising an inner surface and having a maximum cross-sectional inner dimension, an aqueous sample fluid introduction unit in fluid communication with the at least one conduit, and a spacing fluid introduction unit in fluid communication with the at least one conduit. The aqueous sample fluid introduction unit and the spacing fluid introduction unit can comprise separate units each in fluid communication with the at least one conduit. A control unit can be provided that is adapted to flow an aqueous sample fluid and a spacing fluid from the aqueous sample fluid introduction unit and the spacing fluid introduction unit, respectively. The control unit can be adapted to alternately introduce volumes of aqueous sample fluid and spacing fluid that together form discrete volumes of aqueous sample fluid in contact with spacing fluid, i.e., aqueous sample immiscible-fluid-discrete-volumes, in the at least one conduit wherein each aqueous sample immiscible-fluid-discrete-volume can comprise a maximum outer dimension that is equal to or slightly less than the maximum inner cross-sectional dimension.

The molecular biology procedures that can be performed in the various discrete volumes described herein, prior to out-processing as described herein, can, for example, utilize proteins or nucleic acids. Procedures with nucleic acids can comprise, for example, a PCR amplification and/or nucleic acid analysis of an amplification product. The PCR amplification and/or nucleic acid analysis of an amplification product can comprise an integrated DNA amplification/DNA sequencing method.

Using the apparatus, methods, and/or systems provided in this application, a polymerase chain reaction (PCR) amplification of single DNA molecules can be performed, for example, to obtain amplicons. The amplified DNA or amplicons can then be used in a sequencing reaction and then be sequenced in small volumes. Other manipulations of nucleic acids or proteins can also be accomplished, for example, DNA hybridization reactions or antibody-antigen binding assays.

The apparatus, system and/or methods described herein can also be used in conjunction with U.S. Provisional Patent Application No. 60/710,167 entitled "Sample Preparation for Sequencing" to Lee et al., filed Aug. 22, 2005, U.S. Provisional Patent Application No. 60/731,133 entitled "Method and System for Spot Loading a Sample" to Schroeder et al., filed Oct. 28, 2005, and systems described in U.S. Provisional Patent Application No. 60/818,197 filed Jun. 30, 2006, which are incorporated herein in their entireties by reference.

An exemplary type of sample preparation can be used for genotyping, gene-expression, methylation analysis, and/or directed medical sequencing (VariantSEQr™, for example, an Applied Biosystems, Foster City, Calif., product comprising primers for resequencing genes and detecting variations) that requires multiple liquids to be brought together in an aqueous discrete volume. For example, in a gene-expression application, each aqueous discrete volume can contain individual primer sets. The sample to be analyzed, for example, complementary DNA (cDNA), can be added to each aqueous discrete volume. In the VariantSEQr™ application, for example, an aqueous discrete volume can comprise a primer set, and genomic DNA can be added to that discrete volume.

Various embodiments of the present teachings relate to an apparatus, system, or method for sample preparation and/or sample deposition. The sample preparation can be used for biochemical or molecular biology procedures involving small volumes, for example, microliter-sized volumes or smaller.

Using the apparatus, methods, and/or systems provided in this application processes can be performed on the immiscible-fluid-discrete-volumes. These downstream processes can include, for example, electrophoretic separation, fluorescent detection, and the like. Other manipulations of nucleic acids or proteins can also be accomplished, for example, DNA hybridization reactions or antibody-antigen binding assays.

In some embodiments, flow rates for moving aqueous discrete volumes can comprise rates of from about 1 picoliter/sec. to about 200 microliters/sec., and can be selected based on the inner diameter of the conduits through which the liquids are to be pumped. Within that broad range, in some embodiments, the aqueous discrete volumes comprising 50% reagents, for example, PCR reagents, and 50% other reagents, for example, sample fluid, in contact with oil can flow at 0.5 microliter/sec, or in a range from about 0.1 microliter/sec. to 2 microliters/sec. In some embodiments, aqueous volumes comprising reagents, for example, exo SAP or sequencing mix, can flow at a rate of about ⅓ microliters/sec., or in a range from about 0.1 microliters/sec. to 1 microliters/sec. In some embodiments, when aspirating aqueous fluid into a conduit as discrete volumes, flow rates of up to about 0.1 microliters/sec. max can be used. In some embodiments, when outputting an aqueous discrete volume, a flow rate of about ⅓ to about ½ ul/sec can be used, or in a range from about 0.1 microliters/sec. to about 2 microliters/sec. can be used.

Tubing that can be used with the 1 picoliter/sec. to 200 microliter/sec. flow rate can comprise an inner diameter of from about 250 microns to about 1000 microns. In other embodiments, the inner diameter of the inner tube can be from about 10 microns to about 2000 microns, while the inner diameter of the outer tube can be from about 20 microns to about 5000 microns, for example, from about 35 microns to about 500 microns. Other diameters, however, can be used based on the characteristics of the slug processing system desired. In some embodiments, a tube having a 10 micron inner diameter is used with a flow rate of from about 8 to about 10 picoliters/second. In some embodiments, a tube having a 5000 micron inner diameter is used with a flow rate of from about 25 to about 200 microliters/second. In some embodiments, a tube having a 500 micron inner diameter is used with a flow rate of from about 0.25 to about 2.0 microliters/second.

The method comprises contacting an aqueous sample fluid liquid with a non-aqueous spacing fluid that is immiscible with the aqueous sample fluid to form a plurality of discrete volumes of the aqueous sample fluid in a conduit separated from one another by the non-aqueous spacing fluid. The aqueous sample fluid liquid can comprise a plurality of target nucleic acid sequences, wherein at least one of the discrete volumes comprises at least one target nucleic acid sequence. In some embodiments, at most about 40% of the plurality of the discrete volumes in the inner conduit can each comprise a single target nucleic acid sequence. In various other embodiments, less than about 37% of the plurality of discrete volumes in the conduit can each comprise a single target nucleic acid sequence. In other embodiments, at least 1% or more, 5% or more, 10% or more, or 20% or more can have a single target nucleic acid sequence, for example, upon formation of the discrete volumes.

According to various embodiments, each of the plurality of immiscible-fluid-discrete-volumes in the inner conduit can comprise one or more respective oligonucleotide primers. Oligonucleotide primers can be chosen as determined by one of skill in the art to accomplish the desired objective, for example, universal primers and/or zip code primers can be used.

In some embodiments, out-putting immiscible-fluid-discrete-volumes that have been subjected to upstream processing, can be integrated with the system. Such upstream processing can include thermal cycling to amplify the at least one target nucleic acid sequence in the first discrete volume in the conduit to form an amplicon, and thereafter subjecting the amplicon to a nucleic acid sequencing reaction. For such purposes, and in some embodiments, the discrete volumes or immiscible-fluid-discrete-volumes can comprise reaction components, for example, oligonucleotide primers. Various embodiments of processing can include universal PCR that can comprise up-front multiplexed PCR followed by decoding, for example, see WO 2004/051218 to Andersen et al., U.S. Pat. No. 6,605,451 to Marmaro et al., U.S. patent application Ser. No. 11/090,830 to Andersen et al., and U.S. patent application Ser. No. 11/090,468 to Lao et al., all of which are incorporated herein in their entireties by reference. Details of real time PCR can be found in Higuchi et al., U.S. Pat. No. 6,814,934 B1, which is incorporated herein by reference in its entirety.

According to various embodiments, once the steps of a desired protocol, for example, a PCR, PCR clean-up, and sequencing reaction protocol, have been completed, a sample can be removed or injected from a processing conduit, for example, using an electrical field applied across a conduit and extending into a charged analyte collection chamber or compartment, or by using another electrokinetic sample movement technique. The collected or extracted charged analytes removed from the sample can then be used for DNA sequencing or other procedures. The DNA sequencing can use capillary electrophoresis instruments, for example, a commercially available AB 3730xl DNA Analyzer (Applera Corporation, Foster City, Calif.), that can process samples in 96- or 384-well plate formats. In various embodiments, the sample can be removed, injected, or recovered from the processing conduit into one or more wells of a microtiter plate, for example, through a pathway that comprises a loading conduit or tube.

Further devices, systems, and methods that can be used with or otherwise implement the present teachings include those described, for example in concurrently filed U.S. Provisional Patent Application No. 60/818,197, entitled "Device and Method for Making Immiscible-Fluid-Discrete-Volumes," to Cox et al., concurrently filed U.S. patent application Ser. No. 11/508,756 entitled "Apparatus and Method for Microfluidic Control of a First Fluid in Contact with a Second Fluid wherein the First and Second Fluids are Immiscible," to Cox et al., and concurrently filed U.S. patent application Ser. No. 11/507,733, now U.S. Pat. No. 9,285,297, which are herein incorporated in their entireties by reference.

DRAWINGS

The skilled artisan will understand that the drawings described below, are for illustration purposes only. The drawings are not intended to limit the scope of the present teachings in any way. In the drawings:

FIGS. 2G-2H depict various cycles and the results thereof, of combined zip code resequencing reactions according to various embodiments;

FIG. 16 illustrates a scheme for an integrated sample preparation for de novo sequencing;

FIG. 17 illustrates a resequencing scheme;

FIG. 18 illustrates a "T" junction that can be used for sample preparation;

FIG. 29 is a cross-sectional view of three conduits each having therein one or more respective sets of slugs, and showing fiducial markers between the sets;

FIG. 30 is a cross-sectional view of a conduit having therein a plurality of sets of slugs and showing aqueous fiducial markers between the sets;

DESCRIPTION OF VARIOUS EMBODIMENTS

Figure 1A:
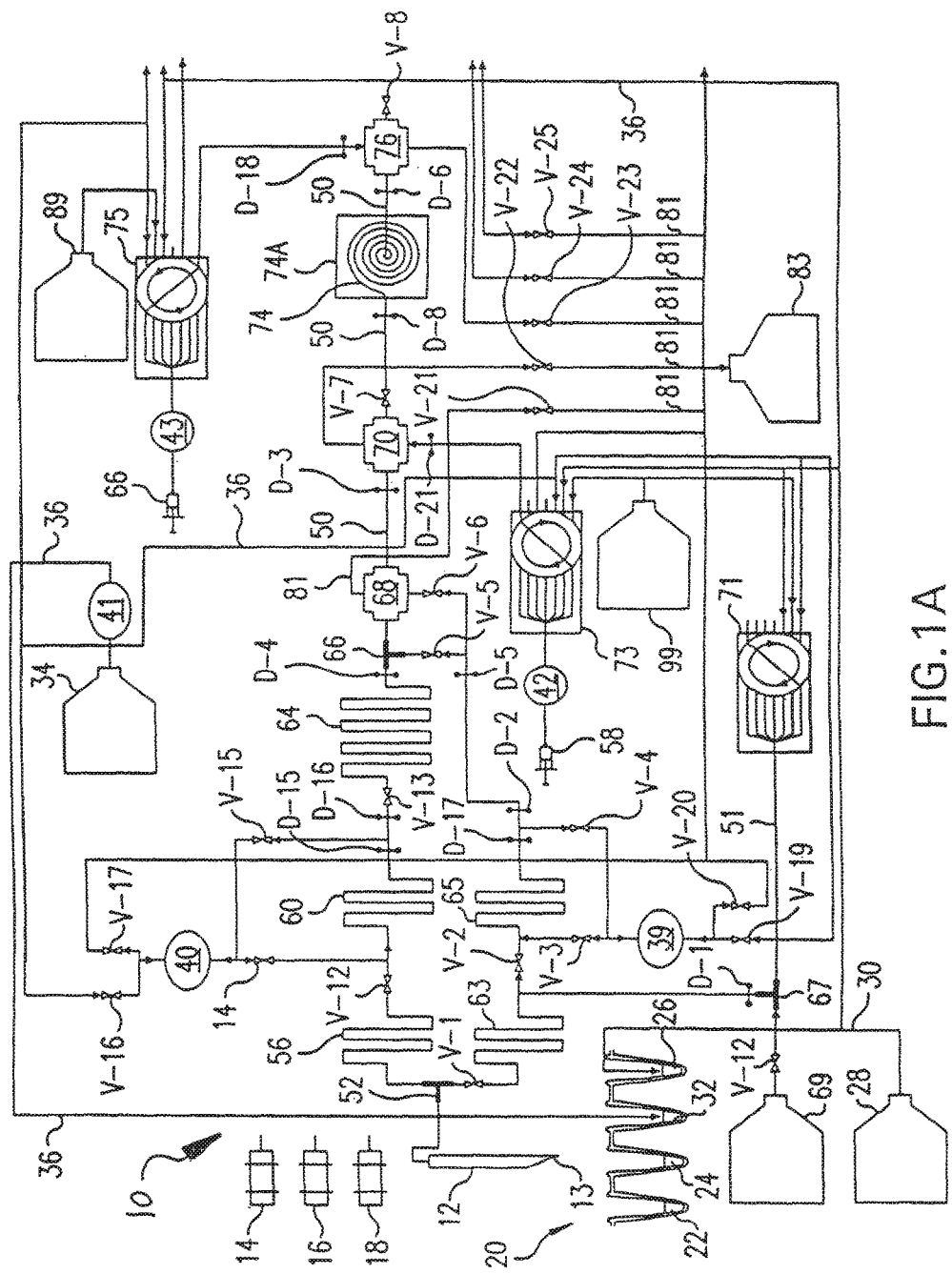
FIGS. 1A and 1B are the left-side and right-side, respectively, of a schematic diagram depicting a system according to various embodiments of the present teachings and configured to generate discrete volumes of a first fluid spaced apart from one another by a spacing fluid, to process the discrete volumes, and to output the discrete volumes.

It is to be understood that the following descriptions are exemplary and explanatory only. The accompanying drawings are incorporated in and constitute a part of this application and illustrate several exemplary embodiments with the description. Reference will now be made to various embodiments, examples of which are illustrated in the accompanying drawings. Wherever possible, the same reference numbers are used in the drawings and the description to refer to the same or like parts.

Throughout the application, descriptions of various embodiments use "comprising" language, however, it will be understood by one of skill in the art, that in some specific instances, an embodiment can alternatively be described using the language "consisting essentially of" or "consisting of."

For purposes of better understanding the present teachings and in no way limiting the scope of the teachings, it will be clear to one of skill in the art that the use of the singular includes the plural unless specifically stated otherwise. Therefore, the terms "a," "an" and "at least one" are used interchangeably in this application.

Unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. In some instances, "about" can be understood to mean a given value+5%. Therefore, for example, about 100 nl, could mean 95-105 nl. At the very least, each numerical parameter should at least be construed in light of the number of reported significant digits and by applying ordinary rounding techniques.

Reference to "nucleotide" can be understood to mean a phosphate ester of a nucleotide, as a monomer unit or within a nucleic acid. Nucleotides are sometimes denoted as "NTP", or "dNTP" and "ddNTP" to particularly point out the structural features of the ribose sugar. "Nucleotide 5'-triphosphate" can refer to a nucleotide with a triphosphate ester group at the 5' position. The triphosphate ester group may include sulfur substitutions for the various oxygens, for example, α-thio-nucleotide 5'-triphosphates. Nucleotides can comprise a moiety of substitutes, for example, see, U.S. Pat. No. 6,525,183 B2 to Vinayak et al., incorporated herein by reference.

The terms "polynucleotide" or "oligonucleotide" or "nucleic acid" can be used interchangeably and includes single-stranded or double-stranded polymers of nucleotide monomers, including 2'-deoxyribonucleotides (DNA) and ribonucleotides (RNA) linked by internucleotide phosphodiester bond linkages, or internucleotide analogs, and associated counter ions, for example, H+, NH4+, trialkylammonium, Mg2+, Na+ and the like. A polynucleotide may be composed entirely of deoxyribonucleotides, entirely of ribonucleotides, or chimeric mixtures thereof. Polynucleotides may be comprised of nucleobase and sugar analogs. Polynucleotides typically range in size from a few monomeric units, for example, 5-40 when they are frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted. A labeled polynucleotide can comprise modification at the 5'terminus, 3'terminus, a nucleobase, an internucleotide linkage, a sugar, amino, sulfide, hydroxyl, or carboxyl. See, for example, U.S. Pat. No. 6,316,610 B2 to Lee et al. which is incorporated herein by reference. Similarly, other modifications can be made at the indicated sites as deemed appropriate.

The term "reagent," should be understood to mean any reaction component that in any way affects how a desired reaction can proceed or be analyzed. The reagent can comprise a reactive or non-reactive component. It is not necessary for the reagent to participate in the reaction. The reagent can be a recoverable component comprising for example, a solvent and/or a catalyst. The reagent can comprise a promoter, accelerant, or retardant that is not necessary for a reaction but affects the reaction, for example, affects the rate of the reaction. A reagent can comprise, for example, one member of a binding pair, a buffer, or a DNA that hybridizes to another DNA. The term "reagent" is used synonymous with the term "reaction component." 2

Methods, apparatuses and systems described herein can use fluids immiscible in each other. Fluids can be said to be immiscible in each other when they can be maintained as separate fluid phases under conditions being used. Immiscible fluids can also be said to be incapable of mixing with each other or attaining a solution with each other. An aqueous liquid and a non-aqueous liquid such as oil can be said to be immiscible with each other. Throughout the specification, reference is made to aqueous slugs. This is merely exemplary and does not necessarily preclude the use or manufacture of non-aqueous liquid slugs in combination with an immiscible liquid.

While oil and aqueous liquids are immiscible in each other, such a combination does not necessarily form aqueous immiscible-fluid-discrete-volumes in the oil when the two liquids are mixed or placed together. For example, oil may form the disperse phase in a continuous aqueous liquid in a larger volume, as it does in certain salad dressing. For another example, oil and aqueous liquids may merely form aqueous droplets or microdroplets in a large volume of oil, but not necessarily aqueous immiscible-fluid-discrete-volumes. Aqueous immiscible-fluid-discrete-volumes can form, however, using an apparatus such as, for example, apparatus 100 as shown in U.S. Provisional Patent Application No. 60/818,197, entitled "Device and Method for Making Immiscible-Fluid-Discrete-Volumes," to Cox et al.

Aqueous solutions and oil from separate sources can be combined to form a continuous flowing liquid stream comprising aqueous immiscible-fluid-discrete-volumes separated from one another by the oil. Because the aqueous immiscible-fluid-discrete-volumes entirely or almost entirely fill the cross-sectional area of the conduit or tube in which they are formed, the resulting stream of aqueous immiscible-fluid-discrete-volumes in oil can exhibit a banded appearance. According to various embodiments, such a pattern can be exhibited by combining any two immiscible fluids with one another. The pattern can be formed throughout the length of the conduit. In various embodiments, a first aqueous immiscible-fluid-discrete-volume can contain different reagents than a second aqueous immiscible-fluid-discrete-volume. In other words, not all aqueous immiscible-fluid-discrete-volumes throughout the conduit need to contain the same reagents.

An aqueous immiscible-fluid-discrete-volume can be spaced apart from an adjacent aqueous immiscible-fluid-discrete-volume by the oil. In various embodiments, liquids other than oil can act as a spacing fluid, provided that the spacing fluid and aqueous fluid are immiscible with respect to each other and provided that they can form individual aqueous immiscible-fluid-discrete-volumes spaced apart from one another by the spacing fluid. In various embodiments, gas can be used as a spacing fluid.

According to various embodiments, methods are provided that refer to processes or actions involved in sample preparation and analysis. It will be understood that in various embodiments a method can be performed in the order of processes as presented, however, in related embodiments the order can be altered as deemed appropriate by one of skill in the art in order to accomplish a desired objective.

According to various embodiments, the methods, devices or systems described herein can be used to produce various consumable products. For example, the methods can produce nucleic acids of a single type that have been amplified from a single template and that are attached to a conduit for further use. Templates, for example, can comprise either generic or target specific zip code sequences or other sequences of interest that can be used for additional analysis. Conduits comprising sequences of interest can be closed off and shipped, and if desired can be used in systems adapted to accept such conduits. A system adapted to accept such conduits can comprise connectors or ferrules for connecting the conduit having sequences of interest to the system. Alternatively, the connector or ferrule can be attached to the conduit. In various embodiments, a conduit can comprise aqueous immiscible-fluid-discrete-volumes therein. Each aqueous immiscible-fluid-discrete-volume can comprise, for example, either the same or identical primer sets. In various embodiments, the aqueous immiscible-fluid-discrete-volumes can comprise different primers and probe sets. The conduit having sequences of interest can be frozen prior to shipping. Alternatively, sequences of interest can be detached from the conduits and used in other ways, as deemed appropriate by one of skill in the art.

Figure 1B:
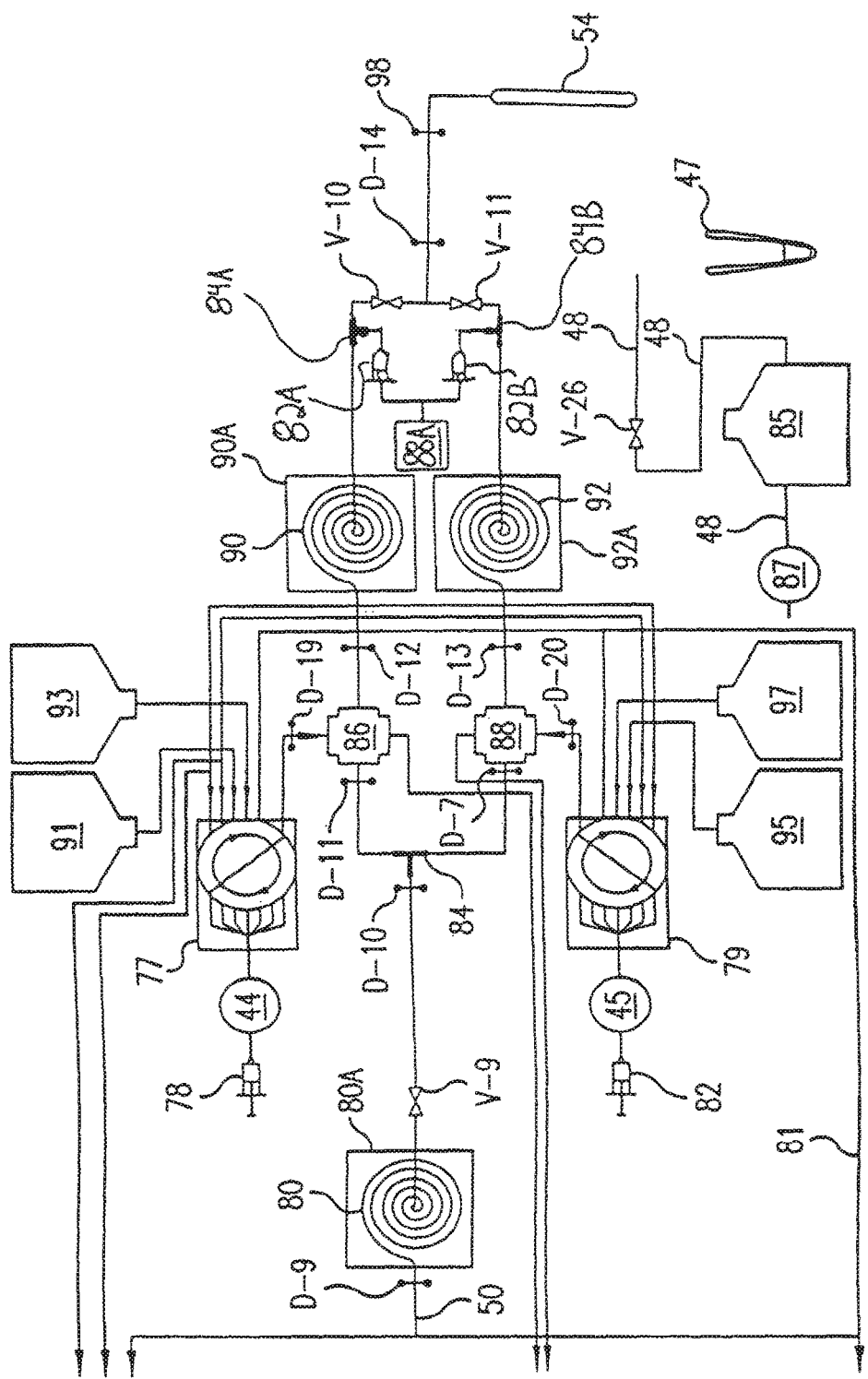

FIGS. 1A and 1B are the left-side and right-side, respectively, of a schematic diagram detailing an example of a fluid processing system 10 for processing immiscible-fluid-discrete-volumes. The six conduits on the right-hand side of FIG. 1A and terminating in arrow heads pointing to the right are respectively continued as the six conduits shown on the left-hand side of FIG. 1B and terminating in arrow heads pointing to the left, such that the top conduit of each respective six depicted are continuations of each other, and so on going down the figures. Generally, system 10 can be configured to perform different types of assays on fluids introduced thereinto. The amounts and types of fluids introduced into system 10 can be varied depending on a particular assay to be performed. Exemplary assays can include, for example, de novo nucleic acid sequencing reactions, and nucleic acid resequencing reactions, as discussed herein.

According to various embodiments, one or more samples 22, 24, can be introduced to system 10. Samples 22 and 24, for example, can comprise a nucleic acid containing fluid. According to some embodiments, the nucleic acid contained in a sample can be, for example, a single copy of a genomic DNA sequence of an organism, or complementary DNA from an organism.

In some embodiments a plurality of fluids can be introduced into fluid processing system 10 by way of an immiscible-fluid-discrete-volume-forming conduit 12. Suitable immiscible-fluid-discrete-volume-forming conduits include, for example, pipettes, capillaries, electro-wetting capillaries, needles, and any device configured to be in fluid communication with fluid processing system 10. Immiscible-fluid-discrete-volume-forming conduit 12 can be part of a system that can comprise, for example, a pump or another apparatus adapted to produce controlled intake of fluids through intake tip 13 into immiscible-fluid-discrete-volume-forming conduit 12. The immiscible-fluid-discrete-volume-forming conduit 12 can be adapted to control an introduction unit to inject a volumes of aqueous sample fluid and spacing fluid that respectively form aqueous sample fluid immiscible-fluid-discrete-volumes in the at least one conduit wherein each aqueous sample fluid immiscible-fluid-discrete-volume can comprise a maximum outer dimension that is equal to or slightly less than the maximum inner cross-sectional dimension of immiscible-fluid-discrete-volume-forming conduit 12. One of skill in the art will understand that the maximum inner cross-sectional dimension of a conduit is the inner diameter of the conduit if the conduit has a circular cross-section.

According to various embodiments, immiscible-fluid-discrete-volume-forming conduit 12 can comprise a tip 13. Tip 13 can interface with fluids to be drawn into system 10. Tip 13 can comprise an angled surface or have any suitable geometry such that the creation of air bubbles in immiscible-fluid-discrete-volume-forming conduit 12 is minimized or eliminated when tip 13 contacts and draws in a fluid. A detailed description of tip 13 can be found below in the description of FIG. 13. Immiscible-fluid-discrete-volume-forming conduit 12 can be robotically controlled, or manually controlled. Robotic configurations can comprise, for example, stepper motors 14, 16, and 18, which can move immiscible-fluid-discrete-volume-forming conduit 12 in X-axis, Y-axis, and Z-axis directions, respectively. In some embodiments, tube 12 can be moved in the Z-axis direction by a stepper motor 18, and a fluid container can be moved in the X-axis and Y-axis directions by stepper motors 14 and 16, respectively. In some embodiments, tube 12 can be stationary and a fluid container can be moved in the X-axis, Y-axis, and Z-axis directions by stepper motors 14, 16, and 19, respectively. Motive force providers other than stepper motors can be used.

According to various embodiments, a variety of fluids can be introduced into fluid processing system 10, in a number of different combinations, depending on the particular type of assay to be performed. The fluids can reside on any suitable fluid retaining device, for example, in the wells of a multi-well plate 20, an opto-electrowetting plate, a tube of preformed slugs, a tube of stable emulsified nanodroplets, individual tubes, strips of tubes, vials, flexible bags, or the like.

According to some embodiments, fluid processing system 10 can comprise a number of different fluid conduits and fluid control devices. The following description applies to the embodiment as illustrated in FIGS. 1A and 1B, but one skilled in the art will understand that alterations to fluid processing system 10 can be made while the teachings remain within the scope of the present teachings. As illustrated, fluid processing system 10 can comprise a main system conduit 50. Main conduit system 50 can comprise a plurality of conduits connecting together, for example, the following exemplary components: T-intersections 52, 66, and 84; holding conduits 56, 60, 63, 64 and 65; valves V-1, V-2, V-5, V-6, V-7, V-8, V-9, V-10, V-11, V-12, and V-13; cross-intersections 68, 70, 76, 86, and 88; and thermal-cyclers 74, 80, 90, and 92. Each thermal-cycler 74, 80, 90, and 92 can comprise a thermal spiral therein, as shown.

Main conduit system 50 can provide a fluid communication between T-intersection 52 and output conduit 54. From T-intersection 52, conduit system 50 comprises two pathways that intersect at cross-intersection 68. A first pathway can take a fluid sequentially through holding conduits 56, 60 and 64, and T-intersection 66, before reaching cross-intersection 68. A second pathway can take a fluid sequentially through holding conduits 50, and 65, and through either T-intersection 66, to cross-intersection 68, or directly to cross-intersection 68. Both the first pathway and the second pathways are configured to hold fluids for later analysis and are configured to interface with pumps for moving fluids along the conduits as discussed below.

From cross-intersection 70, fluids can move sequentially to thermal-cycler 74, cross-intersection 76, thermal-cycler 80, and T-intersection 84. At T-intersection 84 fluids can sequentially move either through cross-intersection 86, thermal-cycler 90, and output conduit 54, or through cross-intersection 88, thermal-cycler 92, and an output conduit.

According to some embodiments fluid processing system 10 can comprise pumps 39 and 40. Pump 40 can be configured to remove or add oil to main conduit system 50, and thereby move fluids located therein. Pump 39 can be configured to remove or add oil to main conduit system 50 to move fluids located therein. All of the pumps described herein can create positive and/or negative pressures in the various conduits of system 10.

According to various embodiments, a T-intersection can comprise any intersection having three discrete pathways extending from, for example, either a Y-intersection or a T-intersection. In various embodiments, the intersection can comprise a valve-less intersection where a stream of aqueous sample fluid and a stream of non-aqueous spacing fluid can merge together. For example, microfabrication technology and the application of electrokinetics can achieve fluid pumping in valve-less, electronically controlled systems. Components comprising shape-optimized channel turns, optimal injection methods, micromixers, and/or high flow rate electroosmotic pumps can be used in such a valve-less system.

According to some embodiments, system 10 can comprise detectors D-1, D-2, D-3, D-4, D-5, D-6, D-7, D-8, D-9, D-10, D-11, D-12, D-13, D-14, D-15, D-16, D-17, D-18, D-19, and D-20, and detector 98. The detectors can comprise, for example, fluorescent detectors, infrared detectors, refractive index detectors, capacitive detectors, absorption detectors, combinations thereof, and the like. The detectors can detect changes in the refractive index of different fluid volumes. In FIGS. 1A and 1B, all of the detectors depicted are infrared detectors with the exception of detector 98 which is a fluorescent signal detector, although other arrangements can be used. The infrared detectors can comprise refractive index detectors. The discrete volume detectors can be configured to distinguish immiscible fluid discrete volumes from spacing fluid or oil as the discrete volumes travel through the conduits of system 10.

According to various embodiments, the system can comprise a thermal-cycling device adapted to thermally cycle an aqueous sample fluid in a conduit disposed thereon or therein. The conduit can be coiled around the thermal-cycler to increase the amount of contact between the conduit and a surface of the thermal-cycler. The thermal-cycling device can comprise a heat source, for example, a radiant heat source, a non-radiant heat source, a peltier device, or the like, and a cooling source, for example, a fan, an air jet, or a liquid-circulating system in a thermal block. The thermal-cycling device can comprise one or more temperature sensors and one or more control units for controlling heating and cooling according to a desired or programmed thermal cycle.

The conduits of the present teachings can comprise capillary tubes having an inner diameter and the inner diameter can be, for example, about 1000 microns or less, for example, about 800 microns or less, or about 500 microns or less. In some embodiments, the conduit has a minimum inner dimension, or diameter, of from about 1.0 micron to about 100 microns, or from about 50 microns to about 75 microns. In other embodiments, the conduit can have an inner diameter greater than about 300 microns. In some embodiments, the conduit can comprise an inner diameter in the range of from about 0.015 inch to about 0.025 inch, for example, from about 0.019 inch to about 0.025 inch. In some embodiments, the conduit can have a smaller diameter at and/or beginning before a pair of thermal spirals near the downstream end of the system which are designed for forward/reverse sequencing amplification. Other details about the thermal-cycling device, capillary channel, and other system components will become apparent in view of the teachings herein.

System 10 can comprise a single molecule amplification fluid (SAMF) conduit system 51. SAMF conduit system 51 can comprise conduits connecting a SMAF reservoir 69 sequentially to valve V-18 and T-intersection 67. SAMF conduit system 51 can comprise conduits that connect T-intersection 67 to main conduit system 50 and a rotary valve 71. SAMF reservoir 69 can comprise SAMF. SAMF can be a diluted form of a master nucleic acid amplification fluid. SAMF can be designed to efficiently amplify low concentrations of nucleic acids.

Fluid processing system 10 can comprise rotary valves 71, 73, 75, 77, and 79. Each rotary valve can function to direct the flow of metered amounts of different reagents from different respective reagent reservoirs connected thereto, as described below, to main conduit system 50. Syringe pumps 58, 78, and 82 can be in fluid communication with valves 73, 75, 77 and 79, respectively. Pumps 42, 43, 44, and 45 can be in fluid communication with rotary valves 73, 75, 77 and 79, respectively.

Fluid processing system 10 can comprise a first waste conduit system 81. Waste conduit system 81 can comprise conduits connecting the following components: valves V-17, V-20, V-21, V-22, V-23, V-24, V-25, and a waste reservoir 83. Waste conduit system 81 can provide a fluid communication between and cross-intersections 68, 70, 76, 86, and 88 and waste reservoir 83.

Fluid processing system 10 can comprise a second waste conduit system 48. Second waste conduit system 48 can comprise conduits connecting a pump 87, a waste reservoir 85, and a valve V-26, that interface with output conduit 54. Second waste conduit system 48 can be used to remove liquids from output conduit 54.

Fluid processing system 10 can comprise reagent reservoirs 89, 91, 93, 95, 97, and 99 and can be in fluid communication with rotary valves 75, 77, 77, 79, 79, and 73, respectively. Reagent reservoir 89 can contain, for example, an exo-nuclease and shrimp alkaline phosphatase. Reagent reservoir 91 can contain, for example, nucleic acid amplification reaction forward primers. Reagent reservoir 93 can contain, for example, nucleic acid amplification reaction chain terminating dyes. Reagent reservoir 95 can contain, for example, nucleic acid amplification reaction reverse primers. Reagent reservoir 97 can contain, for example, nucleic acid amplification reaction chain terminating dyes. Reagent reservoir 99 can contain, for example, a nucleic acid amplification reaction master mix comprising, for example, reactive single base nucleotides, buffer, a polymerase, and the like, for example, to carry out a polymerase chain reaction.

According to various embodiments, fluid processing system 10 can comprise a rinse conduit system 30. Rinse conduit system 30 can provide a fluid communication between a rinse fluid reservoir 28, rotary valve 73, rotary valve 75, and immiscible-fluid-discrete-volume-forming conduit 12. Rinse fluid reservoir 28 can contain a rinse fluid 26. Rinse fluid 26 can comprise microbiologic grade water, for example, distilled, deionized water.

Rinse fluid 26 can be used to remove residual sample, for example, from immiscible-fluid-discrete-volume-forming conduit 12. Rinse fluid can be provided to multi-well plate 20, by way of rinse conduit system 30. Rinse fluid 26 can be used as a rinse at the input station, and/or can be used as a rinse fluid, a dilution fluid, or both, elsewhere in the system. In some embodiments, rinse fluid 26 can be added to immiscible-fluid, discrete volumes to adjust the volume or concentration thereof, in conjunction with an addition station, as described in FIG. 1C.

According to various embodiments, fluid processing system 10 can comprise a spacing fluid conduit system 36. Spacing fluid conduit system 36 can provide a fluid communication between a spacing fluid reservoir 34, vacuum pump 41, and multi-well plate 20. Spacing fluid reservoir 34 can contain an oil 32, or other spacing fluid that is immiscible with an immiscible-fluid-discrete-volume-forming fluid, for example, an aqueous slug fluid.

In some embodiments, the spacing fluid can be non-aqueous. The spacing fluid can comprise an organic phase, for example, a polydimethylsiloxane oil, a mineral oil (e.g., a light white mineral oil), a silicon oil, a hydrocarbon oil (e.g., decane), a fluorinated fluid or a combination thereof.

Fluorinated compounds such as, for example, perfluorooctyl bromide, perfluorodecalin, perfluoro-1,2-dimethylcyclohexane, FC 87, FC 72, FC 84, FC 77, FC 3255, FC 3283, FC 40, FC 43, FC 70, FC 5312 (all "FC" compounds are available from 3M, St. Paul, Minn.), the Novec® line of HFE compounds (also available from 3M, St. Paul, Minn.), such as, for example, HFE-7000, HFE-7100, HFE-7200, HFE-7500, and perfluorooctylethane can also be used as the spacing fluid. Combinations, mixtures, and solutions of the above materials can also be used as the spacing fluid.

In some embodiments, fluorinated alcohols, such as, for example, 1H, 1H, 2H, 2H-perfluoro-decan-1-ol, 1H, 1H, 2H, 2H-perfluoro-octan-1-ol, and 1H, 1H-perfluoro-1-nonanol can be added to a fluorinated compound, such as those listed above, to improve the stability of aqueous discrete volumes within the spacing fluid, but still maintain the ability to coalesce upon contact. In some embodiments, fluorinated alcohols can be added in a range of approximately 0.1% to approximately 5% by weight. In some embodiments, the fluorinated alcohol additive can be approximately 0.1%, 0.2%, 0.5%, 1.0%, 1.5%, 2.0%, 3.0%, 4.0% or 5% by weight of the fluorinated compound. In some embodiments, the fluorinated alcohol additive can be from approximately 1% to approximately 10% by volume of the fluorinated compound. In some embodiments, the fluorinated alcohol additive may comprise approximately 1%, 2%, 3%, 4%, 5%, 6%, 7%, 8%, 9%, or 10% by volume of the spacing fluid. In some embodiments, F-alkyl dimorpholinophosphates can be added as surfactants to fluorinated compounds.

In some embodiments, the organic phase can include non ionic surfactants such as sorbitan monooleate (Span 80 (no. S-6760, Sigma)), polyoxyethylenesorbitan monooleate (Tween 80 (no. S-8074, Sigma)), sorbitan monostearate (Span 60), octylphenoxyethoxyethanol (Triton X-100 (no. T9284, Sigma)). In some embodiments, Span 80 can be added in an amount ranging from about 1.0% to about 5.0%, or about 3.0% to about 4.5%. In some embodiments, adding surfactants in the quantities of 4.5% Span 80, 0.40% Tween 80, and 0.05% Triton X-100 to mineral (no. M-3516, Sigma) can result in the creation of stable emulsified droplets.

In some embodiments, the organic phase can include ionic surfactants, such as sodium deoxycholate, sodium cholate, and sodium taurocholate. In some embodiments, the organic phase can include chemically inert silicone-based surfactants, such as, for example, polysiloxane-polycetyl-polyethylene glycol copolymer. In some embodiments, the non-aqueous, spacing fluid can have a viscosity between approximately 0.5 to approximately 0.75 centistokes. In some embodiments, the non-aqueous spacing fluid can have a viscosity between approximately 0.75 centistokes to about 2.0 centistokes. In some embodiments, the non-aqueous spacing fluid can have a viscosity greater than 2.0 centistokes. In some embodiments, the non-aqueous spacing fluid can have a viscosity between 0.5 to greater than about 2.0 centistokes. In some embodiments, the non-aqueous spacing fluid can have a viscosity greater than 2.0 centistokes. In some embodiments, the non-aqueous, spacing fluid can have a boiling point greater than or equal to 100° C.

Spacing fluid 32 can function to separate discrete volumes of an immiscible-fluid-discrete-volume-forming fluid, for example, and aqueous sample, before, during, or after the immiscible-fluid-discrete-volume-forming fluid has been introduced into system 10. Spacing fluid can be provided to multi-well plate 20, from a spacing fluid reservoir 34, by way of a spacing fluid conduit system 36.

According to some embodiments, a de novo nucleic acid sequencing method is provided that uses system 10. The de novo sequencing method can be used to sequence an entire genome or portions thereof. The de novo sequencing method can be useful when the location of a nucleic acid sequence of interest is not known. The de novo sequencing method can be especially useful when the nucleic acid sequence of an organism is not known.

In some embodiments, a de novo sequencing method comprises pre-processing a sample, separating the sample into a set of immiscible-fluid-discrete-volumes, amplifying nucleic acids in the set of immiscible-fluid-discrete-volumes to form a set of amplified immiscible-fluid-discrete-volumes, incubating the set of amplified immiscible-fluid-discrete-volumes with primer and enzyme deactivation agents, amplifying the resulting nucleic acids using sequencing reactions to form detectable products, and detecting the detectable products.

In some embodiments the method can comprise pre-processing a sample before it is input into system 10. The pre-processing of a sample can comprise fragmenting the nucleic acid present in the sample. The fragmentation can be accomplished by any suitable method known in the art. For example, the nucleic acid can be fragmented by enzymatic digestion, or physical disruption methods, for example, hydro-shearing or sonication. In some embodiments the nucleic acid can be fragmented to an average size of about 1 KB, 2 KB, or 3 KB, for example.

According to some embodiments, the pre-processing of sample can comprise ligating designed nucleic acid sequences to a sample, for example universal sequences. In general, universal sequences can be used to facilitate nucleic acid amplification. Zip code, ID tag, or universal sequences can be artificially designed sequences, Zip code, ID tag, or universal sequences can be designed to have essentially no homology with the target nucleic acids. Zip code, ID tag, or universal sequences can be designed to resist the formation of dimers among themselves (self-annealing). Zip code, or universal sequences can be designed to bind with analogous primers with a consistent efficiency. Zip code, ID tag, or universal sequences can be selected based on their ability to resist mis-hybridization.

According to some embodiments, the present teachings can encompass a de novo sequencing method wherein universal sequences can be attached to the 5' ends of the DNA fragments in a sample by, for example, T4 DNA ligase, thereby forming a universal tail. The universal sequences can be double stranded (ds) or single stranded (ss). Primers containing zipcode sequences can be used to amplify these DNA fragments. The universal tail sequences can function as sites of complementarity for universal primers. Details of zip code primers and sample identification procedures, and methods that can be used herein, can be found, for example, in U.S. Patent Application Publication No. 2004/0185484, to Costa et al., in international Patent Application Publication No. WO 2005/098040, and in international Patent Application Publication No. WO 2005/094532, which are incorporated herein in their entireties, by reference.

According to various embodiments, the amplifying of a nucleic acid can comprise a thermal cycling nucleic acid sequence amplification process or an isothermal nucleic acid sequence amplification process. If a thermal cycling nucleic acid sequence amplification process is used, the process can comprise, for example, a polymerase chain reaction (PCR). The nucleic acid sequence amplification reaction can comprise an exponential amplification process, for example, PCR, or a linear amplification process, as can occur during, for example, during Sanger cycle sequencing. In various embodiments, other nucleic acid amplification processes can be used, for example, ligase chain reaction (LCR), nucleic acid sequence based amplification (NASBA), Q-beta replicase (QB) amplification, or strand displacement amplification (SDA). These alternatives, as well as others known to one skilled in the art, can be used either by themselves or in combination with PCR to amplify nucleic acids.

According to various embodiments, nucleic acid sequence processing methods comprising a first type of nucleic acid amplification reaction followed by one or more of a second different type of amplification reaction, and/or detection assay reaction, can be carried out, for example, as described in U.S. Patent Application No. 60/699,782 to Faulstich et al., filed Jul. 15, 2005, and in U.S. patent application Ser. No. 11/487,729 to Faulstich et al., filed Jul. 17, 2006, which are incorporated herein in their entireties by reference.

According to various embodiments, pre-processing a sample can comprise adding to the sample reagents to facilitate a nucleic acid amplification reaction. For example, the four dNTP's (dATP, dTTP, dGTP, and dCTP), a polymerase, oligonucleotide primers, and/or chelating agents can be added to the sample. Oligonucleotide primers can be chosen as determined by one of skill in the art to accomplish the desired objective, for example, zip code primers can be used.

According to various embodiments, pre-processing a sample can comprise diluting the sample with a miscible solvent, vehicle, or carrier. The sample can be diluted at a ratio of 1:1, 1:10, 1:100, 1:1000, or 1:10,000, for example. Exemplary ranges of dilution can be from about 1:1 to about 1:100, or from about 1:10 to about 1:50. For example, the sample can be diluted such that only a single fragment of nucleic acid is present per 1000 nanoliters of diluted sample. In some embodiments, the concentration of target fragments can be based on the size of the immiscible-fluid-discrete-volumes generated that carry the target fragments, such that an average of about 1 target fragment is present per 1.4 immiscible-fluid-discrete-volumes generated. In some embodiments, for example, a single target nucleic acid can be present in less than one out of 4 immiscible-fluid-discrete-volumes. In other embodiments, for example a single target nucleic acid can be present in less than one in 10 immiscible-fluid-discrete-volumes. According to various embodiments, the sample can be diluted such that at most about 40% of the immiscible-fluid-discrete-volumes produced from a sample in the process described below can comprise a single target nucleic acid sequence. In various other embodiments, less than about 37% of the immiscible-fluid-discrete-volumes produced can each comprise a single target nucleic acid sequence. In other embodiments, at least 1% or more, 5% or more, 10% or more, or 20% or more can comprise a single target nucleic acid sequence, for example, from about 5% to about 40%, or from about 10% to about 20%.

After optional preprocessing, the sample fluid is introduced to system 10 to form one or more discrete volumes of the sample fluid in a spacing fluid with which it is immiscible. According to various embodiments, the method can comprise forming immiscible-fluid-discrete-volumes of discrete amounts of sample and/or reagents inside conduit system 50. A plurality of immiscible-fluid-discrete-volumes can be associated together as a set of immiscible-fluid-discrete-volumes. Each set of immiscible-fluid-discrete-volumes can comprise immiscible-fluid-discrete-volumes separated from one another by a spacing fluid, for example, an oil. Each immiscible-fluid-discrete-volume of a set can be equally spaced from one or more adjacent immiscible-fluid-discrete-volumes of the set. Multiple sets of immiscible-fluid-discrete-volumes can be present at the same time in main conduit 50. Each set of immiscible-fluid-discrete-volumes can be separated from one or more other sets of immiscible-fluid-discrete-volumes by spacing fluid. In some embodiments, two or more sets of immiscible-fluid-discrete-volumes are spaced from one another a distance that is greater than the average distance between adjacent immiscible-fluid-discrete-volumes with the same set.

In the embodiment depicted in FIGS. 1A and 1B, immiscible-fluid-discrete-volumes that have been aspirated into immiscible-fluid-discrete-volume-forming conduit 12 can be moved into holding conduit 56 by suction produced by vacuum pump 40. Vacuum pump 40 can also be a syringe pump, in some embodiments. More details about an exemplary method of forming sets of immiscible-fluid-discrete-volumes are provided herein, for example, at least in connection with the description of FIGS. 16 and 17 herein.

According to various embodiments, a sample to be subjected to de novo sequencing can comprise a single copy of the genomic DNA of an organism. The sample DNA can be sheared, and universal sequences can be ligated to the sample. Nucleic acid amplification reagents can be added to the sample before the sample is drawn into system 10 or after the sample has been drawn into system 10. The nucleic acid amplification reagents can comprise universal primers, for example, primers that are specific to the universal sequences ligated to the sample nucleic acid fragments. The sample can be diluted such that when the sample is made into immiscible-fluid-discrete-volumes by system 10, each immiscible-fluid-discrete-volume does not contain more than one nucleic acid fragment. For example, 1, 2, 3, 4, or 5 out of ten immiscible-fluid-discrete-volumes can contain nucleic acid fragments.

According to some embodiments, the method can comprise moving a set of immiscible-fluid-discrete-volumes, from T-intersection 52, to cross-intersection 70, by way of conduit system 50. If a set of immiscible-fluid-discrete-volumes does not contain nucleic acid amplification reagents, the reagents can be added to each immiscible-fluid-discrete-volume of the set of immiscible-fluid-discrete-volumes at cross-intersection 70. Reactant addition to each immiscible-fluid-discrete-volume can be metered by rotary valves 71 and 73. Detector D-3 can detect the arrival of the beginning and/or the end of a set of sample immiscible-fluid-discrete-volumes at cross-intersection 70. Detector D-21 can detect the arrival of the beginning and/or the end of immiscible-fluid-discrete-volumes at cross-intersection 70. Valve V-7 can control the movement of a set of immiscible-fluid-discrete-volumes out of cross-intersection 70, and/or isolate the thermal-cyclers during thermal cycling.

According to some embodiments, the method can comprise moving a set of immiscible-fluid-discrete-volumes from cross-intersection 70, through main conduit system 50, to thermal-cycler 74. Detector D-8 can be used to detect the arrival of a set of immiscible-fluid-discrete-volumes at thermal-cycler 74. Detector D-8 can be used to detect the end of a set of immiscible-fluid-discrete-volumes, and thereby detect that a set of immiscible-fluid-discrete-volumes is disposed in thermal-cycler 74. A set of immiscible-fluid-discrete-volumes can be thermally cycled, for one or more cycles, for example, for from about 5 to about 50 temperature cycles or from about 20 to about 30 temperature cycles.

According to various embodiments, the method can comprise introducing polymerase chain reaction inactivating reagents into main conduit 50 after amplifying the at least one target nucleic acid sequence and before subjecting the nucleic acid sequence to a sequencing reaction. The reagents can be used to inactivate or remove or eliminate excess primers and/or dNTP's. The inactivating reagents can be introduced at an junction in the conduit, for example, after an immiscible-fluid-discrete-volume to be inactivated is aligned with the junction. The junction can comprise, for example, a T-junction.

According to some embodiments the method can comprise moving a set of immiscible-fluid-discrete-volumes from thermal-cycler 74, through cross-intersection 76. As the set of immiscible-fluid-discrete-volumes moves through cross-intersection 76, the method can comprise adding exonuclease and shrimp alkaline phosphatase to each immiscible-fluid-discrete-volume of the set of immiscible-fluid-discrete-volumes. For example, the exonuclease and shrimp alkaline phosphatase can be metered out in discrete volumes which merge respectively with the immiscible-fluid-discrete-volumes of a set of immiscible-fluid-discrete-volumes at an intersection in rotary valve 77. For example, exonuclease and shrimp alkaline phosphatase can be added to each immiscible-fluid-discrete-volumes of the set of immiscible-fluid-discrete-volumes in cross-intersection 76. Valve V-8 can be used to isolate the thermal-cyclers. For example, different thermal-cyclers can be operated at the same times, but at different thermal profiles, and valve V-8 could function to isolate the thermal expansion and contraction due to the different thermal profiles.

In the exemplary system shown, detector D-6 can detect the arrival of the beginning and/or the end of a set of sample discrete volumes at cross-intersection 76. Detector D-18 can detect the arrival of the beginning and/or the end of one or more immiscible-fluid-discrete-volumes of exonuclease and shrimp alkaline phosphatase at cross-intersection 76. Valve V-8 can control the movement of a set of immiscible-fluid-discrete-volumes out of cross-intersection 76.

In the exemplary embodiment shown, a set of immiscible-fluid-discrete-volumes containing exonuclease and shrimp alkaline phosphatase can be moved into thermal-cycler 80, via main conduit system 50. Detector D-9 can detect the arrival of the beginning and/or the end of a set of immiscible-fluid-discrete-volumes at thermal-cycler 80. The set of immiscible-fluid-discrete-volumes can be incubated at from about 25° C. to about 35° C. for a time period of from about one minute, to about 60 minutes or from about two minutes to about 10 minutes. The time period of thermal-cycling may be different for different thermal-cyclers. The incubation step can function to facilitate the activities of the exonuclease and shrimp alkaline phosphatase. A set of immiscible-fluid-discrete-volumes can be further incubated at a temperature of from about 75° C. to about 85° C., for a time period of from about 10 seconds to about 10 minutes, or from about one minute to about five minutes. The incubation at from about 75° C. to about 85° C. can function to heat-kill any enzymes that might still be present in the set of immiscible-fluid-discrete-volumes.

According to some embodiments, the method can comprise moving a set of immiscible-fluid-discrete-volumes to T-intersection 84. Valve V-9 can control the movement of a set of immiscible-fluid-discrete-volumes from thermal-cycler 80, to T-intersection 84. Detector D-10 can detect the arrival of the beginning and/or the end of a set of immiscible-fluid-discrete-volumes at T-intersection 84. The method can comprise dividing a set of immiscible-fluid-discrete-volumes into two or more subsets or portions, for example, dividing the set into two halves such as a forward set of immiscible-fluid-discrete-volumes and a reverse set of immiscible-fluid-discrete-volumes, at T-intersection 84. The method can comprise moving the forward set of immiscible-fluid-discrete-volumes along main conduit system 50, to cross-intersection 86. Forward primers and chain terminating dyes can be moved from reservoirs 91 and 93, to rotary valve 77. The forward primers and chain terminating dyes can be metered out by rotary valve 77. The forward primers and chain terminating dyes can be moved to cross-intersection 86 and be added to each immiscible-fluid-discrete-volume of the forward set of immiscible-fluid-discrete-volumes. According to various embodiments, the method can comprise moving the reverse set of immiscible-fluid-discrete-volumes along main conduit system 50, to cross-intersection 88. Reverse primers and chain terminating dyes can be moved from reservoirs 95 and 97, to rotary valve 79. The reverse primers and chain terminating dyes can be metered out by rotary valve 79. The reverse primers and chain terminating dyes reagent can be moved to cross-intersection 86 and be joined with each of the reverse set of immiscible-fluid-discrete-volumes.

In some embodiments, the method can comprise moving the forward set of immiscible-fluid-discrete-volumes from cross-intersection 86, along main conduit system 50, to thermal-cycler 90. The forward set of immiscible-fluid-discrete-volumes can be thermally cycled for from about 5 to about 50, temperature cycles, or for example, from about 20 to about 40 thermal cycles.

In some embodiments, the method can comprise moving the reverse set of immiscible-fluid-discrete-volumes from cross-intersection 88, along main conduit system 50, to thermal-cycler 92. The reverse set of immiscible-fluid-discrete-volumes can be thermally cycled for from about 5 to about 50 thermal cycles, or for example, from about 20 to about 40 cycles, temperature cycles.

According to various embodiments, the method can comprise moving the forward and the reverse sets of immiscible-fluid-discrete-volumes from their respective thermal-cyclers to output conduit 54. Output conduit 54 can deposit both sets of immiscible-fluid-discrete-volumes on, for example, a multi-well plate. In some embodiments the forward and reverse sets are merged before deposition. In other embodiments the forward and reverse sets are output one set at a time.

According to some embodiments, a dye can be added to one or more immiscible-fluid-discrete-volumes of a set of immiscible-fluid-discrete-volumes. The dye can comprise a double-strand (ds), nucleic acid intercalating dye, for example, SYBR green, SYBR gold, EVA green, LC green, or the like. The dye can be added to an aqueous immiscible-fluid-discrete-volume-forming fluid, such as an aqueous sample, before it is added to system 10. The dye can be added to a set of immiscible-fluid-discrete-volumes at any cross-intersection of system 10. The dye can be used to discriminate between immiscible-fluid-discrete-volumes that contain ds nucleic acids, and immiscible-fluid-discrete-volumes that do not contain ds nucleic acids. The immiscible-fluid-discrete-volumes that do not contain ds nucleic acids can be removed from output conduit 54 before the immiscible-fluid-discrete-volumes are deposited on a multi-well plate 47. The immiscible-fluid-discrete-volumes that do not contain a detectable amount of ds nucleic acids can be moved through second waste conduit system 48, to waste reservoir 85. In some embodiments, a dye can be detected by detector 98 to determine whether a discrete volume should be sent to second waste reservoir 85 or be collected. Pump 87 can apply a negative pressure to waste conduit system 48, which can cause the movement of immiscible-fluid-discrete-volumes into waste reservoir 85. In other embodiments the set of immiscible-fluid-discrete-volumes can be sorted (removed) after nucleic acid amplification but before sequencing amplification. Oil can be added to take the place of immiscible-fluid-discrete-volumes that have been removed to insure the volume in the thermal-cyclers stays the same.

Shown below is Table 1, which shows a state diagram of various settings that can be implemented for the various valves and detectors of the system shown in FIGS. 1A and 1B, to achieve various different functions, for example, an embodiment of the de novo sequencing method described above.

TABLE 1

|  | V-1 | V-2 | V-3 | V-4 | V-5 | V-6 | V-7 | V-8 | V-9 | V-10 | V-11 | V-12 | V-13 | V-14 | V-15 | V-16 | V-17 |
|---|---|---|---|---|---|---|---|---|---|---|---|---|---|---|---|---|---|
| Prime SMA Sample | 0 | 1 | 0 | 1 | 0 | 0 |  |  |  |  |  |  | 0 |  |  |  |  |
|  | 0 | 1 | 0 | 1 | 0 | 0 |  |  |  |  |  |  | 0 |  |  |  |  |
|  | 0 | 1 | 0 | 1 | 0 | 0 |  |  |  |  |  |  | 0 |  |  |  |  |
| Deliver initial portion of SMAF/MM mixture to ZT-1 | 0 | 1 | 0 | 1 | 0 | 0 |  |  |  |  |  |  | 0 |  |  |  |  |
|  | 0 | 0 | 1 | 0 | 1 | 0 | 0 |  |  |  |  |  | 0 |  |  |  |  |
| Deliver initial portion of oil to ZT-1 | 0 | 0 | 0 | 0 | 0 | 0 | 0 |  |  |  |  | 0 | 1 | 1 | 0 | 1 | 0 |
| Form initial SMAF Zebra | 0 | 0 | 1 | 0 | 1 | 0 | 1 | 0 |  |  |  | 0 | 1 | 1 | 0 | 1 | 0 |
| Deliver intermediate portion(s) of SMAF.MM mixture toZT-1 | 0 | 1 | 0 | 1 | 0 | 0 |  |  |  |  |  |  |  |  |  |  |  |
|  | 0 | 0 | 1 | 0 | 1 | 0 | 1 | 0 |  |  |  | 0 | 1 | 1 | 0 | 1 | 0 |
| Deliver final portion(s) of SMAF.MM mixture toZT-1 | 0 | 1 | 0 | 1 | 0 | 0 |  |  |  |  |  |  |  |  |  |  |  |
|  | 0 | 0 | 1 | 0 | 1 | 0 | 1 | 0 |  |  |  | 0 | 1 | 1 | 0 | 1 | 0 |
| Amplify DNA |  |  |  |  |  |  | 0 | 0 |  |  |  |  |  |  |  |  |  |
| Prime ES reagent path |  |  |  |  |  |  | 0 | 0 | 1 | 1 |  |  |  |  |  |  |  |
|  |  |  |  |  |  |  | 0 | 0 | 1 | 1 |  |  |  |  |  |  |  |
| Add ES reagents and load clean up thermal cycler |  |  |  |  | 0 | 0 | 1 | 1 | 1 | 1 | 1 | 0 | 1 | 1 | 0 | 1 | 0 |
|  |  |  |  |  | 0 | 0 | 1 | 1 | 1 | 1 | 1 | 0 | 1 | 1 | 0 | 1 | 0 |
| Clean up after PCR |  |  |  |  |  |  | 0 | 0 |  |  |  |  |  |  |  |  |  |
| Prime PF + BD paths |  |  |  |  |  |  |  |  | 0 | 0 | 0 |  |  |  |  |  |  |
|  |  |  |  |  |  |  |  |  | 0 | 0 | 0 |  |  |  |  |  |  |
| Add FP + BD and RP + BD & load cycle sequencing sticky bun |  |  |  |  | 0 | 0 | 1 | 1 | 1 | 1 | 1 | 0 | 1 | 1 | 0 | 1 | 0 |
|  |  |  |  |  | 0 | 0 | 1 | 1 | 1 | 1 | 1 | 0 | 1 | 1 | 0 | 1 | 0 |

TABLE 1-continued

| | V-18 | V-19 | V-20 | V-21 | V-22 | V-23 | V-24 | V-25 | V-26 | Rotary Valve-ES | Rotary Valve-FP&BD | Rotary Valve-MM_SMF |
|---|---|---|---|---|---|---|---|---|---|---|---|---|
| Cycle sequence | | | | | | | 0 | 0 | 0 | | | |
| Dispense sample-laden FP slugs to tray, dispose of other fluids | 0 | 0 | 1 | 1 | 1 | 1 | 0 | 0 | 1 | 1 | 0 | 1 |
| | | | | | | | | | | | | 0 |
| Prime SMA Sample | 1 | 0 | 1 | | | | | | | | | 0 |
| | 0 | 0 | 1 | | | | | | | | | Oil |
| | 0 | 0 | 1 | | | | | | | | | MM |
| Deliver initial portion of SMAF/MM mixture to ZT-1 | 1 | 0 | 1 | | | | | | | | | MM |
| | | 1 | 0 | | 1 | | | | | | | MM |
| Deliver initial portion of oil to ZT-1 | 0 | 0 | 0 | | 1 | | | | | | | Off |
| Form initial SMAF Zebra | 1 | 1 | 0 | 0 | 0 | 1 | | | | | | |
| Deliver intermediate portion(s) of SMAF.MM mixture toZT-1 | | 1 | 1 | | 1 | | | | | | | MM |
| | 1 | 0 | 0 | 0 | 0 | 1 | | | | | | |
| Deliver final portion(s) of SMAF.MM mixture toZT-1 | 1 | | 1 | 1 | | | | | | | | MM |
| | | 0 | 0 | 0 | 1 | | | | | | | |
| Amplify DNA | | | | | 0 | | | | | 0 | | |
| Prime ES reagent path | | | | | 1 | | | | | Oil out | | |
| | | | | | 1 | | | | | ES out | | |
| Add ES reagents and load clean up thermal cycler | | | 0 | 0 | 0 | 0 | 0 | | | out | 0 | |
| | | | 0 | 0 | 0 | 0 | 0 | | | 0 | 0 | |
| Clean up after PCR Prime PF + BD paths | | | | | | | | | | | | |
| | | | | | 1 | 1 | | | | Oil out FP BD | | |
| | | | | | 1 | 1 | | | | Oil out | | |
| Add FP + BD and RP + BD & load cycle sequencing sticky bun | | | 0 | 0 | 0 | 0 | 0 | | | 0 | out | |
| | | | 0 | 0 | 0 | 0 | 0 | | | 0 | 0 | |
| Cycle sequence | | | | | | 0 | 0 | | | | 0 | |
| Dispense sample-laden FP slugs to tray, dispose of other fluids | | 0 | 0 | 0 | 0 | 0 | 0 | 1 | | 0 | 0 | |
| | | 0 | 0 | 0 | 0 | 0 | 0 | | | 0 | 0 | |

| | Rotary Valve-MN_V1 | VICI-1 | VICI-2 | SP-MM | SPES | SP-FP&BD | SP-RP&BD | Footnote |
|---|---|---|---|---|---|---|---|---|
| Prime SMA Sample | | | 1 | | | | | 1 |
| | | 0 | 1 | | | | | 2 |
| | | 0 | 1 | | | | | 3 |
| Deliver initial portion of SMAF/MM mixture to ZT-1 | | 0 | 1 | | | | | 4 |
| | | 0 | 1 | | | | | 5 |
| Deliver initial portion of oil to ZT-1 | | 0 | 1 | | | | | 6 |
| Form initial SMAF Zebra | | | | | | | | 7 |

TABLE 1-continued

| | | | | | | | | | |
|---|---|---|---|---|---|---|---|---|---|
| Deliver intermediate portion(s) of SMAF.MM mixture to ZT-1 | 0 | 1 | | | | | | | 8 |
| | | 1 | 1 | | | | | | 9 |
| Deliver final portion(s) of SMAF.MM mixture to ZT-1 | 0 | | 1 | | | | | | 10 |
| | | 1 | 1 | | | | | | 11 |
| Amplify DNA | | | | | | | | | |
| Prime ES reagent path | | | | | | | | | 12 |
| | | | | | | | | | 13 |
| Add ES reagents and load clean up thermal cycler | 0 | 0 | 1 | 0 | out | 0 | 0 | | 14 |
| | 0 | 0 | 1 | 0 | 0 | 0 | 0 | | 15 |
| Clean up after PCR | | | | | | | | | |
| Prime PF + BD paths | | | | | | | | | 16 |
| | Oil out | | | | | In out | In out | | 17 |
| | | | | | | In | In | | 18 |
| | RF | | | | | In | In | | 19 |
| | BD | | | | | In | In | | 20 |
| | Oil out | | | | | In out | In out | | 21 |
| Add FP + BD and RP + BD & load cycle sequencing sticky bun | out 0 | 1 1 | 0 0 | 0 0 | 0 0 | 1 0 | 1 0 | | 22 |
| Cycle sequence | 0 | | | | | | | | |
| Dispense sample-laden FP slugs to tray, dispose of other fluids | 0 0 | 1 1 | | | | | | | 23, 24 |

Footnotes:
1 Pull SMAF into T-intersection (67);
2 Pull oil through T-intersection (67);
3 Pull MM through T-intersection (67);
4 Pull SMAF + MM through D-17;
5 Push SMAF + MM towards T-intersection (66) until D-5 detects AF;
6 Pull, Push oil towards T-intersection (66) until D-4 detects oil;
7 Push oil + SMAF + MM through thermal cycler until D-6 detects zebras or, more likely, D-2 sees only oil;
8 Push SMAF + MM through D-17;
9 Push oil + SMAF + MM through thermal cycler until D-6 detects zebras or, more likely, D-2 sees only oil;
10 Pull SMAF + MM towards D-17. After total volume of SMAF has entered T-intersection (67), close V-18. After total volume of MM has left Rotarty Valve (71). switch Rotary Valve (71) to "oil" position. Continue pulling SMAF + MM towards D-17 until D-2 sees a;
11 Push oil + SMAF + MM through thermal cycler until D-6 detects zebras or, more likely, D-5 sees only oil;
12 Push oil until D-16 detects oil;
13 Push ES until D-18 detects ES, then push further distance calculated to advance ES to Zebra path.;
14 Push until D-6 detects end of batch, then push further distance calculated to advance batch just past ES adder;
15 Push until D-9 detects end of batch, then push farther distance calculate to advance batch completely into cleanup thermal cycler;
16 Push SP (78) until D-19 sees oil. Push SP (82) until D-20 sees oil.;
17 Pull portion of FP into SP (78). Pull portion of RP into SP (82);
18 Pull portion of BD into SP (78). Pull portion of BD into SP (82);
19 Pull alternating sub-portions of primers and big dyes until complete portion has been loaded;
20 Pull small amount of oil so all aqueous fluids advance into syringe;
21 Push SP (78) until D-19 sees FP + BD. Push SP (82) until D-20 sees RP + BD. Push farther distance calculated to advance FP + BD and RP + BD to Zebra path;
22 Push with pumps until D-11 and D-7 sec oil, then push further distance calculated to advance batch just past RP + BD and FP + BD adders;
23 Push with pumps further distance calculated to advance batch into cycle sequencing thermal cycler;
24 Push until FSD-1 detects sample-laden FP slug, then push further distance calculated to move downstream boundary of sample-laden slug just inside dispense tip;
25 Push distance calculated to bead sample-laden slug on dispense tip. Touch bead to bottom of sample well.

According to various embodiments, the present teachings can encompass a resequencing method using system 10. In general, the resequencing method is similar to the de-novo method described herein with modifications as discussed herein.

In some embodiments, the pre-processing of a sample for resequencing comprises shearing a robust sample of nucleic acid having a plurality of copies of one or more nucleic acids of interest, herein also referred to as target sequences. The nucleic acids in the sample can be sheared. The method can comprise adding a plurality of gene specific zip code primers to the sample before introduction to system 10, or the gene specific zip code primers can be added, at for example, at cross-junction 10, to a set of immiscible-fluid-discrete-volumes generated from the sample. Immiscible-fluid-discrete-volumes made from the sample can contain a single copy of a nucleic acid fragment or can contain a plurality of copies of one or more different nucleic acid fragments. Each immiscible-fluid-discrete-volume can contain, for example, from about 50 to about 150 different gene-specific zip code primers. The gene-specific zip code primers can be present at a relatively low concentration. Exemplary low concentrations can comprise from about 0.1 nanomolar primers per nanoliter (primers/nl) to about 1 micromolar primers/nl, or from about 10 nanomolar primers per nanoliter (primers/nl) to about 50 nanomolar primers/nl.

According to some embodiments, the method can comprise adding sequence-specific zip code primers, specific to a single zip code sequence, to each immiscible-fluid-discrete-volume of a set of immiscible-fluid-discrete-volumes. The sequence-specific zip code primers added to each immiscible-fluid-discrete-volume can be different for one immiscible-fluid-discrete-volume than for at least one other immiscible-fluid-discrete-volume, and can be complementary to the zip code sequences of a specific set of gene-specific zip code primers. The sequence-specific zip code primers can be present in a high concentration relative to the concentration of the gene-specific zip code primers. For example, the concentration of the sequence specific zip code primers can be in excess, and the concentration of the gene specific zip code primers can be limiting. The concentration of the sequence specific zip code primers can be present, relative to the concentration of the gene-specific zip code primers, at, for example, a ratio of from about 10 nanomolar to about 1 micromolar, or from about 100 nanomolar to about 500 nanomolar.

In some embodiments, the method can comprise moving a set of immiscible-fluid-discrete-volumes comprising the concentrations of primers discussed above, to thermal spiral 74. The set of immiscible-fluid-discrete-volumes can be thermally cycled and thereafter processed in any of the many manners disclosed herein for the de novo sequencing method. Various sequencing and re-sequencing methods that can be carried out according to various embodiments can include, for example, those depicted in FIGS. 2C-2K herein.

Shown below are Tables 2A and 2B which are the first and second halves of another state diagram of various settings that can be implemented for the various valves and detectors of the system shown in FIGS. 1A and 1B, to achieve various different functions. The various functions can include carrying out various different immiscible-fluid-discrete-volume processing, for example, carrying out the standard resequencing reactions depicted in FIGS. 2C-2D herein.

TABLE 2A

| | V-1 | V-2 | V-3 | V-4 | V-5 | V-6 | V-7 | V-8 | V-9 | V-10 | V-11 | V-12 | V-13 | V-14 | V-15 | V-16 | V-17 |
|---|---|---|---|---|---|---|---|---|---|---|---|---|---|---|---|---|---|
| Prime Primary VI Input Path | 0 | | | | 0 | 0 | | | | | | | 0 | 0 | 1 | 0 | 1 |
| Form VI Zebra | 0 | | | | 0 | 0 | | | | | | | 0 | 0 | 1 | 0 | 1 |
| | 0 | | | | 0 | 0 | | | | | | | 0 | 0 | 1 | 0 | 1 |
| | 0 | | | | 0 | 0 | | | | | | | 0 | 0 | 1 | 0 | 1 |
| | 0 | | | | 0 | 0 | | | | | | | 0 | 0 | 1 | 0 | 1 |
| | 0 | | | | 0 | 0 | | | | | | | 0 | 0 | 1 | 0 | 1 |
| Push Zebra Into Storage | 0 | | | | 0 | 0 | 0 | | | | | | 1 | 1 | 0 | 1 | 0 |
| Repeat "Form VI Zebra" and "Push Zebra Into Storage" until D-4 sees zebras or until the total required number of slugs is reached. | | | | | | | | | | | | | | | | | |
| Prime Secondary VI Input Path | 1 | 1 | 0 | 1 | 0 | 0 | | | | 0 | 0 | | | | | | |
| Form secondary VI fluid macro slugs | 1 | 1 | 0 | 1 | 0 | 0 | | | | 0 | 0 | | | | | | |
| | 1 | 1 | 0 | 1 | 0 | 0 | | | | 0 | 0 | | | | | | |
| Push Macro-Zebra Into Storage | | 0 | 1 | 0 | 0 | 0 | | | | | | | | | | | |
| Repeat "Form secondary VI fluid macro slugs" and "Push Macro-Zebra Into Storage" until D-4 sees zebras or until the total required number of slugs is reached. | | | | | | | | | | | | | | | | | |
| Add Secondary VI fluid to Zebra slugs | | 0 | 1 | 0 | 0 | 1 | 0 | 0 | | | | | 0 | 1 | 1 | 0 | 1 | 0 |
| Prime MM_VI | | | | | | | | | | | | | | | | | |
| Add MM to VI Zebra slugs | | 0 | 1 | 0 | 0 | 1 | 1 | 0 | | | | | 0 | 1 | 1 | 0 | 1 | 0 |
| Amplify DNA | | | | | | | 0 | 0 | | | | | | | | | |

| | V-18 | V-19 | V-20 | V-21 | V-22 | V-23 | V-24 | V-25 | V-26 | Rotary Valve (75) | Rotary Valve (77) | Rotary Valve (71) | Rotary Valve (73) | Rotary Valve (79) |
|---|---|---|---|---|---|---|---|---|---|---|---|---|---|---|
| Prime Primary VI Input Path | | | | | | | | | | | | | | |
| Form VI Zebra | | | | | | | | | | | | | | |
| Push Zebra Into Storage | | | | 1 | 1 | | | | | | | | | |
| Repeat "Form VI Zebra" and "Push Zebra Into Storage" until D-4 sees zebras or until the total required number of slugs is reached. | | | | | | | | | | | | | | |
| Prime Secondary VI Input Path | 0 | 0 | 1 | | | | | | | | | | | |
| Form secondary VI fluid macro slugs | 0 | 0 | 1 | | | | | | | | | | | |
| | 0 | 0 | 1 | | | | | | | | | | | |
| Push Macro-Zebra Into Storage | 1 | 0 | | | | | | | | | | | | |
| Repeat "Form secondary VI fluid macro slugs" and "Push Macro-Zebra Into Storage" until D-4 sees zebras or until the total required number of slugs is reached. | | | | | | | | | | | | | | |
| Add Secondary VI fluid to Zebra slugs | 1 | 0 | 0 | 1 | 0 | | | | | | | | | 0 |
| Prime MM_VI | | | | | | | | | | | | | 0 | MM |
| Add MM to VI Zebra slugs | 1 | 0 | 0 | 0 | 1 | | | | | | | | | Out |
| Amplify DNA | | | | | 0 | | | | | 0 | | | | |

TABLE 2A-continued

| | Pump (40) | Pump (39) | SP (58) | SP (66) | SP (78) | SP (82) | |
|---|---|---|---|---|---|---|---|
| Prime Primary VI Input Path | 1 | | | | | | Pull oil from reservoir until it reaches D-15, then pump distance calculated to advance oil at D-17 just past V-17. |
| Form VI Zebra | 1 | | | | | | Pull 78 nl primary VI fluid into tube through tip. Wash tip. |
| | 1 | | | | | | Pull 800 nl oil into tube through lip. Wash tip. |
| | 1 | | | | | | Pull 78 nl primary VI fluid from next well into tube through tip. Wash tip. |
| | 1 | | | | | | Pull 800 nl oil into tube through tip. Wash tip. |
| | 1 | | | | | | Continue aspiration steps until zebras (sequence of immiscible fluid volumes) are detected by D-15. |
| Push Zebra Into Storage | 1 | | | | | | Push oil until D-16 no longer sees slugs (individual fluid volumes). |
| Repeat "Form VI Zebra" and "Push Zebra Into Storage" until D-4 sees zebras or until the total required number of slugs is reached. | | | | | | | |
| Prime Secondary VI Input Path | | 1 | | | | | Pull oil from reservoir until it reaches D-17, then pump distance calculated to advance oil at D-17 just past V-17. |
| Form secondary VI fluid macro slugs | | 1 | | | | | Pull m(78 nl) of secondary VI fluid i into tube, where m is the number of primary VI fluids that are to be mixed with the ith secondary fluid. |
| | | 1 | | | | | Pull 800 nl oil into tube through lip. Wash tip. |
| | | 1 | | | | | Continue aspiration steps until zebras are detected by D-17. |
| Push Macro-Zebra Into Storage | | | | | | | Pump oil to push macro-zebra until D-2 no long sees macro-slugs. |
| Repeat "Form secondary VI fluid macro slugs" and "Push Macro-Zebra Into Storage" until D-4 sees zebras or until the total required number of slugs is reached. | | | | | | | |
| Add Secondary VI fluid to Zebra slugs | 1 | 1 | 0 | | | | Push micro and macro zebras until D-3 sees slugs |
| Prime MM_VI | | | 1 | | | | Load Syringe Pump (58) |
| Add MM to VI Zebra slugs Amplify DNA | 1 | 1 | 1 | | | | Runs pumps until D-6 sees slugs |

TABLE 2B

| | V-1 | V-2 | V-3 | V-4 | V-5 | V-6 | V-7 | V-8 | V-9 | V-10 | V-11 | V-12 | V-13 | V-14 | V-15 | V-16 | V-17 |
|---|---|---|---|---|---|---|---|---|---|---|---|---|---|---|---|---|---|
| Prime ES Reagent path | | | | | | | 0 | 0 | 1 | 1 | | | | | | | |
| | | | | | | | 0 | 0 | 1 | 1 | | | | | | | |
| Add ES Reagents & load cleanup thermal cycler | | | | | 0 | 0 | 1 | 1 | 1 | 1 | 1 | 0 | 1 | 1 | 0 | 1 | 0 |
| | | | | | 0 | 0 | 1 | 1 | 1 | 1 | 1 | 0 | 1 | 1 | 0 | 1 | 0 |
| Clean up after PCR | | | | | | | 0 | 0 | | | | | | | | | |
| Prime FP + BD and RP + BD paths | | | | | | | | | 0 | 0 | 0 | | | | | | |
| | | | | | | | | | 0 | 0 | 0 | | | | | | |
| Add FP + BD and RP + BD & load cycle sequencing thermal cycler | | | | | 0 | 0 | 1 | 1 | 1 | 1 | 1 | 0 | 1 | 1 | 0 | 1 | 0 |
| | | | | | 0 | 0 | 1 | 1 | 1 | 1 | 1 | 0 | 1 | 1 | 0 | 1 | 0 |
| Cycle sequence | | | | | | | | | 0 | 0 | 0 | | | | | | |
| Dispense sample-laden FP slugs to tray, dispose of other fluids | | | | | 0 | 0 | 1 | 1 | 1 | 1 | 0 | 0 | 1 | 1 | 0 | 1 | 0 |
| | | | | | 0 | 0 | 1 | 1 | 1 | 1 | 0 | 0 | 1 | 1 | 0 | 1 | 0 |

| | V-18 | V-19 | V-20 | V-21 | V-22 | V-23 | V-24 | V-25 | V-26 | Rotary Valve (75) | Rotary Valve (77) | Rotary Valve (71) | Rotary Valve (73) | Rotary Valve (79) |
|---|---|---|---|---|---|---|---|---|---|---|---|---|---|---|
| Prime ES Reagent path | | | | | | 1 | | | | Oil Out ES Out | | | | |
| Add ES Reagents & load cleanup thermal cycler | | | | 0 | 0 | 1 | 0 | 0 | 0 | Out | 0 | | 0 | 0 |
| | | | | | | | | | | 0 | 0 | | 0 | 0 |
| Clean up after PCR | | | | | | | | | | | | | | |
| Prime FP + BD and RP + BD paths | | | | | | | 1 | 1 | | Oil Out FP BD Oil Out | | | Oil Out RP BD Oil Out | |
| Add FP + BD and RP + BD & load cycle sequencing thermal cycler | | | | 0 | 0 | 0 | 0 | 0 | | 0 Out | 0 | | 0 Out | 0 |
| Cycle sequence | | | | | | | 0 | 0 | | 0 | | | 0 | |
| Dispense sample-laden FP slugs to tray, dispose of other fluids | | | | 0 | 0 | 0 | 0 | 0 | 1 | 0 | 0 | | 0 | 0 |
| | | | | 0 | 0 | 0 | 0 | 0 | 0 | 0 | 0 | | 0 | 0 |

TABLE 2B-continued

| | Pump (40) | Pump (39) | SP (58) | SP (66) | SP (78) | SP (82) | |
|---|---|---|---|---|---|---|---|
| Prime ES | | | | In | | | |
| Reagent path | | | | Out | | | Push oil until D-18 detects oil. |
| | | | | In | | | |
| | | | | Out | | | Push ES until D-18 delects ES, then push further distance calculated to advance ES to zebra path. |
| Add ES Reagents & load cleanup thermal cycler | 1 | 0 | 0 | Out | 0 | 0 | Push until D-6 detects end of batch, then push further distance calculated to advance batch just past ES adder. |
| | 1 | 0 | 0 | 0 | 0 | 0 | Push until D-9 detects end of batch, then push further distance calculate to advance batch completely into cleanup thermal cycler. |
| Clean up after PCR | | | | | | | |
| Prime FP + BD and RP + BD paths | | | | In Out | In Out | | Push SP-FP&BD until D-19 sees oil. Push SP (82) until D-20 sees oil. |
| | | | | In | In | | Pull portion of FP into SP (78). Pull portion of RP into SP-RP&BD. |
| | | | | In | In | | Pull portion of BD into SP (78). Pull portion of BD into SP (82). Pull alternating sub-portions of primers and big dyes until complete portion has been loaded. |
| | | | | In | In | | Pull small amount of oil so all aqueous fluids advance into syringe. |
| | | | | Out | Out | | Push SP (78) until D-19 sees FP + BD. Push SP (82) until D-20 sees RP + BD. Push farther distance calculated to advance FP + BD and RP + BD to zebra path. |
| Add FP + BD and RP + BD & load cycle sequencing thermal cycler | 1 | 0 | 0 | 0 | 1 | 1 | Push with pumps until D-11 and D-7 see oil, then push further distance calculated to advance batch just past RP + BD and FP + BD adders. |
| | 1 | 0 | 0 | 0 | 0 | 0 | Push with pumps further distance calculated to advance batch into cycle sequencning thermal cycler. |
| Cycle sequence | | | | | | | |
| Dispense sample-laden FP slugs to tray, dispose of other fluids | 1 | | | | | | Push until fluorescent detector (98) detects sample-laden FP slug, then push further distance calculated to move downstream boundary of sample-laden slug just inside dispense tip. |
| | 1 | | | | | | Push distance calculated to bead sample-laden slug on dispense tip. Touch bead to bottom of sample well. |

Figure 1C:
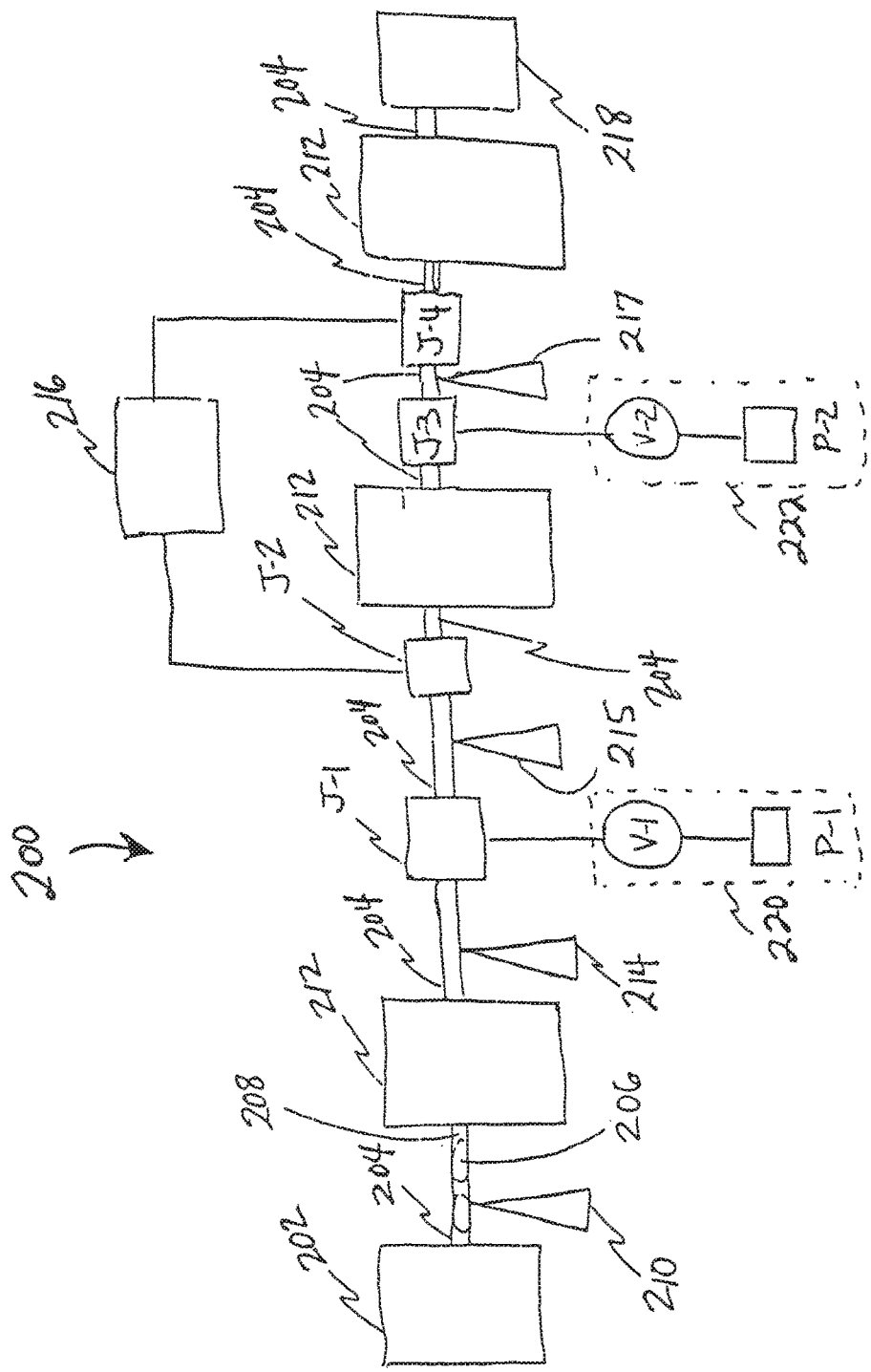
FIG. 1C is a simplified block diagram of a system configured to include embodiments described herein and to process the generated discrete volumes and to output the discrete volumes.

FIG. 1C is yet another system for processing immiscible-fluid-discrete volumes downstream of the apparatuses, methods, and systems disclosed herein.

A simplified system 5600 is illustrated in FIG. 1C. As illustrated, box 5602 represents a structure that delivers to tube 5604 of system 5600 discrete volumes 5606 of aqueous liquid in a non-aqueous liquid 5608 with which they are immiscible. Examples of such structures and methods of generating discrete volumes 5606 in contact with spacing fluid 5608 are described herein. In some embodiments, such a structure could be a tube of preformed discrete volumes 5606 of aqueous fluid. In some embodiments, such a structure could be a chip or other substrate with a channel therein containing the discrete volumes 5606 of aqueous fluid. As illustrated, tube 5604 extends throughout system 5600. After entering tube 5604, desired information about aqueous volumes 5606 are determined and optionally manipulated by structures in triangle 5610. For example, the length and speed of a slug and the distance between two adjacent slugs can be desired information. In that example, a slug detection system can provide that information. If the distance between adjacent slugs does not meet preferred values, then additional spacing fluid can be added between the trailing point of the first slug and the leading point of the second slug, or one of the slugs could be held in an electric field, for example, to allow more of the existing spacing fluid to flow past it in tube 5603. If the length, and therefore the volume, of an aqueous discrete volume does not meet preferred values, additional non-reactive, miscible liquid can be added by an apparatus at that area of tube 5604. Triangle 5610 represents these and other structures of discrete volume characteristic detection and manipulation. Examples of these structures and/or component parts of thereof are described herein.

System 5600, as illustrated in FIG. 1C, next incorporates a processing section 5612 of tube 5604 (not illustrated, but in the box), which can include, for example, vibration, heating, cooling, and electromagnetic radiation exposure. In some embodiments, processing section 5612 can include thermal cycling between one or more pre-determined temperatures for pre-determined durations as needed, for example, to perform PCR, or other amplification methods. In some embodiments, aqueous discrete volumes may continue to flow at a constant rate through processing section 5612 while undergoing a desired process, or alternatively, they may dwell in a particular location in processing section 5612. System 5600, as illustrated in FIG. 1C, includes another aqueous discrete volume characteristic determination and optional manipulation station 5614. Aqueous discrete volumes 5606 then flow through a junction J-1. In some embodiments, junction J-1 can be a T. As illustrated, fluid addition station 5620 includes pump P-1 and valve V-1 in conjunction with a supply of different fluid (not shown) and can add that fluid to tube 5604. In some embodiments, a gas phase can be introduced between aqueous discrete volumes 5606. In some embodiments, an aqueous liquid can be added to aqueous discrete volumes 5606 in junction J-1. In some embodiments, the different aqueous fluid can be added a discrete volume between aqueous discrete volumes 5606. An aqueous discrete volume characteristic determination and optional manipulation station 5615, like 5614 and 5610 described above, follows liquid addition station 5620. In some embodiments, station 5615 evaluates the volume of liquid added to aqueous discrete volume 5606.

Next in line, as illustrated in FIG. 1C, is junction J-2. Junction J-2 and junction J-4, further down the line, fluidically connect back pressure unit 5616 to pressurize tube 5604 to a desired pressure. Between junctions J-2 and J-4, system 5600 includes a second processing section 5612, a junction J-3, at which point, fluid adding station 5622 can add a volume of liquid to pre-existing aqueous discrete volumes 5606, and an aqueous discrete volume characteristic determination and optional manipulation station 5617 can evaluate the volume of liquid added to aqueous discrete volume 5606.

As illustrated in FIG. 1C, system 5600 includes a final processing section 5612, and processed aqueous discrete volumes are delivered from tube 5604 to output station 5618. Examples of structures used in output station 5618 are described in concurrently filed U.S. patent application Ser. No. 11/507,733, now U.S. Pat. No. 9,285,297.

Immiscible-fluid-discrete-volumes deposited on multi-well plate 47 can be subjected to a sequencing reaction to form a detectable product, and the method of the present teachings can comprise detecting the detectable product. In various embodiments, the detectable product can be detected using, for example, a flow cell or a capillary electrophoretic sequencer. In various other embodiments, an off-capillary detector can be used as deemed appropriate.

FIG. 1C is yet another system for processing immiscible-fluid-discrete volumes downstream of the apparatuses, methods, and systems disclosed herein.

A simplified system 5600 is illustrated in FIG. 1C. As illustrated, box 5602 represents a structure that delivers to tube 5604 of system 5600 discrete volumes 5606 of aqueous liquid in a non-aqueous liquid 5608 with which they are immiscible. Examples of such structures and methods of generating discrete volumes 5606 in contact with spacing fluid 5608 are described herein. In some embodiments, such a structure could be a tube of preformed discrete volumes 5606 of aqueous fluid. In some embodiments, such a structure could be a chip or other substrate with a channel therein containing the discrete volumes 5606 of aqueous fluid. As illustrated, tube 5604 extends throughout system 5600. After entering tube 5604, desired information about aqueous volumes 5606 are determined and optionally manipulated by structures in triangle 5610. For example, the length and speed of a slug and the distance between two adjacent slugs can be desired information. In that example, a slug detection system can provide that information. If the distance between adjacent slugs does not meet preferred values, then additional spacing fluid can be added between the trailing point of the first slug and the leading point of the second slug, or one of the slugs could be held in an electric field, for example, to allow more of the existing spacing fluid to flow past it in tube 5603. If the length, and therefore the volume, of an aqueous discrete volume does not meet preferred values, additional non-reactive, miscible liquid can be added by an apparatus at that area of tube 5604. Triangle 5610 represents these and other structures of discrete volume characteristic detection and manipulation. Examples of these structures and/or component parts of thereof are described herein.

System 5600, as illustrated in FIG. 1C, next incorporates a processing section 5612 of tube 5604 (not illustrated, but in the box), which can include, for example, vibration, heating, cooling, and electromagnetic radiation exposure. In some embodiments, processing section 5612 can include thermal cycling between one or more pre-determined temperatures for pre-determined durations as needed, for example, to perform PCR, or other amplification methods. In some embodiments, aqueous discrete volumes may continue to flow at a constant rate through processing section 5612 while undergoing a desired process, or alternatively, they may dwell in a particular location in processing section 5612. System 5600, as illustrated in FIG. 1C, includes another aqueous discrete volume characteristic determination and optional manipulation station 5614. Aqueous discrete volumes 5606 then flow through a junction J-1. In some embodiments, junction J-1 can be a T. As illustrated, fluid addition station 5620 includes pump P-1 and valve V-1 in conjunction with a supply of different fluid (not shown) and can add that fluid to tube 5604. In some embodiments, a gas phase can be introduced between aqueous discrete volumes 5606. In some embodiments, an aqueous liquid can be added to aqueous discrete volumes 5606 in junction J-1. In some embodiments, the different aqueous fluid can be added a discrete volume between aqueous discrete volumes 5606. An aqueous discrete volume characteristic determination and optional manipulation station 5615, like 5614 and 5610 described above, follows liquid addition station 5620. In some embodiments, station 5615 evaluates the volume of liquid added to aqueous discrete volume 5606.

Next in line, as illustrated in FIG. 1C, is junction J-2. Junction J-2 and junction J-4, further down the line, fluidically connect back pressure unit 5616 to pressurize tube 5604 to a desired pressure. Between junctions J-2 and J-4, system 5600 includes a second processing section 5612, a junction J-3, at which point, fluid adding station 5622 can add a volume of liquid to pre-existing aqueous discrete volumes 5606, and an aqueous discrete volume characteristic determination and optional manipulation station 5617 can evaluate the volume of liquid added to aqueous discrete volume 5606.

As Illustrated in FIG. 1C, system 5600 includes a final processing section 5612, and processed aqueous discrete volumes are delivered from tube 5604 to output station 5618. Examples of structures used in output station 5618 are described in concurrently filed U.S. patent application Ser. No. 11/507,733, now U.S. Pat. No. 9,285,297.

According to various embodiments, the present teachings can encompass a resequencing method using system 10. In general, the resequencing method is similar to the de-novo method described herein with modifications as discussed herein.

In some embodiments, the pre-processing of a sample for resequencing comprises shearing a robust sample of nucleic acid having a plurality of copies of one or more nucleic acids of interest, herein also referred to as target sequences. The nucleic acids in the sample can be sheared. The method can comprise adding a plurality of sequence-specific primers to the sample before introduction to system 10, or the zip code primers can be added, at for example, at cross-intersection 10, to a set of immiscible-fluid-discrete-volumes generated from the sample. Immiscible-fluid-discrete-volumes made from the sample can contain a single copy of a nucleic acid fragment or can contain a plurality of copies of one or more different nucleic acid fragments. Each immiscible-fluid-discrete-volume can contain, for example, one forward primer and one reverse primer.

In some embodiments, the method can comprise moving a set of immiscible-fluid-discrete-volumes comprising the concentrations of primers discussed above, to thermal-cycler 74. The set of immiscible-fluid-discrete-volumes can be thermally cycled and thereafter processed in any of the many manners disclosed herein for the de novo sequencing method.

According to some embodiments, a method of the present teachings can comprise attaching zip code sequences to primers, for example, sequence-specific primers. Sequence-specific primers having zip code sequences attached thereto are referred to herein as zip tailed primers. A tailed primer can be a primer having an additional oligonucleotide attached thereto, for example, a zip code sequence, a universal sequence, or an ID tag sequence. Zip tailed primers can be more specifically referred to herein, as zip tailed forward primers and zip tailed reverse primers, depending on primer type. A pair of zip tailed primers used for amplifying a specific section of nucleic acid can have two different sequence-specific primer portions, and two different zip code sequences. The amplification of a specific target can be accomplished using a plurality of such pairs of zip tailed primers, for example a plurality of zip tailed forward primers complementary to a region upstream of the target nucleic acid, and a plurality of zip tailed reverse primers complementary to a region downstream of the target nucleic acid. The target sequences amplified may partially overlap. The partial overlap can insure complete target coverage. Primers corresponding to zip code sequences are referred generally to herein, as zip code primers. Primers corresponding to the zip code sequences of zip tailed forward primers are referred to herein, as forward zip code primers. Primers corresponding to the zip code sequences of zip tailed reverse primers are referred to herein, as zip code reverse primers. Nucleic acid amplification using zip code primers can result in the incorporation of zip code sequences into the amplified product. An amplified product having zip code sequences incorporated therein can reduce the number of specific primers needed for further amplification assays.

According to some embodiments, it can be convenient to designate a pair of zip code sequences as universal sequences. Universal sequences can be artificially designed sequences. Universal sequences can be designed to have essentially no homology with the target nucleic acids. Universal sequences can be designed to resist the formation of dimers among themselves (self-annealing). Universal sequences can be designed to bind with analogous primers with a consistent efficiency. Universal sequences can be selected based on their ability to resist mis-hybridization.

Universal sequences can be the same pair of sequences for each sample processed. The universal sequences of a pair of universal sequences can be designated as a forward universal sequence and a reverse universal sequence. A pair of primers corresponding to the pair of universal sequences can be designated as universal primers. More specifically, a pair of primers complementary to a forward universal sequence and a reverse universal sequence can be respectively designated as a forward universal primer and universal reverse primer. A nucleotide sequence comprising a sequence specific primer and a universal sequence can be designated as a universal tailed primer. More specifically, a nucleotide sequence comprising a sequence specific forward primer and a universal forward sequence can be designated as a universal tailed forward primer. Similarly, a nucleotide sequence comprising a sequence specific reverse primer and a universal reverse sequence can be designated as a universal tailed reverse primer. A nucleotide sequence comprising, a zip code sequence, and a universal sequence, is referred to herein as a universal tailed zip primer. A nucleotide sequence comprising a sequence specific forward primer, a zip code sequence, and a universal forward sequence is designated herein as a universal tailed zip tailed primer.

According to some embodiments, the method of resequencing can comprise adding a plurality of different zip tailed primers, for example, between about 50 and 150, different zip tailed primers, to each discrete volume of a set of immiscible-fluid-discrete-volumes. The set of immiscible-fluid-discrete-volumes can comprise a single sample divided into 100 discrete volumes. The zip tailed primers can be present in a relatively low (amplification limiting) primer concentration, for example, between about 1 nM and about 50 nM per zip tailed primer pair in each discrete volume. The zip tailed primers can comprise pairs of zip tailed primers, with each pair having two distinct zip code sequences, and two distinct primer sequences. The zip tailed primers can be designed to amplify a target nucleic acid. Alternatively, the plurality of zip tailed primers can be added to a larger volume of sample, and a PCR amplification can occur prior to creation of a set of immiscible discrete volumes. Using a single large volume to perform an initial PCR, the results of which are subsequently divided into a set of immiscible discrete volumes permits utilization of a minimum of gDNA.

In some embodiments the method of resequencing can comprise adding multiple copies of a unique pair of zip code primers to each discrete volume of a set. For example, each discrete volume can comprise multiple copies of a particular of pair zip code primers, with no two discrete volumes comprising the same pair of zip code primers. Each pair of zip code primers can correspond to the zip code sequences of a pair of zip tailed primers. The pairs of zip code primers can be present in an excess concentration relative to the concentration of the zip tailed primers, and each pair can function to amplify a target as determined by the specific pair of zip tailed primers. The concentration of the zip code primers can be from about 10 nM to about 1 micro M, or from about 100 nM to about 500 nM.

If large numbers of zip code primers are needed, as can be the case for large scale resequencing projects, the number of zip code primer pairs required scale up directly with an increase of the number of target areas of interest. Regardless of how the primer sets are added, the number to deal with can be an issue, and this can be particularly true if the primers are directly added to slugs, with one pump and/or conduit devoted to each primer set.

In some embodiments the present teachings comprise utilizing an M×N zip code primer configuration, which can reduce the number of reagents by 2*sqrt(n) relative to the number of zip code primers otherwise needed. For de novo sequencing the pre-amplification process can be substantially the same as described herein, except that instead of using zip tailed primer pairs, where the zip code sequence of each zip code primer of a pair is different from all others, zip code primers can re-used, as shown below. In order to prevent duplications of primer pairs, roughly half of the combinations cannot be used, for example AD is effectively a duplication of DA; one or the other can be used, but not both.

| M × N Zip code Primers 3' primer | | | | |
|---|---|---|---|---|
|  | A | B | C | D |
| A | AA | AB | AC | AD |
| B | BA | BB | BC | BD |

-continued

M × N Zip code Primers
3' primer

|  |  | A | B | C | D |
|---|---|---|---|---|---|
| 5' primer | C | CA | CB | CC | CD |
|  | D | DA | DB | DC | DD |

This process can permit an enormous reduction in the number of reagents needed, but can require two primer addition steps, (one zip code primer at a time, instead of both zip code primers as a pair), instead of the usual one primer addition step. The pairs of zip tailed primers used to incorporate zip code sequences into a target can be designed to have zip code sequences that correspond to the zip code primer combinations as shown above. In this way, only the intended target sequences will be amplified to any significant amount.

The method for resequencing can comprise amplifying the set of immiscible-fluid-discrete-volumes through, for example, between about 20 and 50 cycles of amplification. The method can comprise processing a set of immiscible-fluid-discrete-volumes through shrimp alkaline phosphatase and exonuclease, followed by incubation, and sequencing amplification, as discussed above, relating to the de novo sequencing method.

Figure 2A:
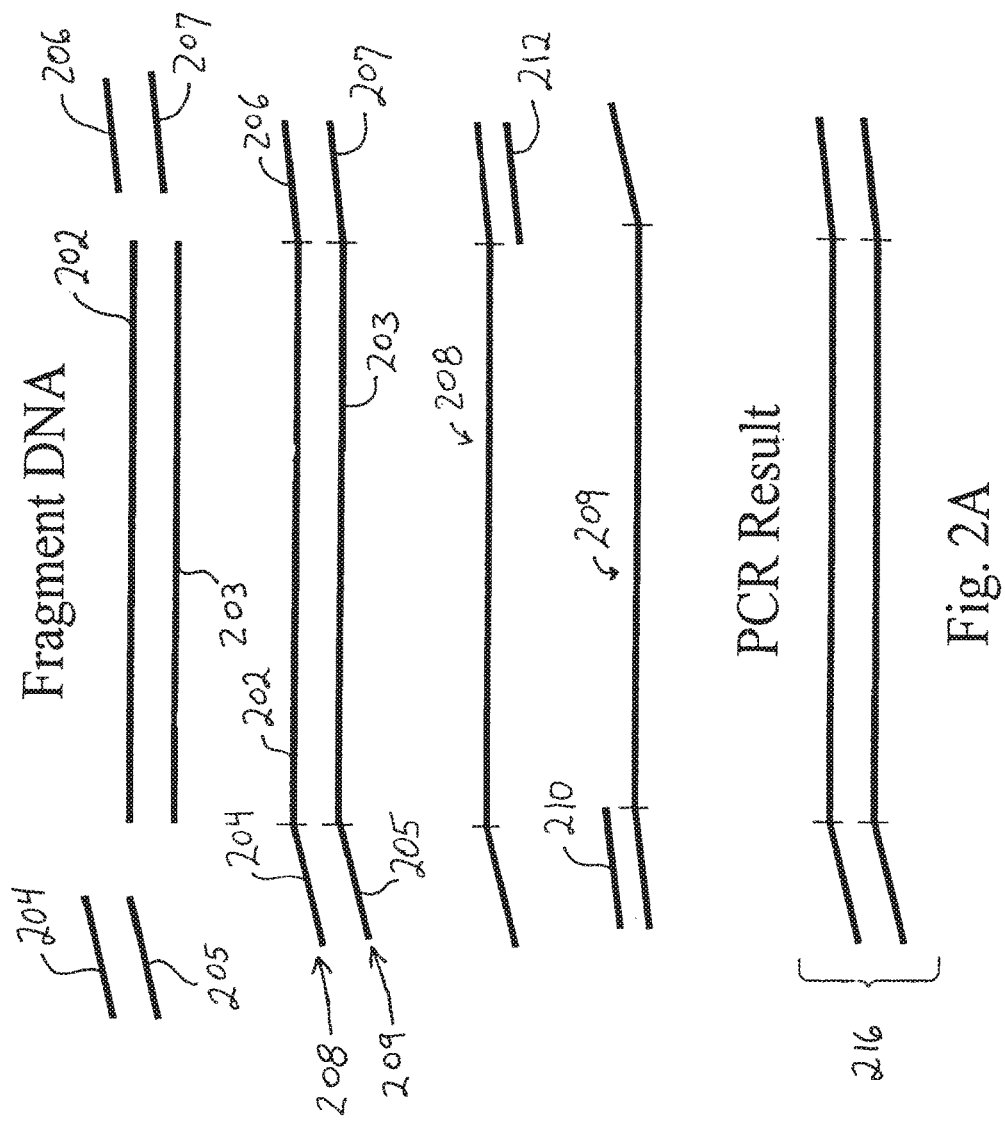
FIGS. 2A-2B depict various cycles and the results thereof, of de novo sequencing reactions according to various embodiments.
Figure 2B:
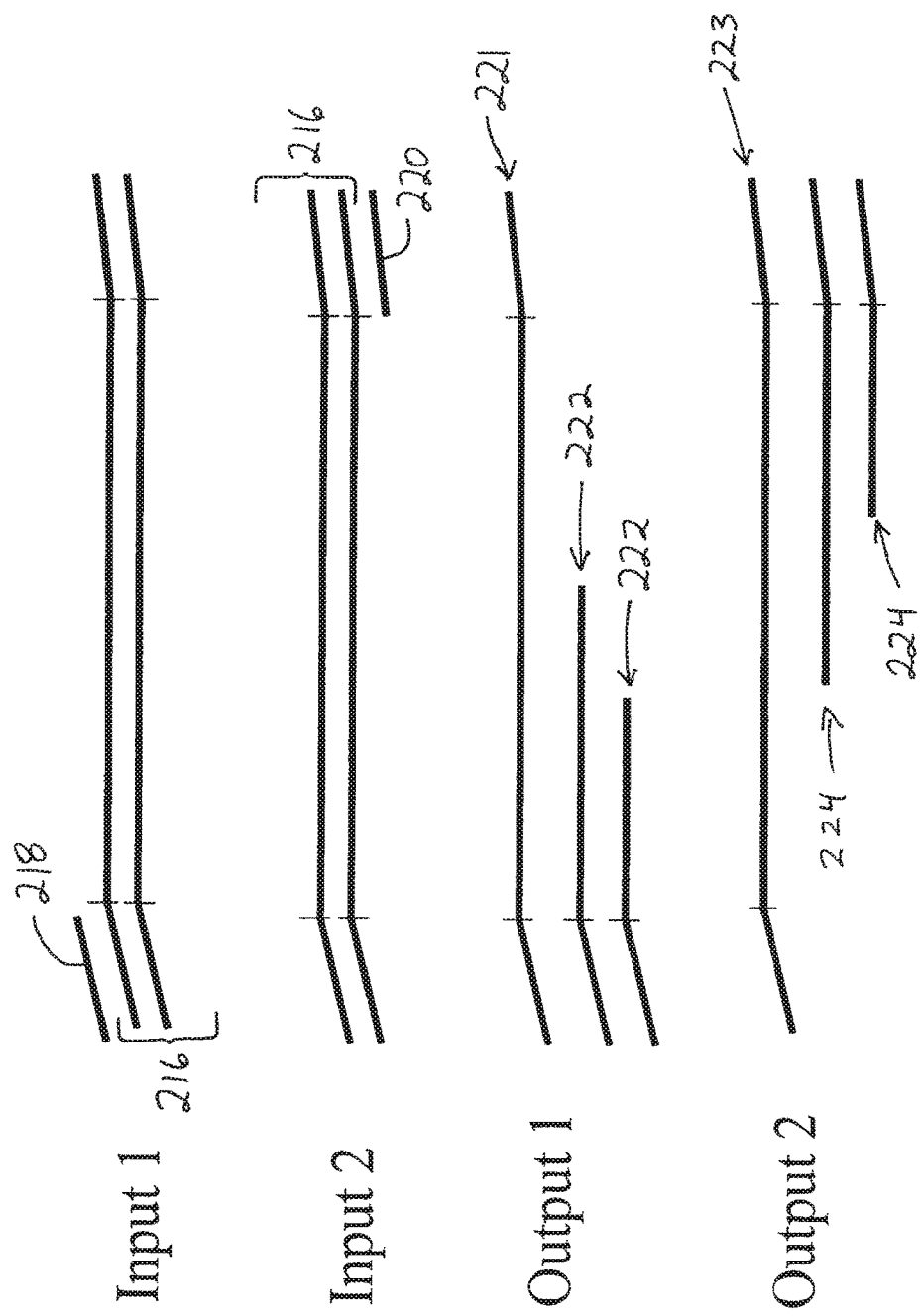

According to various embodiments, and as illustrated in FIGS. 2A and 2B the present teachings can comprise a de novo sequencing method. The method can comprise shearing sample, for example gDNA, and then diluting the gDNA. The diluted sample can be added to a plurality of discrete volumes, for example a set of immiscible-fluid-discrete-volumes, such that only one fragment of nucleic acid is present per discrete volume. The following description applies to one discrete volume, but the disclosed method can be practiced on a plurality of discrete volumes. Universal sequences can be added to the discrete volume. For example, universal sequence 204 and its complementary strand 205, and universal sequence 206, and its complementary stand 207, can be added to a discrete volume comprising a nucleic acid fragment 202, and its complementary strand 203. Universal sequences 204 and 206 can be ligated to the ends of fragment 202, thereby forming a universal tailed fragment 208. Universal sequences 205 and 207 can be ligated to the ends of fragment 203, thereby forming a universal tailed fragment 209.

According to some embodiments, universal primers 210 and 212 can be added to the discrete volume. The discrete volume can be thermally cycled and universal primers 210 and 212 can anneal to complementary strands that were previously ligated. Universal primer 212 is shown annealed to universal tailed fragment 208. Universal primer 210 can anneal to tailed fragment 209.

According to various embodiments, universal primers 210 and 212 can be used to amplify universal tailed fragments 208 and complementary fragment 209 thereby resulting in amplicon 216. Amplicon 216 can comprise a copy of tailed fragment 208 and a complementary strand thereto. In all of the amplification reactions recited herein, it is implied that ordinary amplification reagents are present during the reaction, and only differing reagents are noted.

According to various embodiments, after multiple rounds of amplification a discrete volume comprising a plurality of double stranded amplicon 216 molecules, can be split and moved into an Input 1 and an Input 2 (FIG. 2B). Input 1 can be flowed into a forward sequencing conduit (not shown). Input 2 and each can be flowed into a reverse sequencing conduit (not shown). A universal forward primer 218 and sequencing reagents (not shown) can be added to Input 1. A universal reverse primer 220 and sequencing reagents (not shown) can be added to Input 2. Input 1 and Input 2 can be thermally cycled to perform a Sanger sequencing reaction and then moved out of their respective sequencing conduits as an Output 1 and an Output 2, respectively. Output 1 can comprise a plurality of forward sequencing fragments 222. Output 2 can comprise a plurality of reverse sequencing fragments 224. Sequencing fragments 222 and 224 can be labeled with, for example, labeled chain terminating ddNTPs. Sequencing fragments can be read on, for example, a CE analyzer or the like. In all of the embodiments requiring a sequencing reaction, it is implied that ordinary sequencing reagents are present during the reaction, and only differing reagents are noted.

Figure 2C:
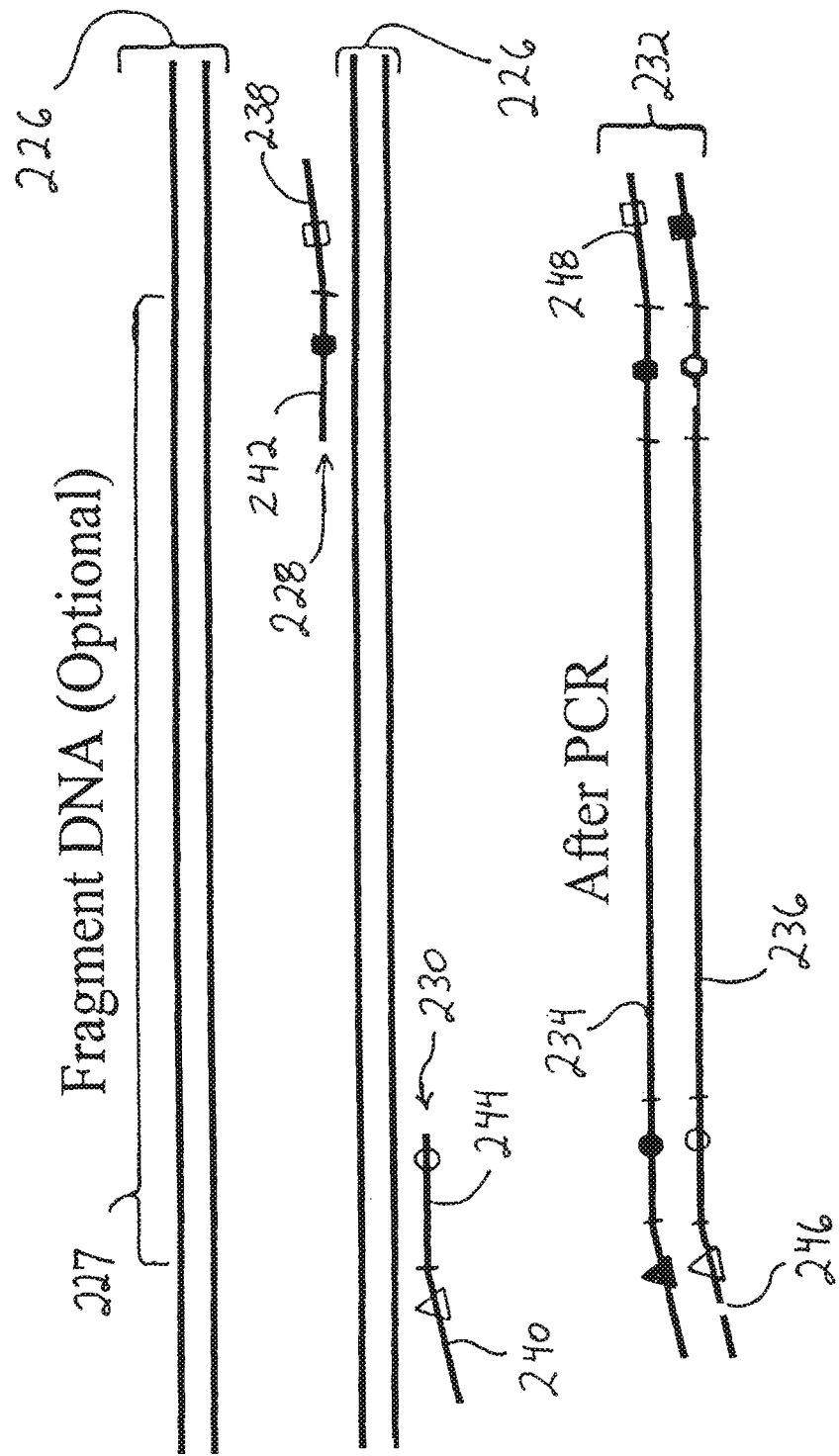
FIGS. 2C-2D depict various cycles and the results thereof, of standard resequencing reactions according to various embodiments.
Figure 2D:
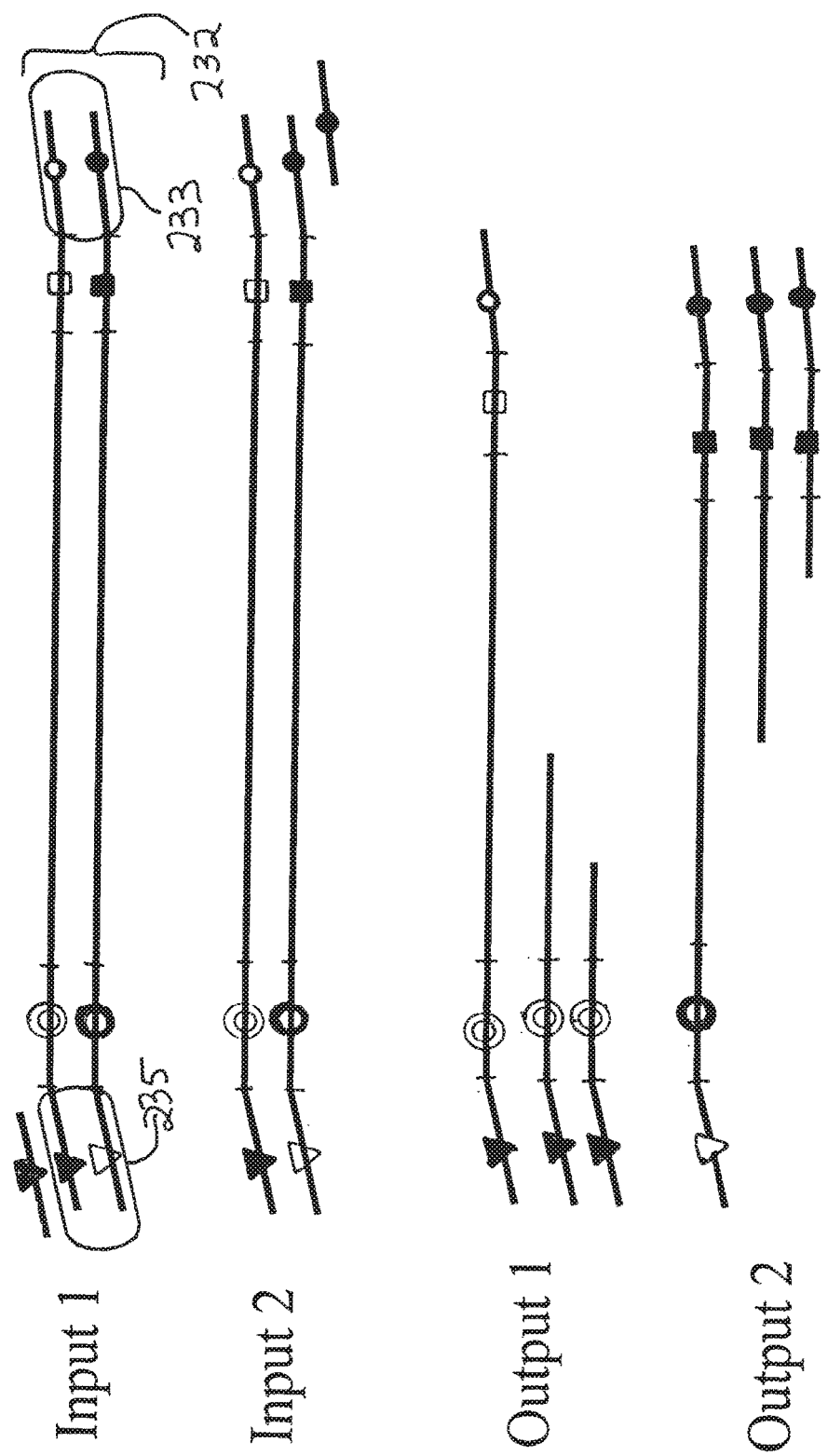

According to some embodiments, FIGS. 2C and 2D illustrate a method of resequencing. The method can comprise adding a sample 226, to a plurality of discrete volumes. The sample 226 can be a nucleic acid sample and can optionally be a sheared. Sample 226 can comprise a target sequence 227 A discrete volume can comprise a plurality of nucleic acid samples, and/or a plurality of nucleic acid sample fragments. Universal tailed primers 228 and 230 can be added to sample 226, along with nucleic acid amplification reagents. Universal tailed primer 228 can comprise a sequence specific forward primer 242 and a forward universal sequence 238. Universal tailed primer 230 can comprise a sequence specific reverse primer 244 and a reverse universal sequence 240. The discrete volume can be thermally cycled, and target sequence 227 amplified.

In some embodiments, after thermally cycling, the discrete volume can comprise an amplicon 232. Amplicon 232 can comprise a forward universal sequence 248, and a reverse universal sequence 246, that are respective copies of forward universal sequence 238, and a reverse universal sequence 240. Amplicon 232 can comprise a target sequence 234 and its complementary sequence 236, which can be copies of a portion of sample 226.

According to various embodiments, FIG. 2D illustrates a sequencing reaction method for amplicon 232. The method is similar to the method described in FIG. 2B. A difference between the method of FIG. 2B and the method of FIG. 2D is that universal sequences 233 and 235 of amplicon 232 were incorporated through the previous amplification reaction, rather than through ligation, as disclosed in FIG. 2A. Otherwise, similar output template sequences and sequencing fragments result as show in the method of FIG. 2B.

Figure 2E:
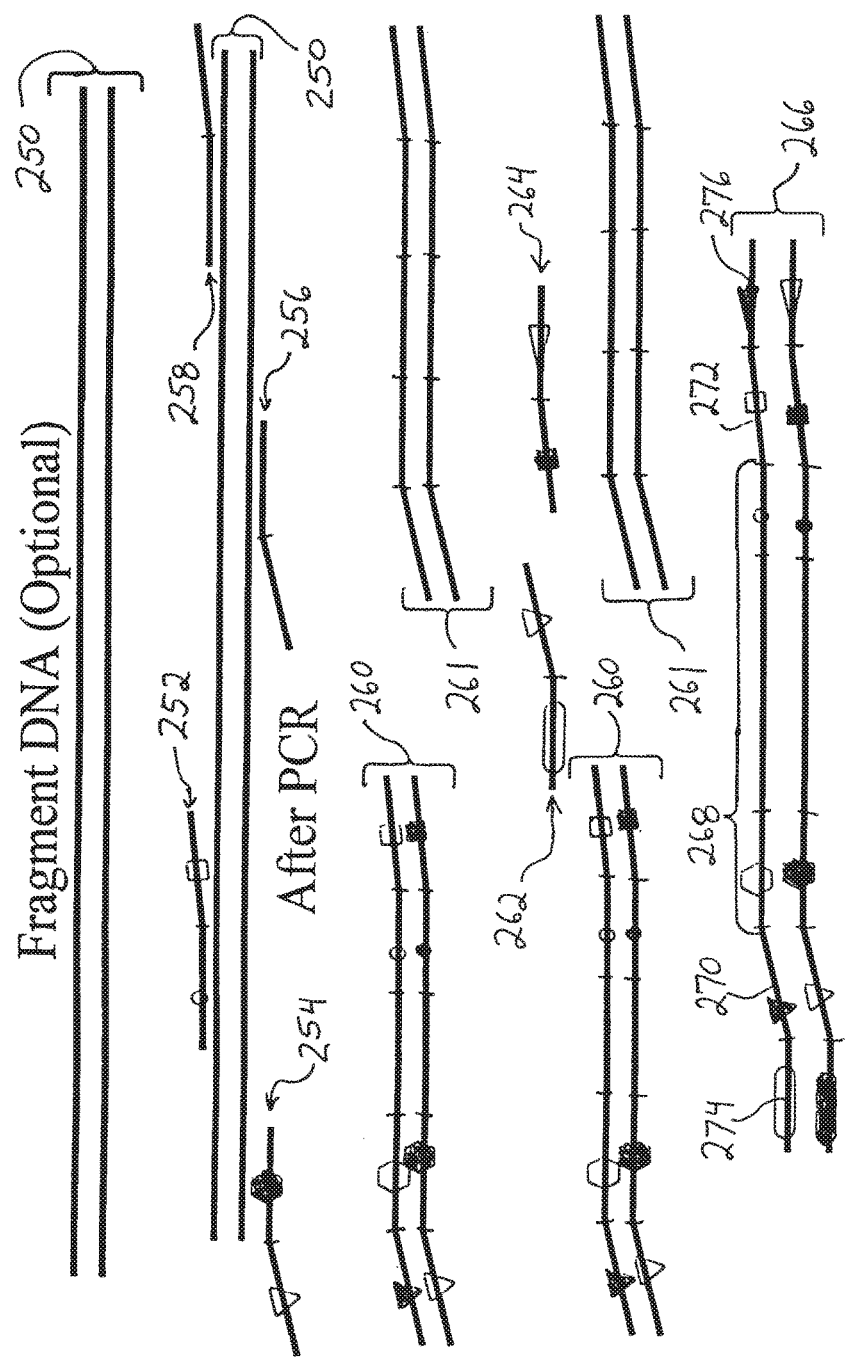
FIGS. 2E-2F depict various cycles and the results thereof, of zip code resequencing reactions according to various embodiments.

According to some embodiments, FIG. 2E illustrates a modification of a resequencing method wherein zip code sequences are incorporated into the amplicons in addition to universal sequences. The method comprises obtaining more than one nucleic acid molecule 250, or fragments thereof. Nucleic acid 250 can be disposed in a discrete volume, or the like. A plurality of pairs of zip tailed primers can be added to nucleic acid 250. For example, a first pair of zip tailed primers 252 and 254, and a second pair of zip tailed primers 256 and 258 can be added to nucleic acid 250. The two pairs of primers can be used to amplify two different target sections of the same nucleic acid molecule 250, during, for example, a nucleic acid amplification reaction.

According to some embodiments, nucleic acid amplification will result in amplicons containing a target sequence flanked by zip code sequences, and a complementary strand thereto. For example, amplicons 261 can comprise a target sequence from nucleic acid molecule 250, and zip code sequences from zip tailed primers 256 and 258. A second type of amplicon 260 generated from zip tailed primers 252 and 254, is also shown.

In some embodiments, pairs of universal tailed zip code primers can be added to the amplicons from the previous amplifications. Universal tailed zip code primers can comprise a zip code sequence that is corresponds to one of the zip code sequence previously incorporated into an amplicon. Universal tailed zip code primers can comprise a universal sequence. Amplifying amplicon 260 using universal tailed zip code primers 262 and 264 can result in an amplicon 266. Amplicon 266 can comprise a target sequence 268 that is flanked by two zip code sequences 270 and 272, which in turn are flanked by two universal sequences 274 and 276, and a sequence complementary thereto.

Figure 2F:
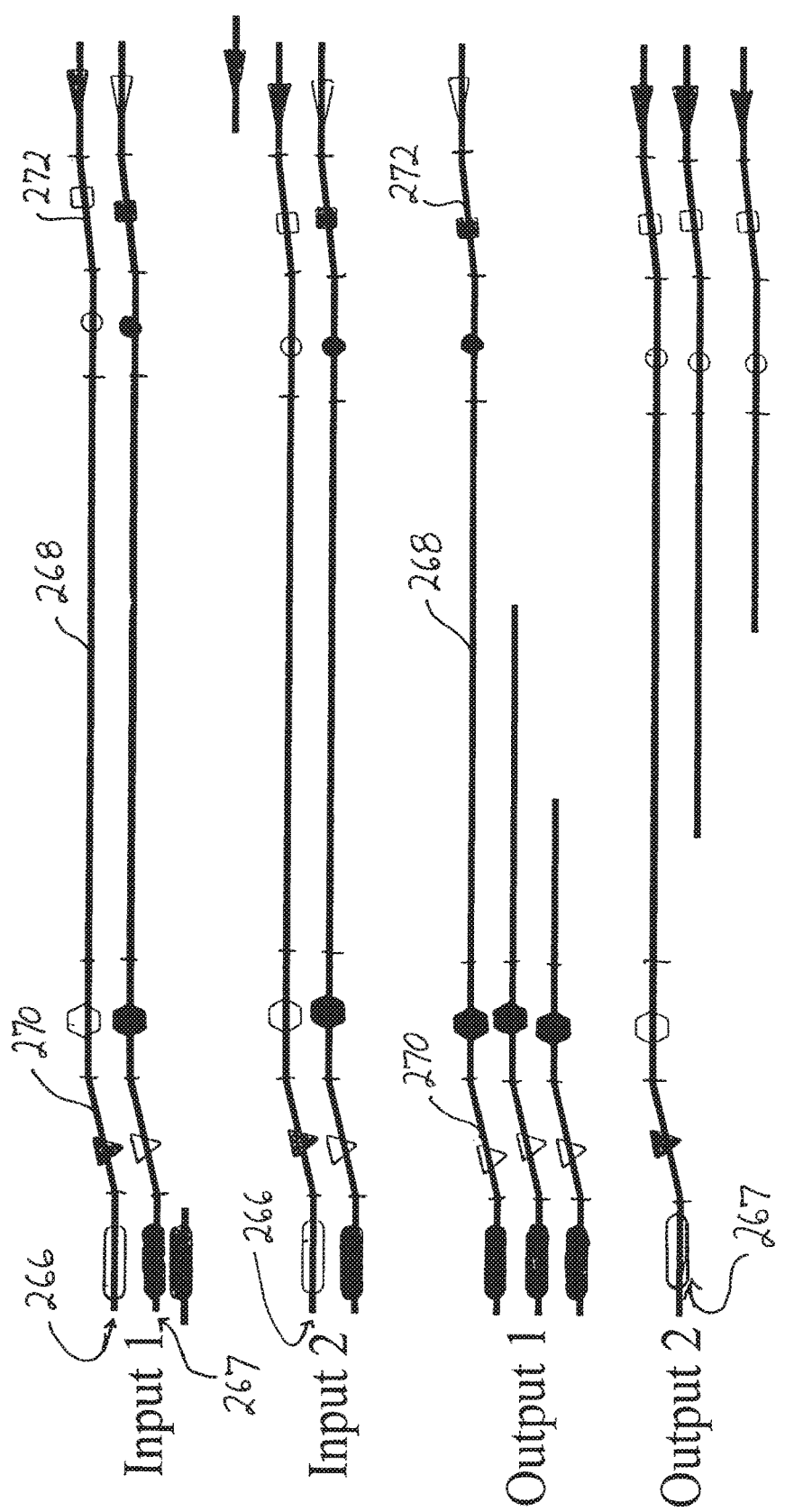

According to various embodiments, and as illustrated in FIG. 2F, a discrete volume containing a plurality of copies of amplicon 266 can be split and sequenced in a method similar to that described with reference to FIG. 2B. A difference between the previous methods is that amplicon 266 comprises zip code sequences flanking the target sequences. The zip code sequences will be present in every sequencing product.

Figure 2G:
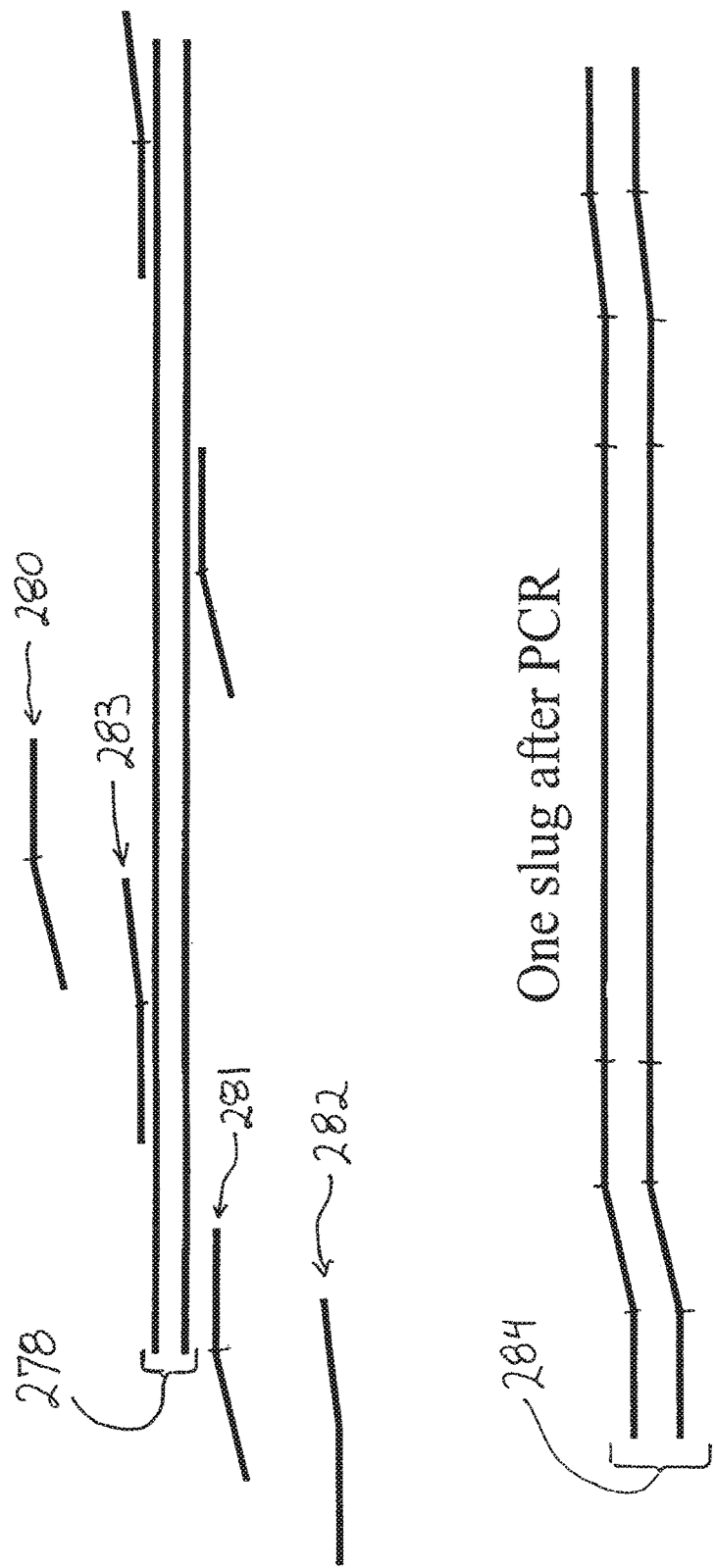

According to some embodiments, and as illustrated in FIG. 2G, the incorporation of zip code sequences and universal sequences, as shown in FIG. 2E, can be accomplished in a single multiplexed step. As shown, a pair of zip tailed primers 281 and 283 can be added to a sample of nucleic acid 278. Multiple pairs of zip tailed primers specific to other sequences of sample 278 can also be added, but only a method involving zip tailed primers 281 and 283 will be detailed herein. In addition, a pair of universal tailed zip code primers can also be added to sample 278. The resulting sample fluid can be amplified through multiple rounds of amplification. The first few rounds of amplification can result in the incorporation of zip code sequences into the resulting amplicons. The zip code sequences can flank the target sequences of the amplicons. In later rounds of amplification, universal sequences will be incorporated onto the amplicon. The universal sequences can flank the zip code sequences. The universal sequences can be incorporated by amplification with universal tailed zip code primers. Zip tailed primers 281 and 283 can be present in lower concentrations than the universal tailed zip code primers. This difference in concentration can facilitate the incorporation of the universal sequences into amplicon 284, in the later rounds of amplification. The correspondence between the zip code sequences of the zip tailed primers and the zip code sequences of the universal tailed zip code primers, insures that amplicon 284 comprises both zip code sequences and universal sequences, in addition to a target sequence.

In some embodiments multiple discrete volumes each comprising a sample and multiple different pairs of zip tailed primers specific to multiple target sequences, can be produced. To each discrete volume a plurality of one pair of universal tailed zip code primers can be added, such that each discrete volume has multiple copies of a single pair of universal tailed zip code primers, with the pairs being different for each discrete volume. The pairs of universal tailed zip code primers can be designed to amplify a single target sequence that is flanked with particular zip code sequences. The flanking zip code sequences can be complementary to the zip code sequences of the pair of universal tagged zip code primers.

According to various embodiments, and as illustrated in FIG. 2H, amplicon 284 can have a cycle sequencing reaction performed using the sequencing method described in FIG. 2F.

Figure 2I:
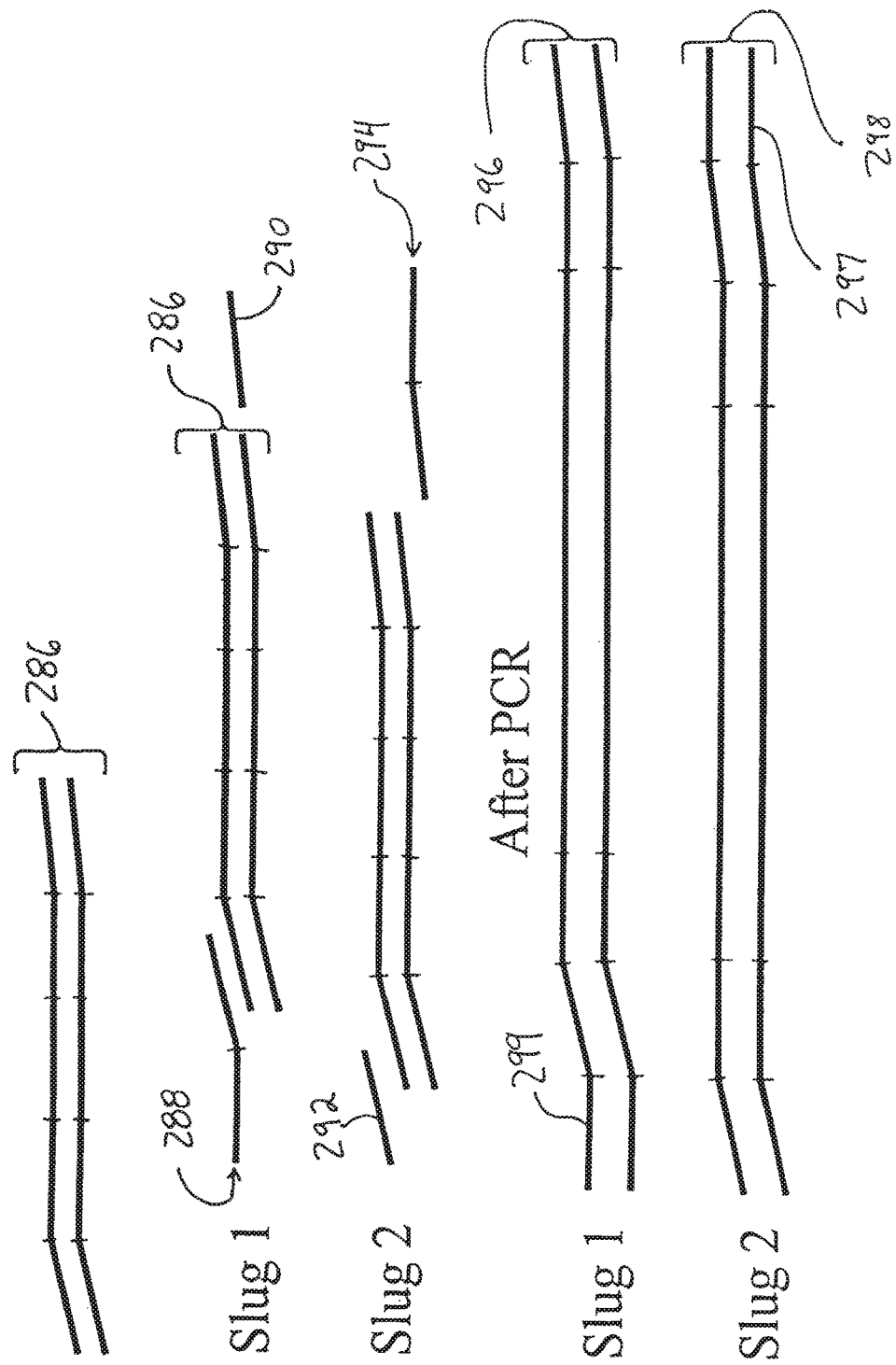
FIGS. 2I-2J depict various cycles and the results thereof, combined resequencing reactions according to various embodiments.

According to some embodiments, and as illustrated in FIG. 2I, a discrete volume comprising a plurality of amplicon 286 can be divided into Slug 1 and Slug 2. Amplicon 286 can comprise a target sequence flanked by zip code sequences, and a complementary strand thereto. A universal tailed zip code forward primer 288, and a reverse zip code primer 290, can be added to Slug 1. A universal tailed zip code reverse primer 294, and a forward zip code primer 292, can be added to Slug 2. Slugs 1 and 2 can be thermally cycled to produce amplicon 296 in Slug 1, and amplicon 298 in Slug 2. Amplicon 296 can comprise forward universal sequence 299. Amplicon 296 can comprise reverse universal sequence 297. According to some embodiments, universal sequences 297 and 299 can be the same sequence.

Figure 2J:
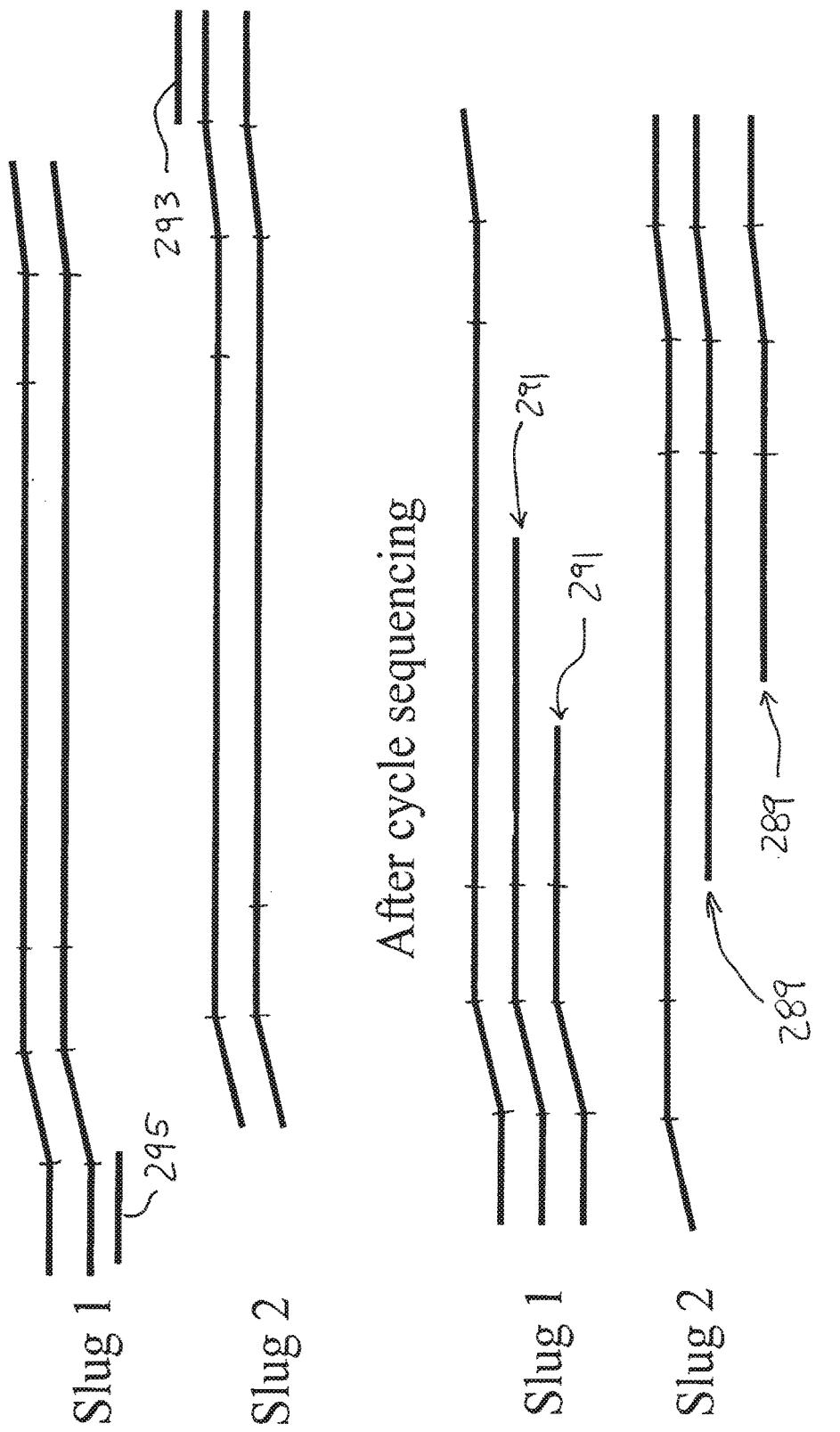

According to some embodiments, and as illustrated in FIG. 2J, a universal forward primer 295, can be added to Slug 1. A universal reverse primer 293, can be added to Slug 2. Slugs 1 and 2 can undergo sequencing reactions resulting in the generation of forward sequencing fragments 291, in Slug 1, and reverse sequencing fragments 289, in Slug 2. According to some embodiments, universal primers 293 and 295 can be the same sequence.

According to some embodiments, a variation to the method illustrated in FIG. 2J, a universal forward primer 295, and universal reverse primer 293, can both be added to both Slug 1, and Slug 2. Slugs 1 and 2 can undergo sequencing reactions resulting in the generation of forward sequencing fragments 291, in Slug 1, and reverse sequencing fragments 289, in Slug 2.

Figure 2K:
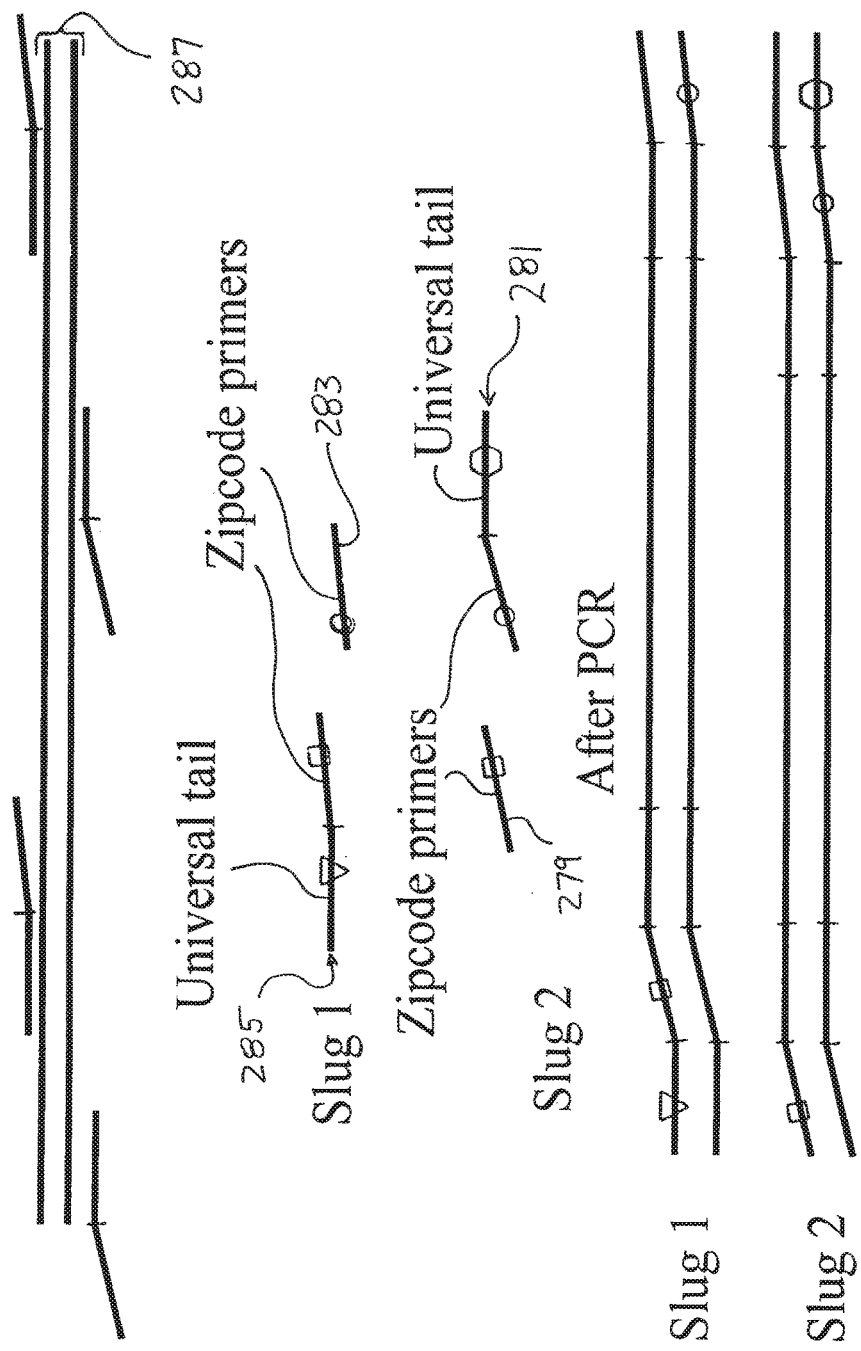
FIG. 2K depicts various cycles of combined resequencing reactions according to various embodiments.

According to various embodiments, and as illustrated in FIG. 2K, the method of FIG. 2G can be expanded to include a plurality of targets from a nucleic acid sample 287. A plurality of slugs can be created, each comprising a plurality of nucleic acid targets, and a plurality of pairs of zip tailed primers (not shown). Each pair of zip tailed primers can be specific to one target sequence. The slugs can be thermally cycled resulting in a plurality of amplicons comprising target sequences flanked by zip code sequences. After amplification, one type of universal tailed zip code primer, and one type of zip code primer, can be added. For example, to Slug 1 can be added a particular type of universal tailed zip code forward primer 285, and a particular type of zip code reverse primer 283, both of which can be specific for a particular amplicon. Similarly, to slug 2 can be added a particular type of universal tailed zip code reverse primer 281, and a particular type of zip code forward primers 279, both of which are specific to portions of a complementary strand to the amplicon of Slug 1. The contents of Slugs 1 and 2 can be amplified, and the resulting amplicons can be sequenced according to the method of FIG. 2J. Optionally, in some embodiments, a single amplification can be performed after the addition of the universal tailed zip primers and the zip code primers, as described regarding FIG. 2G.

According to some embodiments, additional slugs can be made for each target sequence, with specifically designed universal tailed zip code primers, and zip code primers being added thereto.

According to some embodiments, a method can comprise tracking individual discrete volumes of a set of immiscible-fluid-discrete-volumes when performing resequencing. Tracking can be accomplished by tracking the location of each discrete volume as it progresses through system 10. Tracking can be accomplished by recording where each discrete volume is output into the wells of a multi-well plate. In some embodiments oligonucleotide sequence tags can be embedded in the samples of a discrete volume, such that the embedded sequences will appear in the sequence information generated by the resequencing method.

In some embodiments, identification oligonucleotide sequence (ID) tags of can be incorporated into sample oligonucleotides in an immiscible-fluid-discrete-volume. The actual sequences of the ID tags can be generally shorter than zip code sequences. ID tag sequences need not function as sites for primer annealing. For example, an ID tag can be a random assortment of between about 3 and 8 nucleic acid bases of random assortments of the 4 nucleotide bases. ID tags can be specifically assigned to a target sequence, or can be used for a number of target sequences from a single sample ID tags can be used alone, or in conjunction with zip code sequences. ID tags can be used to distinguish between different reactions using the same two zip code primer sequences. ID tags can be used to distinguish two different samples. An ID tag can be ligated to the 5' end of a sample oligonucleotide or, for example, the ID tag can be ligated directly to the 5' end of a sample comprising a zip code sequence, such that the ID tag is ligated directly to the zip code sequence.

According to various embodiments, an ID tag can be ligated to the 5' end of a tailed primer. This can be accomplished using T4 ligase in a manner similar to ligating a zip code sequence to a nucleic acid sample, as described above. The ligation can be performed on both members of a pair of zip tailed primers used for amplifying a specific section of nucleic acid. The ligation can be performed on one member of a pair of zip tailed primers used for amplifying a specific section of nucleic acid.

In some embodiments, it may be beneficial to reduce unwanted nucleic acid amplification side reactions when ligating oligonucleotides. The reduction of side reactions can be accomplished by using a splint comprising an oligonucleotide. A splint can have an unextendable 3' end. The 3' end of a splint can be made unextendable by, for example, 3' dideoxymodification, 3' amino modification, or the like. The splint can also be made to be unextendable by incorporating dU residues therein, followed by treatment with uracyl-DNA-glycosylase prior to nucleic acid amplification. In other embodiments, the reduction of side reactions can be accomplished by using an ID tag designed to form a hairpin structure. In some embodiments both a splint and a hairpin structure can be used.

Figure 3A:
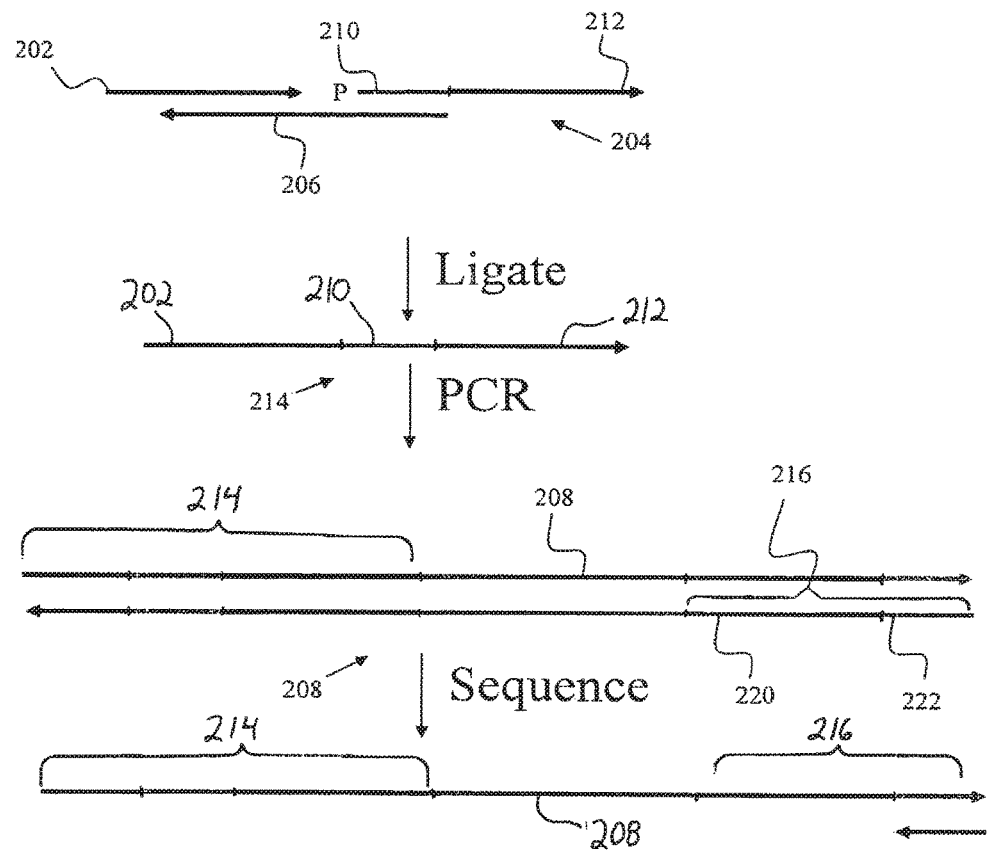
FIG. 3A illustrates a method of ligating an ID tag to a tailed forward primer, using a splint, and then the subsequent amplification and sequencing of an oligonucleotide of interest.
Figure 4:
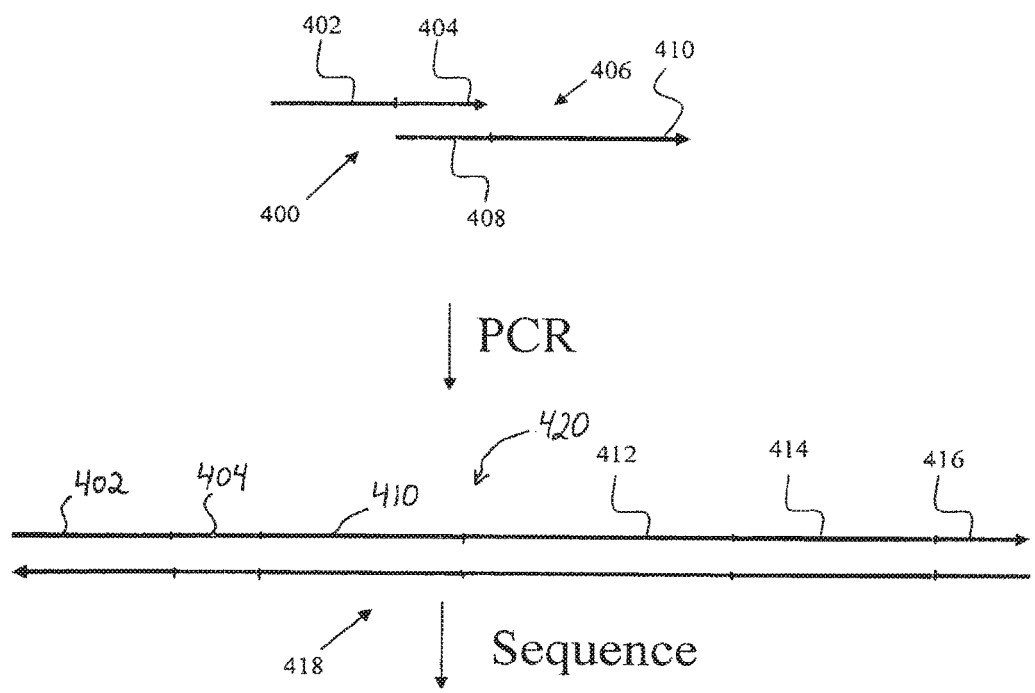
FIG. 4 depicts a method of incorporating an ID tag into an oligonucleotide without using ligation step.
Figure 5:
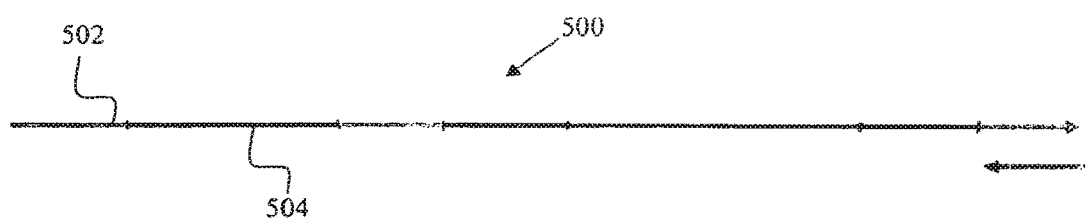
FIG. 5 depicts enhancing the determining of the nucleic acid sequence of the 3' end of an amplified product by adding a spacer sequence to the 3' end of and ID tag.

FIG. 3A illustrates a method of ligating an ID tag 302, to a tailed forward primer 304, using a splint 306, and then the subsequent amplification and sequencing of a target region 308 of interest. In FIGS. 3-5, the arrows indicate 5' to 3' orientation of the DNA strand. Tailed forward primer 304 can comprise a forward universal sequence 310, and a forward primer 312. Tailed forward primer 312 can be specific to a target nucleic acid sequence. Tailed forward primer 304 can be a VariantSEQr primer, from Applied Biosystems, Foster City Calif. Splint 306 can comprise a nucleic acid sequence that has a first portion that is complementary to at least a portion of ID tag 302, and a second portion that is complementary to at least a portion of tailed forward primer 304.

The annealing of splint 306 to both ID tag 302, and tailed primer 304, can function to position the 3' end of ID tag 302 adjacent to the 5' end of tailed forward primer 304. In this way, ID tag 302, and tailed primer 304, can be properly ligated, thereby forming an ID tailed forward primer 314, comprising ID tag 302, universal forward sequence 310, and forward primer 312.

A plurality of ID tailed forward primers 314 can be added to one or more immiscible-fluid-discrete-volumes of a set of immiscible-fluid-discrete-volumes, the following methods can be practiced therein. The immiscible-fluid-discrete-volumes can comprise one or more target nucleic acids. In addition, a tailed reverse primer 316, comprising a universal reverse tail 322, and a reverse primer 320, that is specific to a target nucleic acid sequence, can be can be introduced into the one or more immiscible-fluid-discrete-volumes. In some embodiments tailed reverse primer 316 can comprise an ID tag (not shown) that is different from the ID tag of ID tailed forward primer 312. In some embodiments, tailed reverse primer 316 can comprise an ID tag (not shown) that is the same as the ID tag of ID tailed forward primer 312. Reverse primer 320 can be complementary to a different portion of the same target nucleic acid, usually on a different side of the target nucleic acid. In addition other suitable nucleic acid amplification reagents can be added, as needed.

The discrete immiscible-fluid-discrete-volumes can be amplified in a nucleic acid amplification reaction, for example a PCR or RT-PCR reaction. The product of the amplification reaction can be an oligonucleotide comprising a nucleic acid sequence corresponding to ID-tagged tailed forward primer 314, target nucleic acid 308, tailed reverse primer 316, and a complementary oligonucleotide thereto. After amplification, the amplified product can be sequenced as described below. An ID sequence can be used in conjunction with short target sequences, as this permits the sequencing of the entire target sequence and the ID tag, which is read after the target sequence.

Figure 3B:
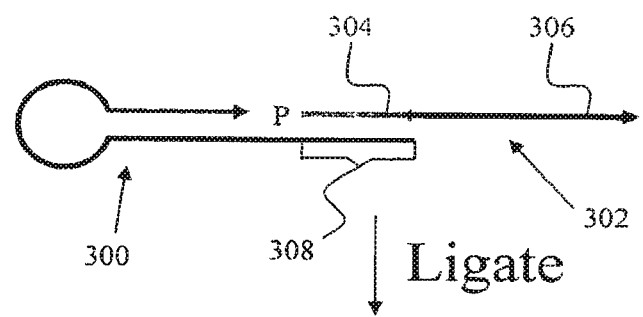
FIG. 3B illustrates an ID tag that can comprise a sequence of nucleic acids that can form a hairpin loop structure.

According to some embodiments, FIG. 3B illustrates an ID tag 330 that can comprise a sequence of nucleic acids that can form a hairpin loop structure. The hairpin loop can arise from complementary bases within ID tag 330, annealing to one another. ID tag 330 can be ligated to a tailed forward primer 332. Tailed forward primer 332 can comprise a universal forward sequence 334, and a target specific forward primer 336. ID tag 330 can comprise an extension oligonucleotide 338, which can be complementary to universal forward tail 334. Annealing extension oligonucleotide 338, to universal forward tail 334, can position the 3' end of ID tag 330 adjacent to the 5' end of tailed forward primer 332, and thus in a suitable position for ligation. ID tag 330 can be used in place of the ID tag 302 and splint 306 in the above recited method.

According to some embodiments, and as illustrated in FIG. 4, the present teachings can comprise a method of incorporating an ID tag into an oligonucleotide without a ligation step. The method can comprise providing an ID-tagged forward primer 400 comprising an ID tag 402, and a forward universal primer 404. The method can comprise providing a tailed forward primer 406 comprising a forward universal sequence 408, and a forward primer 410 that is specific to a target nucleic acid sequence. Forward universal sequence 408 can be complementary to forward universal primer 404.

According to various embodiments, the method of incorporating an ID tag can comprise a nucleic acid amplification reaction using universal tailed target specific forward primer 400 in conjunction with ID-tagged universal forward primer 406. ID-tagged universal forward primer 406 can be present in a higher concentration than tailed forward primer 400. As the number of amplification cycles increases, ID-tagged forward primer 406 can take over the reaction and serve as the primer for the amplification reaction. The amplification can result in an amplified product 420. Amplified product 420 can comprise ID tag 402, forward universal primer 404, a forward primer 410, a target sequence 412, a reverse primer 414, an ID tag 416 of a different sequence, and an oligonucleotide 418, complementary thereto. Reverse primer 414 and ID tag 416, are incorporated from an ID-tagged reverse primer (not shown) used in the reaction.

According to various embodiments, the products of the above methods of incorporating an ID tag can be sequenced. Sequencing can be achieved by conducting a sequencing amplification reaction followed by reading the results of the amplification, for example, in a CE analyzer.

According to some embodiments, and as illustrated in FIG. 5, determining the nucleic acid sequence of the 3' end of an amplified product 500 can be enhanced by adding a spacer sequence 502 to the 3' end of and ID tag 504. Spacer sequence 502 can be added to the 3' end of an ID-tagged forward primer. Spacer sequence 502 can improve the robustness of sequencing determination by moving ID tag further from the 3' end of an amplified product. The spacer sequence can permit the reading of an entire ID tag sequence before reading aberrations that occur at the end of a CE run, due to the presence of full length unlabeled amplicons from previous amplification steps.

According to some embodiments the present system can be used for genotyping. One example of genotyping is the analysis of short tandem repeats (STRs). This can be performed by PCR amplifying a region that contains a variable number of short repeats across individuals. By labeling one or both PCR primers, the PCR products can be detected using CE instruments, and the sizes of the repeat region can be measured. PCR could be performed in the discrete volumes created by the present system. Two or more STR's can be analyzed by changing the color of the dye, or by changing the size range of the amplicon. All STR loci can be amplified in a multiplex PCR reaction, or each locus can be amplified separately, then combined into one well for CE injection. Examples of products the can be used to analyze STRs include StockMarks® Animal Genotyping System, the Human Linkage Mapping Sets, and the AmpFISTR® Human DNA Identification Kits, all from Applied Biosystems, Foster City, Calif.

In other embodiments, genotyping can include the analysis of single nucleotide polymorphisms (SNPs). This can be performed by single base extension assays. This approach involves annealing a primer to the sample (which is often a PCR amplicon covering the locus of interest) and adding polymerase and all 4 labeled ddNTPs. The primer can be designed so that its 3' end is one base away from the polymorphism. The polymorphic base can be identified by the fluorescent emission color of the single base extension product. By making the primer extension products different sizes, it is possible to analyze more than one locus per CE lane. Any or all of the following steps could be done in the present system: PCR amplification of the locus, PCR cleanup with SAP/exo, primer extension. With the present system, one could perform individual PCR reactions in slugs, optionally SAP/exo treat them, then combine the amplicons into a single volume for multiplex single base extension. For, example, the SNaPshot® Multiplex System for single base extension reactions, from Applied Biosystems, Foster City, Calif., could be used.

According to some embodiments, the present teachings make use of the findings that human DNA contains both normal cytosine (C) and 5-methyl cytosine. Normal cytosine can be converted into 5-methyl cytosines by enzymes that methylate the C's in the sequence context 5' . . . CG . . . 3' (referred to as a CpG dinucleotide). Generally, CpG methylation is believed to involve all or most of an entire region, and specifically the promoter region(s) of genes. The presence of a higher than the stastically average number of CpG's in a given sequence is known as a CpG island. The methylation of all or most of a CpG island can correlate with the loss of gene expression. Additionally, there are examples of methylation in non-CpG islands, or even in single CpG dinucleotide, where methylation can inhibit gene expression. The precise location of all of the methylated cytosines in a region, and both the location and the degree of the methylation is believed to be important. The degree of methylation is believed to correspond to the progression of the loss of green expression and correlates to the presence of chronic diseases, such as cancer. Methylation analysis is potentially a valuable diagnostic tool for health monitoring. Diet (life-style changes) as well as chemical intervention can change methylation status, and possible reverse health problems.

According to various embodiments, bisulfite conversion of DNA can be a useful technique for the analysis of methyl C modification. Applied Biosystems has improved the bisulfite conversion leading to several patent applications, (especially 60/499,082 filed on Aug. 23, 2003, and 60/523, 056 filed on Nov. 17, 2003) and the following publication: Boyd et al., *Bisulfite conversion of genomic DNA for methylation analysis: protocol simplification with higher recovery applicable to limited samples and increased throughput*, Anal Biochem Vol. 326 (2004) pp. 278-280, all of which are incorporated herein, in their entireties, by reference. Once converted, a range of techniques have been developed to analyze the DNA. These techniques include: methyl-specific PCR, see, Herman et al., *Methylation specific PCR: a novel PCR assay for methylation status of CpG islands*, Proc. Nat'l. Acad. Sci. U.S.A. Vol. 93 (1996), pp. 9821-9826; Methylation-sensitive single nucleotide primer extension (Ms-SNuPE), see Gonzalgo, et al. *Rapid quantitation of methylation differences at specific sites using methylation-sensitive single nucleotide primer extension (Ms-SNuPE)*; MethylLight, see Eads, et al., *MethylLight: a high-throughput assay to measure DNA methylation*, Nucleic Acids Res. Vol. 28 (2000), pp. E32; Quantitative analysis of methylated alleles (QAMA), see Zeschnigk et al., *A Novel real-time PCR assay for quantitative analysis of methylated alleles (QAMA): analysis of the retinoblastoma locus*, Nucleic Acids Res. Vol. 32 (2004), e125; combined bisulfite restriction analysis (COBRA) see Xiong et al., *COBRA: a sensitive and quantitative DNA methylation assay*, Nucleic Acids Res. Vol. 25 (1997), pp. 2532-2534, cloning and sequencing, and direct amplicon sequencing, for both see Frommer et al., *A genomic sequencing protocol that yields a positive display of 5-methylcytosine residues in individual DNA strands*, Proc. Natl. Acad. Sci. U.S.A., Vol. 89, (1992) pp. 1827-1831; reducing representation bisulfite sequencing, see Meissner et al., *Reduced representation bisulfite sequencing for comparative high-resolution DNA methylation analysis*, Nucleic Acids Res. Vol. 33 (2005), pp. 5868-2534; and Applied Biosystem's fragment analysis method, Fragment Analysis, see Boyd et al., Bisulfite method, U.S. Patent Application No. 2005/0079527, and Zon et al., Method and materials for quaternary amine catalyzed bisulfite conversion of cytosine to uracil, U.S. Patent Application No. 2005/0089898, all of which are incorporated herein, in their entireties, by reference.

According to some embodiments, the analysis of methylation can include both qualitative and quantitative techniques. Related art techniques for quantitative methylation detection are imperfect and time consuming. Real-time quantitative PCR techniques can only detect exact sequence matches to the probe and primer design. Furthermore, the loss of primer can probe specificity, once genomic DNA is converted into 3-bases, can lead to false positives and negatives, reducing the quantitativeness of techniques that depend on only a "light" signal, as an end-point. For these reasons, methylation researchers often only trust cloning and sequencing for determining exact patters and quantitiveness of methylation. The workflow for measuring methylation by cloning and sequencing can be slow, and can have multiple steps where bias is introduced, thereby distorting the ratio of methylated to non-methylated products. An initial PCR of the region of interest (which may be biased) followed by insertion of sequences into clones (some sequences clone more readily), and finally harvesting the clones, purifying the DNA and sequencing. Because of the time and expense of sequencing individual clones, a less than statistically accurate number of clones, for example, usually only 10, are analyzed, and quantitation is "determined" from this small number. It is surprising that in spite of these known flaws in methylation determination, cloning and sequencing is still the most accepted method for accurate methylation measurement. Herein is disclosed a much more accurate method for determining methylation.

According to various embodiments, the present teachings comprise bisulfite sequencing methods for the determination of the methylation characteristics of nucleic acid sequences. The systems of the present teachings can replace related art manual cloning methods while simultaneously eliminating the possibility of bias inherent in the related art methods.

According to some embodiments, the present teachings comprise a method of methylation detection. The method can comprise the bisulfite conversion of a sample of nucleic acids, for example, of gDNA. The gDNA can be fragmented before or after the bisulfite conversion. Following the bisulfite conversion, the gDNA can be diluted and inserted into the system of the present teachings. The dilution can be sufficient to insure that, on average, less than one gDNA molecule is present in each immiscible-fluid-discrete-volume (slug). For example, the dilution can be sufficient to insure that the majority of slugs contain zero or one molecule of gDNA, and statistically very few slugs contain more than one copy of gDNA. Nucleic acid amplification can be performed in the slugs with gene specific primers that are designed outside of the CpG Island, and provide amplicons regardless of methylation status. SYBRR green positive slugs can be separated (as described above) from the non-positive slugs so that only the slugs with amplicons are sequenced. Because all of the amplicons in any given slug were from a single genomic DNA template, the methylation state can determined, one molecule at a time, from each slug that is sequenced. Once enough slugs are sequenced, both the exact pattern of methylation in a region and the percentage of methylation can be accurately determined.

According to some embodiments, a specific region can be CR amplified, analogous to the current workflow for cloning and sequencing. In fact, multiple specific regions can be amplified as a "multiplex pre-amp." The present system and method can be used in place of a cloning step. The nucleic acid amplicon(s) can be diluted and introduced as a single amplicon molecule into each slug. A second nucleic acid amplification reaction can be performed using zip code primers that are complementary to the zip code sequences of a zip tailed primer used in the first nucleic acid amplification reaction. The zip tailed primers can be target specific.

The following examples all use the ability of the present system to generate slugs with one or many individual primer pairs, followed by addition of bisulfite converted DNA. (Or vice versa: many different DNAs, followed by addition of a primer pair.)

According to some embodiments, primers directed to methyl-specific sequences can be used to amplify bisulfite converted DNA. Amplification can be detected by SYBR green analysis for each slug, or by analyzing each slug, for example, by capillary electrophoresis (CE). Primers can be fluorescently labeled for analysis on CE, or intercalating dyes can be used to detect amplicons.

According to some embodiments, MethylLight probes can be used. MethylLight is a TaqMan probe based real-time PCR assay for a specific methyl C, available from Applied Biosystems, Foster City Calif. In other embodiments QAMA can be used. QAMA is a TaqMan-MGB probe based system, available from Applied Biosystems, Foster City Calif. In both cases, probe/primer sets can be introduced into slugs, along with bisulfite converted DNA. Real time or end point fluorescence detection can be used to monitor the amplification in slugs.

According to various embodiments, bisulfite converted DNA can be amplified, for example, PCR amplified. The amplicons of the PCR reaction can be digested with a restriction enzyme that recognizes a site within the amplicons. The recognition site can contain a CpG, and can be, therefore, cut or not cut depending on its methylation status. After restriction, the size and quantity of fragments can be determined by Southern blotting. This information can be used to calculate the percentage of methylation at the recognition site. In some embodiments the above technique can be referred to as COBRA. The system of the present teachings can be used to perform the nucleic acid amplification, as well as the restriction digestion. The products can be analyzed, for example, by CE using, for example, labeled primers, and/or intercalating dyes for detection. The present system thus affords increased throughput and decreased labor relative to related art techniques.

According to some embodiments, the system of the present teachings can be used to perform methylation dependent fragment separation reactions. The system of the present teachings can be used to perform nucleic acid amplification reactions with locus-specific, labeled primers. After amplification, the fragments can be analyzed by CE, as described in Boyd et al., 2006.

Additionally, the products from MethylLight, QAMA, Methylation specific PCR, COBRA, or Methylation Dependent Fragment Separation can be further analyzed by dilution to single molecule and introduction into the system of the present invention, so that the amplicons generated in a first analysis step can be further analyzed by sequencing in a second analysis step that provides additional information in assessing methylation status. MethylLight, QAMA, Methylation specific PCR, and COBRA can all provide information about a single CpG position. Furthermore, both MethylLight and Methylation Specific PCR can fail to reveal partial methylation within the amplified sequence for the PCR primers. The present system and methods can overcome this deficiency.

Figure 6:
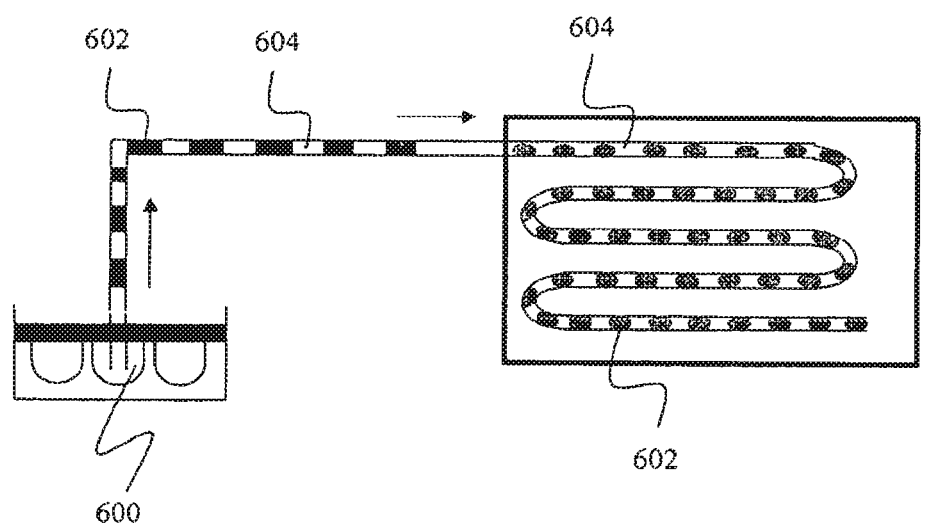
FIG. 6 illustrates a method for the creation of immiscible-fluid-discrete-volumes (slugs) of a sample, separated by a spacing fluid that is not miscible with the immiscible-fluid-discrete-volume s.
Figure 7A:
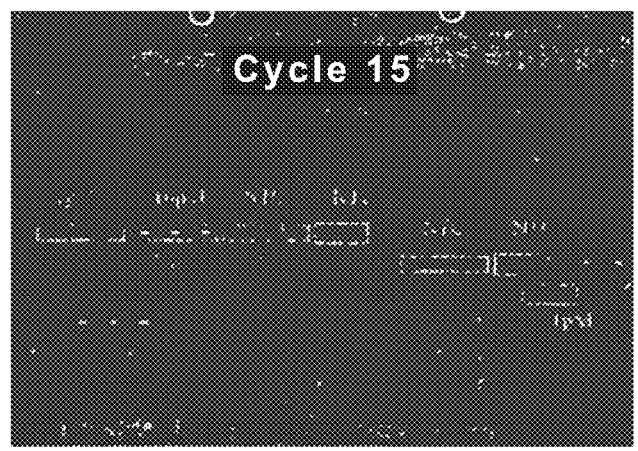
FIGS. 7A-7F show the results of the real-time PCR as imaged on an imaging thermal-cycler.
Figure 7B:
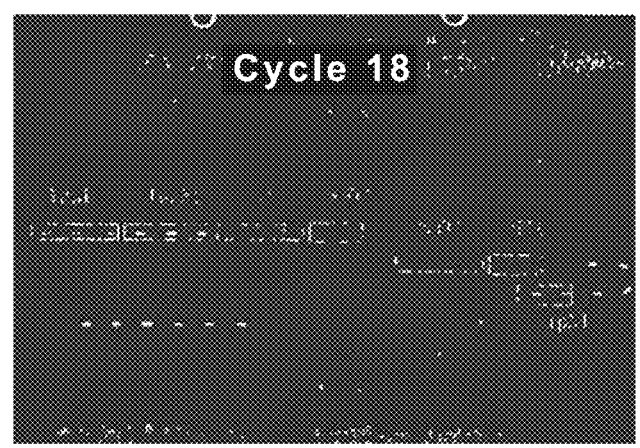
Figure 7C:
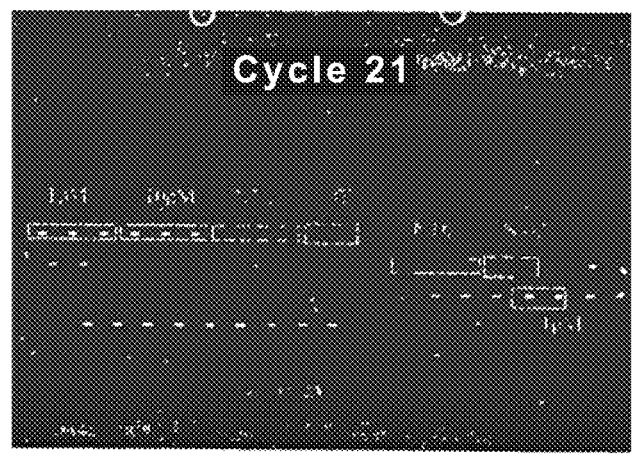
Figure 7D:
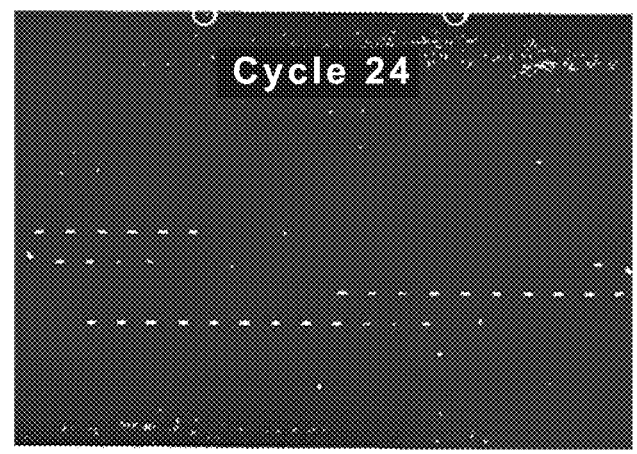
Figure 7E:
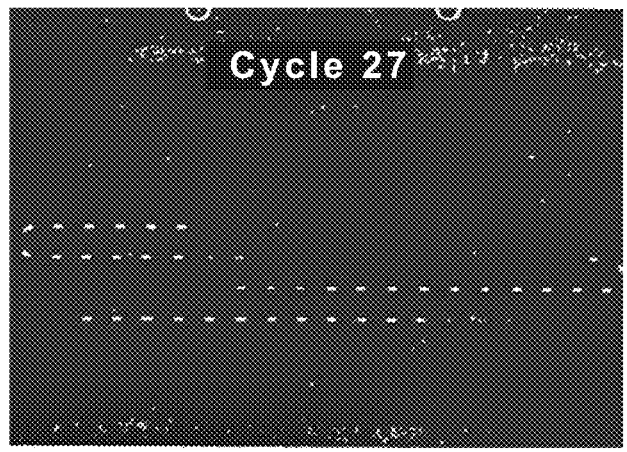
Figure 7F:
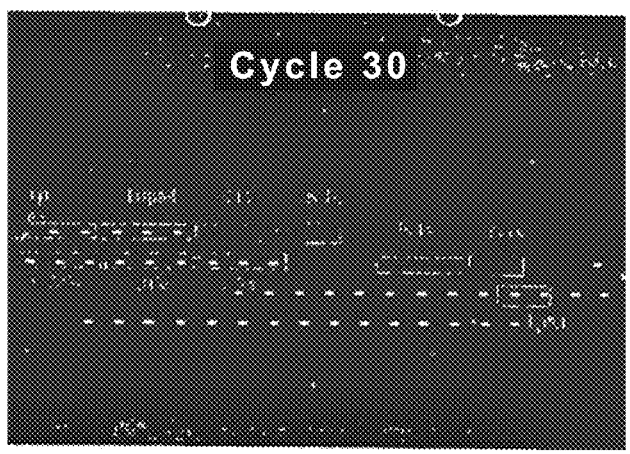

FIG. 6 illustrates the creation of immiscible-fluid-discrete-volumes 602 (slugs) of a sample 600, separated by a fluid 604 that is immiscible with the immiscible-fluid-discrete-volumes. Fluid 604 can be, for example, oil. Although Figs illustrate slugs, the concepts discussed in conjunction with these FIGS. 6-10 can be used with any discrete volumes. Sample 600 can comprise, a nucleic acid sample, SYBR green, primers, and optionally template standards. Samples can be prepared with template concentrations of, for example, 0.0 fM (no template concentration—NTC), 1 fM, 10 fM, 100 fM, 1 pM, 10 pM, and two others with no template concentration. Triplicate slugs can be made from each sample. Each batch can contain 8 samples×3 slugs/sample equals 24 immiscible-fluid-discrete-volumes. Three batches of slugs can be generated (24 slugs×3 equals 72 slugs). Real-time PCR can be performed on an imaging thermal-cycler system. FIGS. 7A-7F show the results of the real-time PCR as imaged on the imaging thermal-cycler system.

Figure 8:
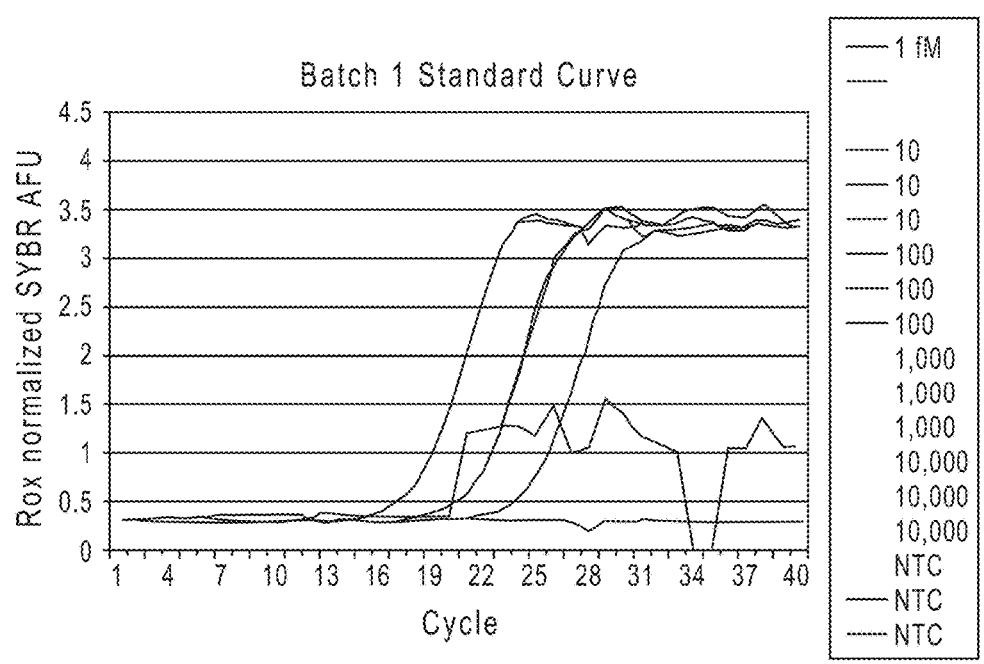
FIG. 8 is a graph showing the results of the thermal-cycling of different samples having the template molar concentrations indicated, and showing average fluorescent units (AFU) or intensities between one and 40 thermal cycles.
Figure 9:
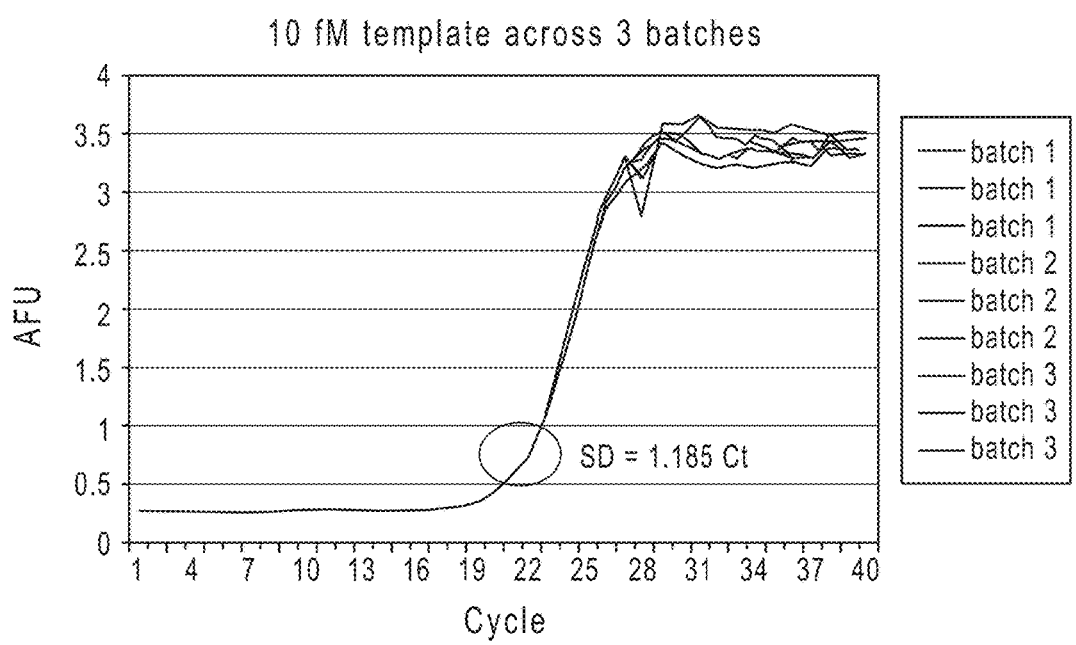
FIG. 9 shows the results of the 10 fM template concentration slugs across three batches, and shows the average fluorescent units (AFU) or intensities between one and 40 thermal cycles.
Figure 10:
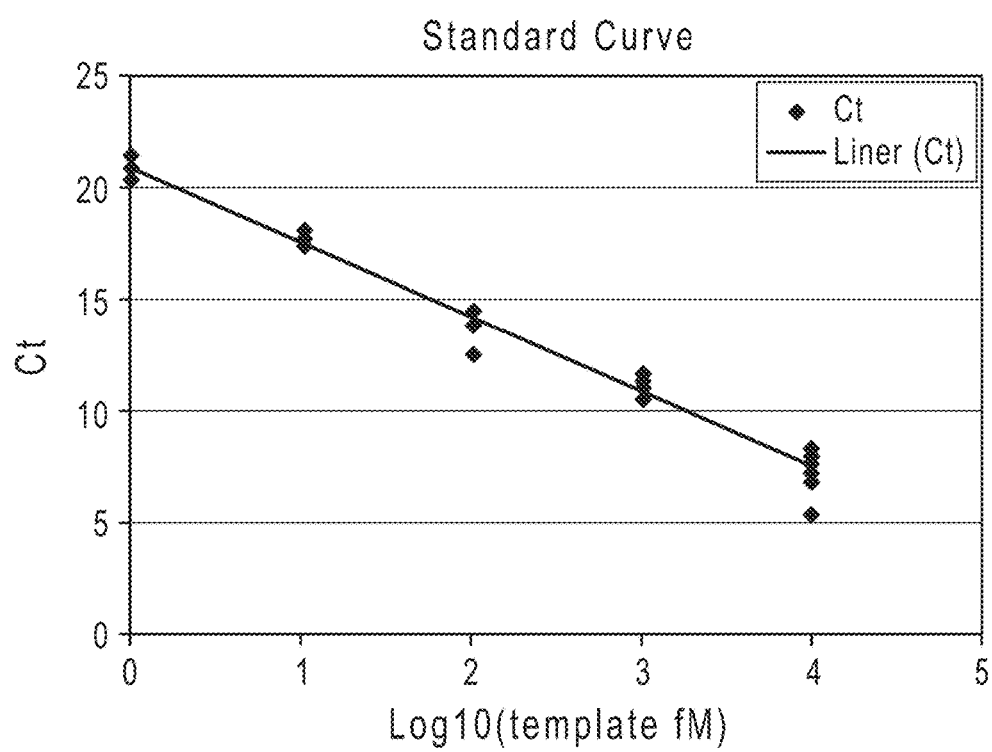
FIG. 10 shows a standard curve and plot of the results of the template-dependent reactions which are graphed in FIG. 8.

FIG. 8 shows the results of the thermal-cycling of different samples having the molar concentrations indicated. FIG. 9 shows the results of the 10 fM template containing slugs across three batches. FIG. 10 includes a standard curve indicating the results of an assay performed to determine that a real-time gene expression assay could function with in the context of the present system. FIG. 10 includes a plot of the results of the template-dependent reactions, the results of which are also shown in FIGS. 8 and 9. Gene expression assays can be conducted using any of the sequence detection systems disclosed herein. Gene expression assays can encompass any of the detection methods discussed herein, including for example, pre-amplification reactions with zip code primers.

According to various embodiments, the methods and systems can use TaqMan® reagents (Applied Biosystems, Cal.), for example, probes or primers. For example, see U.S. Pat. No. 6,154,707 to Livak, et al., incorporated herein in its entirety by reference. Other related methods known to one of skill in the art can also be used as deemed appropriate. Such reagents can be used in methods of analyzing DNA or RNA.

According to some embodiments, a library of sheared nucleic acid fragments can be ligated to universal sequences, mixed with PCR primers and SYBR green PCR reagents, and made into a set of slugs. The slugs can contain DNA fragments in a concentration of about 1 fragment per five slugs. The slugs can then be thermally cycled.

After thermal-cycling the slugs, slugs wherein nucleic acid amplification occurred can be identified by SYBR green fluorescence at about 60° C. Exonuclease and alkaline phosphatase (ExoSAP-IT) can be added to the slugs at room temperature, and fluorescent detection can be practiced.

In some embodiments, two slugs containing PCR amplified, ExoSAP-IT treated amplicons from a lambda DNA library can be added to high concentrations of sequencing primer, dNTPs, terminators and enzymes. The slugs can be thermally cycled, then dispensed into 96 well trays. After ethanol precipitation, or other cleanup, samples can be loaded in to a CE analyzer.

According to various embodiments, a method is provided that comprises amplifying a nucleic acid to form an amplicon in at least one conduit, the at least one conduit comprising an inner wall. The method can comprise attaching the amplicon to the inner wall to form an attached amplicon, and detecting the attached amplicon or an attached derivative thereof, in the at least one conduit. In various embodiments, the attached amplicon or the attached derivative thereof can comprise a double-stranded amplicon. In various embodiments, the at least one conduit can comprise no more than one single conduit. In order to facilitate the attachment of the amplicon to the wall, the oil layer can be removed. Oil can be removed using a set of electrodes, one on each side of the conduit, with an electro-magnetic field applied between the two electrodes. This can permit electro-wetting to occur at the positions of the electrodes. This process could be repeated each time interaction is desired between an aqueous reagent and the attached amplicon. It can, however, be beneficial in preventing cross contamination between slugs, for example, in the case that a label is removed for reading with a fixed detector, or to prevent variations in efficiency along the set of attached amplicons and reagents which are brought into the system. A reagent which is brought in could otherwise react with all attached amplicons before reaching the end of the conduit. Thus amplicons near the beginning of the tube could have higher efficiencies than those at the end, or additional reagent volume could be needed.

According to various embodiments, the method can comprise denaturing an attached double-stranded amplicon to form an attached single-stranded amplicon prior to detecting the attached amplicon or an attached derivative thereof, in the at least one conduit. In various embodiments, the method can comprise reacting the attached single-stranded amplicon with a label prior to detecting the attached amplicon or an attached derivative thereof, in the at least one conduit. The label can comprise a fluorescent or reporter dye, an intercalating dye, a radioactive label, a nano-barcode label or another type of marker. An intercalating dye can comprise, for example, SYBR green and can be used to identify whether or not an immiscible-fluid-discrete-volume comprises a nucleic acid sequence. In various embodiments, a label can be used to detect an amplicon, reaction products other than an amplicon, or other reagents used in the methods and systems.

According to various embodiments, the amplicon can comprise a protected chemical moiety to and thus be in the form of a protected amplicon. In various embodiments, attaching the amplicon to the at least one conduit can comprise, for example, deprotecting a protected amplicon. Deprotecting can comprise, for example, irradiating a protected amplicon with radiation of a wavelength sufficient to remove or cleave a protective group and thus deprotect a protected amplicon. According to various embodiments, the amplicon can be attached to an inner wall of the at least one conduit by an interaction of a biotin moiety and a streptavidin moiety or by other methods known to one of skill in the art.

According to various embodiments, the amplifying of a nucleic acid can comprise a thermal cycling nucleic acid sequence amplification process or an isothermal nucleic acid sequence amplification process. If a thermal cycling nucleic acid sequence amplification process is used, the process can comprise, for example, a polymerase chain reaction (PCR). The nucleic acid sequence amplification reaction can comprise an exponential amplification process, for example, PCR, or a linear amplification process, as can occur during, for example, during Sanger cycle sequencing. In various embodiments, other nucleic acid amplification processes can be used, for example, ligase chain reaction (LCR), nucleic acid sequence based amplification (NASBA), Q-beta replicase (QB) amplification, or strand displacement amplification (SDA). These alternatives, as well as others known to one skilled in the art can be used either by themselves or in combination with PCR to amplify nucleic acids.

According to various embodiments, nucleic acid sequence processing methods comprising a first type of nucleic acid amplification reaction followed by one or more of a second different type of amplification reaction, and/or detection assay reaction, can be carried out, for example, as described in U.S. Provisional Patent Application No. 60/699,782 to Faulstich et al., filed Jul. 15, 2005, and U.S. patent application Ser. No. 11/487,729 to Faulstich et al., filed Jul. 17, 2006, which are incorporated herein in their entireties by reference.

According to various embodiments, the method can comprise subjecting an attached amplicon or sets of attached amplicons to a sequencing reaction in the at least one conduit. Exemplary sequencing reactions can comprise a stepwise sequencing reaction, a forward/reverse, reverse/forward sequencing reaction, or a Sanger cycle-sequencing reaction. In various embodiments, reverse/forward or forward/reverse sequencing can comprise reactions with at least two polynucleotide primers. In various embodiments, amplification and/or sequencing reactions and/or detecting a sequenced product can be accomplished in a single conduit without removing from the tube a nucleic acid to be sequenced. As such, a nucleic acid can remain in the conduit during both an amplification reaction and a sequencing reaction. In various other embodiments, sequencing reactions, as well as detecting a sequenced product, can be accomplished in a single conduit after first removing from the conduit inner surface, an attached amplicon to be sequenced. In various embodiments, samples for sequencing can be dispensed into or onto a planar region for sequencing, for example for stepwise sequencing.

According to various embodiments, the method can comprise a sequencing reaction that in turn can comprise flowing a first labeled nucleotide into at least one conduit and hybridizing or incorporating the first labeled nucleotide to an attached amplicon to form a labeled amplicon. The method can further comprise detecting the labeled amplicon. Detecting can be done either in the same conduit in which the sequencing reaction is carried out or by flowing the labeled amplicon into an off-conduit detector. In various embodiments, sets of labeled nucleotides, for example, four sets with each set containing a different labeled nucleotide, can be repeatedly flowed back and forth past an attached amplicon, to obtain sequencing information.

According to various embodiments, the method can comprise forming a labeled amplicon, washing the labeled amplicon to form a washed amplicon, flowing a second labeled nucleotide into the at least one conduit, hybridizing or reacting the second labeled nucleotide to the attached washed amplicon to form a second labeled amplicon, and detecting the second labeled amplicon. In various embodiments, a second labeled nucleotide can differ from a first labeled nucleotide. Additional labeled nucleotides can subsequently be flowed into the at least one conduit and hybridized to or reacted with respective attached washed amplicons. The method can further comprise detecting the labeled amplicon. Detecting can be done either in the same conduit in which the sequencing reaction is carried out or by flowing the labeled amplicon into an off-conduit detector. In various embodiments, incorporation of labeled nucleotides can create free detectable dye and the amount detected can increase when multiple bases are labeled, for example, if there are repeating A's or C's present in the molecule being sequenced.

According to various embodiments, the method can comprise forming a plurality of aqueous immiscible-fluid-discrete-volumes inside at least one conduit, wherein each of a plurality of the volumes are isolated from adjacent immiscible-fluid-discrete-volumes by spacing fluid. The spacing fluid can be immiscible with the plurality of immiscible-fluid-discrete-volumes. At least one of the immiscible-fluid-discrete-volumes can contain one or more target nucleic acid sequences. In various embodiments, the spacing fluid can comprise an oil or other liquid that is immiscible relative to the immiscible-fluid-discrete-volumes, for example, immiscible with an aqueous solution. At least one of the immiscible-fluid-discrete-volumes can comprise a single target nucleic acid molecule.

According to various embodiments, a method is provided comprising contacting an aqueous sample fluid with a non-aqueous spacing fluid that is immiscible with the aqueous sample, in a conduit, to form a plurality of immiscible-fluid-discrete-volumes or discrete volumes of the aqueous sample fluid separated from one another by the non-aqueous spacing fluid. The aqueous sample fluid can comprise a plurality of target nucleic acid sequences, and at least one of the discrete volumes can comprise a first discrete volume that contains at least one target nucleic acid sequence. The method can comprise amplifying the at least one target nucleic acid sequence in the first discrete volume in the conduit to form an amplicon, and subjecting the amplicon to a nucleic acid sequencing reaction in the conduit.

According to various embodiments, each of the plurality of isolated fluid portions in the conduit can comprise one or more respective oligonucleotide primers. Oligonucleotide primers can be chosen as determined by one of skill in the art to accomplish the desired objective, for example, universal primers can be used. Various embodiments can comprise universal PCR that can comprise up-front multiplexed PCR followed by decoding, for example, see, WO 2004/051218 to Andersen et al., U.S. Pat. No. 6,605,451 to Marmaro et al., U.S. patent application Ser. No. 11/090,830 to Andersen et al., and U.S. patent application Ser. No. 11/090,468 to Lao et al., all of which are incorporated herein in their entireties by reference. Details of real time PCR can found in Higuchi et al., U.S. Pat. No. 6,814,934B1, which is incorporated herein by reference in its entirety.

According to various embodiments, prior to amplifying the at least one target nucleic acid sequence, at least 50% of the plurality of isolated aqueous portions in the conduit can each comprise a single target nucleic acid sequence. In various other embodiments, less than about 50% of the plurality of isolated aqueous portions in the conduit can each comprise a single target nucleic acid sequence. In other embodiments, at least 1% or more, 5% or more, 10% or more, or 20% or more can have a single target nucleic acid sequence.

According to various embodiments, the method can comprise introducing polymerase chain reaction inactivating reagents into the conduit after amplifying the at least one target nucleic acid sequence and before subjecting the nucleic acid sequence to a sequencing reaction. The reagents can be used to inactivate or remove or eliminate excess primers and/or dNTP's. The inactivating reagents can be introduced at a junction in the conduit, for example, after an aqueous sample fluid-immiscible-fluid-discrete-volume to be inactivated is aligned with the junction. The junction can comprise, for example, a T-intersection.

According to various embodiments, one or more target nucleic acid sequences can be subjected to a sequencing reaction to form a detectable product, and the method can comprise detecting the detectable product. In various embodiments, the detectable product can be detected inside the same conduit where the detectable product is formed. In other embodiments, the detectable product can be transferred out of the conduit and detected using, for example, using a flow cell or a capillary electrophoretic sequencer. In various other embodiments, an off-conduit detector can be used as deemed appropriate.

According to various embodiments, the method can comprise attaching an amplicon to an inner wall of a conduit to form an attached amplicon and flowing at least one sequencing reaction primer into the conduit such that the sequencing reaction primer reacts with the attached amplicon in the conduit. In various embodiments, a double stranded amplicon can be denatured, primers can be hybridized and a sequencing reaction conducted. In other embodiments, all reactions can be done in a single mixture of reagents. Intercalating dyes for detection by a detector can be added as deemed appropriate either before or after denaturation.

According to various embodiments, the method can comprise continuously flowing at least one of an aqueous sample fluid and non-aqueous spacing fluid into a conduit. In various other embodiments, contacting an aqueous sample fluid with a non-aqueous spacing fluid can comprise alternating injecting an aqueous sample fluid and a non-aqueous spacing fluid into the conduit. According to various embodiments, the conduit can comprise an inner wall and the method can comprise attaching an amplicon to the inner wall to form an attached amplicon and then flowing at least one sequencing reaction primer into the conduit such that the sequencing reaction primer in the conduit reacts with the attached amplicon. In various embodiments, one fluid can be continuously flowed into the conduit and a second fluid can be injected into the continuously flowed fluid to form aqueous immiscible-fluid-discrete-volumes spaced-apart from one another by a non-aqueous spacing fluid.

According to various embodiments, the method can comprise attaching the amplicon to the inner wall to form the attached amplicon, flowing at least one sequencing reaction reactant into the conduit such that the at least one sequencing reaction reactant can react with the attached amplicon to form a double-stranded sequencing reaction product, and then denaturing the double-stranded sequencing reaction product for further analysis or processing. In various embodiments the double stranded reaction product is not denatured for further analysis. In other embodiments, a double stranded amplicon can be denatured prior to addition of the primers.

According to various embodiments, a method is provided that can comprise flowing a first fluid and a second fluid into a conduit, the first fluid and the second fluid being immiscible with respect to one another, wherein the first fluid containing a plurality of target molecules and the maximum inner cross-sectional dimension of the conduit is such that a plurality of immiscible-fluid-discrete-volumes of the first fluid are formed in the conduit and separated from one another by the second fluid and at least one of the slugs of the first fluid contains a single target molecule. According to various embodiments, at least one of an immiscible-fluid-discrete-volume of a first fluid is free of target molecules. According to various embodiments, the method can comprise amplifying at least one of a plurality of target molecules to form an amplification product. In various embodiments, primer sites can be ligated to the target molecules. The amplification product can comprise a nucleic acid and the method can comprise subjecting the amplification product to a nucleic acid sequencing reaction and/or sequencing. The nucleic acid sequencing reaction can comprise a Sanger cycle sequencing reaction, a step-wise sequencing reaction, or a forward/reverse sequencing reaction involving primers.

According to various embodiments, the method can be carried out in a conduit, for example, a capillary tubing conduit. An exemplary conduit that can be used can have an inner diameter of about 1000 microns or less. In other embodiments the inner diameter can be about 300 microns or less, for example, about 100 microns or less, or about 50 microns or less. Other embodiments can involve methods that use a conduit having an inner diameter that is greater than about 300 microns, for example, about 1000 microns or less, or about 500 microns or less. In various embodiments, the above dimensions can refer to the cross-sectional area of a conduit. Such a conduit can be rectangular in shape or have another shaped as deemed appropriate by one of skill in the art. Various systems and apparatus can also be provided that include such a conduit.

According to various embodiments, the first fluid can comprise an aqueous fluid, the plurality of target molecules can comprise a plurality of target nucleic acid sequences, and the second fluid can comprise an oil The plurality of target nucleic acids can comprise a plurality of the same target nucleic acid molecule and/or a plurality of different target nucleic acid molecules.

According to various embodiments, the method can comprise adding to at least one of a plurality of immiscible-fluid-discrete-volumes of a first fluid, one or more additional aqueous reagents to form at least one extended immiscible-fluid-discrete-volume. In various embodiments, additional aqueous reagents can be added to the at least one extended immiscible-fluid-discrete-volume to form at least one further extended immiscible-fluid-discrete-volume.

According to various embodiments a system is provided comprising at least one conduit comprising an inner surface and having a maximum inner cross-sectional dimension, an aqueous sample fluid introduction unit in fluid communication with the at least one conduit, a spacing fluid introduction unit in fluid communication with the at least one conduit, and a control unit adapted to flow an aqueous sample fluid and a spacing fluid from the aqueous sample fluid introduction unit and the spacing fluid introduction unit, respectively. The aqueous sample fluid introduction unit and the spacing fluid introduction unit can comprise separate units, each in fluid communication with the at least one conduit. The introduction units can be, for example, pumps or another apparatus adapted to produce controlled injection of fluids into a conduit. The control unit can be adapted to control the introduction units to inject volumes of aqueous sample fluid and spacing fluid that respectively form immiscible-fluid-discrete-volumes in the at least one conduit wherein each immiscible-fluid-discrete-volume comprises an outer dimension that is equal to the maximum inner cross-sectional dimension of the conduit. One of skill in the art would understand that the maximum inner cross-sectional dimension of a conduit would be the diameter of the tube, whereas the maximum inner cross-sectional dimension of a rectangular conduit can depend on the dimensions of the conduit.

The inner surface can comprise an attached linker moiety. In various embodiments, the system can comprise a non-aqueous liquid source in fluid communication with a spacing fluid introduction unit. The system can comprise an aqueous sample fluid source in fluid communication with an aqueous sample fluid introduction unit, and a spacing fluid source in fluid communication with a spacing fluid introduction unit. The aqueous sample fluid source can comprise at least one nucleic acid sequence. The at least one conduit can comprise two conduits joined together or forming an intersection and can include a third conduit segment or channel in fluid communication with an additional reagent supply source. The intersection can comprise, for example, a T-intersection or a Y-intersection. In various embodiments, the intersection can comprise a valveless intersection where a stream of aqueous sample fluid and a stream of non-aqueous spacing fluid can merge together. For example, microfabrication technology and the application of electrokinetics or magnetohydrodynamics, can achieve fluid pumping in valveless, electronically controlled systems. Components comprising shape-optimized channel turns, optimal injection methods, micromixers, and/or high flow rate electroosmotic pumps can be used in a valveless system.

According to various embodiments, the system can comprise a detection device adapted to detect a component of an aqueous sample fluid source. A detection device can comprise a spectrophotometer, a refractive index detector, a fluorometer, an excitation beam source, a charge-coupled device, a camera, photodiode or a combination thereof. Other detection methods can be used, for example, absorption, refractivity or other methods known to those of skill in the art. An aqueous sample fluid source can comprise a nucleic acid sequence.

According to various embodiments, the system can comprise a thermal-cycling device adapted to thermally cycle an aqueous sample fluid in the at least one conduit. The thermal cycling device can comprise a heat source, for example, a radiant or non-radiant heat source, and a cooling source, for example, a fan, an air jet, or a liquid-circulating system in a thermal block. The thermal cycling device can comprise one or more temperature sensors and one or more control units for controlling heating and cooling according to a desired thermal cycle. The conduit can comprise a conduit having an inner diameter and the inner diameter can be about 300 microns or less, for example, about 100 microns or less, or about 50 microns or less. In other embodiments, a conduit can have an inner diameter greater than about 300 microns. Other details about the thermal-cycling device, conduit, and other system components will become apparent in view of the description that follows. For example a multi-zone system, can comprise an oven, a plate, or a cylinder. The cylinder can comprise a conduit around either its internal or external diameter. The thermal cyclers can be used in either a batch mode or a flow through mode. For example, see Haff et al. U.S. Pat. No. 5,720,923, which is incorporated herein, by reference.

According to various embodiments, a method is provided that can comprise preparing a sample for analysis. Samples can comprise any molecules whose analysis or preparation can benefit from methods or systems described herein, for example, a nucleic acid sequence or a polypeptide. Samples can be prepared and/or analyzed either by being attached to an inner surface of a conduit and/or by being flowed through the conduit. In various embodiments, the method can involve a combination of first attaching a sample to an inner surface of a conduit and subsequently flowing the sample through the conduit.

Preparing the sample can comprise forming sample immiscible-fluid-discrete-volumes separated by spacing fluid. The sample immiscible-fluid-discrete-volumes can comprise an aqueous solution, for example, a biological sample such as a nucleic acid sequence-containing sample. The sample immiscible-fluid-discrete-volumes can be flowed along a conduit to positions where they can undergo additional preparation or analysis. More than a single processing or analysis procedure can be performed on a sample immiscible-fluid-discrete-volume as the sample immiscible-fluid-discrete-volume flows through the conduit. Alternatively, processing or analysis can instead, or additionally, occur in or to a stationary immiscible-fluid-discrete-volume in the conduit. Additional reagents or samples can be added to those already in a sample immiscible-fluid-discrete-volume as the sample immiscible-fluid-discrete-volume flows through or remains stationary in the conduit. Additional reagents can be added through inlet ports or channels that are in fluid communication with the conduit. Inlet channels can be formed, for example, at a T-intersection or a Y-intersection. Additional reagents or buffer solutions added through inlet ports or channels, for example, can comprise cleaning immiscible-fluid-discrete-volumes for a continuous flow system.

According to various embodiments, the method can comprise a combination of flowing a sample immiscible-fluid-discrete-volume and intermittently stopping a flow to permit further processing. Processing or analysis of the sample can comprise, for example, binding a molecule to a surface, amplifying a molecule, sequencing a molecule, or detecting a molecule. In various embodiments, flow can occur in either a forward or backward direction or a continuous loop, thereby allowing a reagent to be re-used multiple times. The method can be applied to techniques that process small distinct volumes of a sample, wherein small immiscible-fluid-discrete-volumes can comprise less than about 100 μl, less than about 1 μl, less than about 500 nl, less than about 250 nl, less than about 100 nl, or less than about 50 nl. In various embodiments, the length of the immiscible-fluid-discrete-volume can be about the same size as the diameter of the immiscible-fluid-discrete-volume.

According to various embodiments, a method is provided that can sequence a single target nucleic acid molecule after first amplifying the target nucleic acid in a conduit. The methods can involve using a small volume for sequencing amplified nucleic acids. Nucleic acid can be amplified and/or sequenced, for example, under immobilized solid-state conditions, while continuously flowing a solution past the immobilized nucleic acid in the conduit. Alternatively, the nucleic acid can be in a measured fluid portion or immiscible-fluid-discrete-volume in the conduit. The fluid portion or immiscible-fluid-discrete-volume can be, for example, continuously flowing or intermittently stationary in a conduit. In various embodiments, an immiscible-fluid-discrete-volume can be brought to a position of interest along a conduit at a non-reacting temperature, the flow can be stopped and the temperature changed to a level to allow a reaction or hybridization to occur with a target sample.

According to various embodiments, the method can involve the use of a system or device that provides sample slugs to a conduit, for further processing. The sample slugs can each comprise a single target nucleic acid molecule, for example, in a solution or mixture. Further processing of the nucleic acid can comprise amplifying the nucleic acid and/or sequencing the nucleic acid. Further processing of molecules other than nucleic acids is also within the realm of the present teachings as will be appreciated by those of skill in the art. According to various embodiments, the slugs can either be flowed continuously or can be intermittently stationary in a conduit during amplification and/or sequencing procedures. Slugs comprising a nucleic acid to be amplified or sequenced can be less than about 100 μl, less than about 1 μl, less than about 500 nl, less than about 250 nl, less than about 100 nl, or less than about 50 nl.

According to various embodiments, the present teachings comprise creating emulsified droplets. The emulsified droplets can comprise one or more nucleic acid fragments. The emulsified droplets can have volumes of between about 1 femtoliter and 1 nanoliter.

According to various embodiments, the sequencing methods that can be carried out according to the present teachings can comprise: direct sequencing; step-wise sequencing; Sanger sequencing; cycle sequencing; sequencing by synthesis; fluorescent in situ sequencing (FISSEQ); sequencing by hybridization (SBH); sequencing with forward and reverse primers in the same reaction, followed by physically separating the forward and reverse sequencing ladders before analysis; pyrosequencing; sequencing using boronated oligonucleotides; electrophoretic sequencing; micro-electrophoretic sequencing; capillary electrophoretic sequencing; or other nucleic acid sequencing methods known in the art, that can be applied to small sample volumes. Exemplary descriptions of sequencing in various volumes can be found in U.S. Pat. No. 5,846,727 to Soper et al., U.S. Pat. No. 5,405,746 to Uhlen, U.S. Pat. No. 6,154,707 to Livak et al., and Soper et al., Anal. Chem. 70:4036-4043 (1998), all of which are incorporated herein in their entireties by reference.

According to various embodiments, a method is provided for amplifying and sequencing a target DNA wherein both processes can occur the in the same conduit. In various embodiments, DNA can initially be provided in single-stranded form. A target DNA can be amplified by PCR or other suitable amplification reaction to form a double-stranded amplicon. The double-stranded amplicon can incorporate a terminally labeled and protected biotinylated molecule. The biotin can be initially attached to a primer. The terminally labeled biotinylated molecule can bind to a streptavidin moiety when the protective portions of the molecule are removed or inactivated. Alternatives to a biotin-streptavidin binding that are known in the art can also be used.

According to various embodiments, terminal labeling of molecules can be accomplished, for example, using an affinity labeled primer. Primers can comprise an affinity moiety, thereby allowing for the binding of reaction products to affinity-binding moieties. For example, a specific binding pair comprising biotin and streptavidin can be employed. A biotin affinity moiety can be incorporated into a primer, and a streptavidin binding moiety can be used to bind, or can bind and immobilize the biotin-incorporated primer. Unbound unincorporated reaction components can be removed, and the nucleic acid strand complementary to the biotin-bearing strand can be isolated and analyzed. It will be appreciated that the members of a specific binding pair can be switched and still accomplish the desired binding to a surface, for example, the streptavidin can be attached to the primer and act as an affinity moiety, and the biotin can be attached to a solid support and act as a binding moiety. The procedures used for binding, and/or binding and immobilization, are well known to one of skill in the art. Bound, but unused single-stranded primer can be later digested.

According to various embodiments, a double-stranded amplicon with a binding moiety can be attached or immobilized to an inner surface of a conduit or other conduit. Various functional groups can be used to accomplish attachment or immobilization of nucleic acids. A functional group can be any compound that can be incorporated into or attached to an oligonucleotide and that has a strong interaction to a molecule that can be immobilized on a solid-support. If elevated reaction temperature is used to analyze or process an attached molecule, stability of the functional groups at such temperatures can be a consideration.

Examples of binding pairs can comprise biotin-avidin, biotin-streptavidin, or cystein-thiol groups. An example, of a functional group for binding nucleic acids to a surface is 11-biotin-dUTP. A biotin-avidin-biotin three component linkage of a molecule to be attached to a surface can also be used. If an oligonucleotide is attached to a surface, interaction between binding components on the surface and the oligonucleotide should be stable during the amplification and/or sequencing procedure. In various embodiments, directly or indirectly, light activated or heat activated reactive groups on a primer that can react with a surface coated reactive group, can be used.

Incorporation of a terminal functional group into a nucleic acid being synthesized can be accomplished, for example, with a polymerase, such as Klenow, T7, or reverse transcriptase. Instead, a functional group of interest can be attached to an oligonucleotide by ligation to a suitable oligonucleotide that has already been synthesized.

If an oligonucleotide is to be attached to a bead, the attachment can be done either batch-wise with a substance-coupled carrier slurried in a suitable medium, or on a column comprising an activated carrier. Any conventional carrier material (for example, Sepharose beads, (Pharmacia, Sweden)), filters, capillaries, or plastic dipsticks (for example, polystyrene strips), and microtitre wells to which the substance can be sufficiently coupled, can be used, depending on the application for which a nucleic acid is to be used.

Nucleic acids for sequencing reactions can be prepared by methods known to one of skill in the art. Methods can comprise chemical synthesis, or shotgun cloning in bacteria or yeast, as is well-known to those in the art. According to various embodiments, nucleic acids can also be prepared by enzymatic methods, for example, by a PCR reaction or a chain ligase reaction. Enzymatic methods of amplification can provide an alternative to the biological amplification of cloning in bacteria or yeast. Enzymatic amplification can provide sufficient DNA for micro- or nano-sequencing reactions.

According to various embodiments, an amplicon can be obtained in an aqueous immiscible-fluid-discrete-volume by methods of the present teachings. Amplification of target nucleic acids, with detection resulting from the increased amount of target relative to the copy number present in the starting material, can be accomplished. Amplification of target nucleic acids can comprise, for example, whole gene amplification techniques and/or specific sequences can be targeted. Various sequences individually or together can be targeted. The sequences can comprise immobilized or not immobilized sequences. Suitable amplification procedures can include the polymerase chain reaction, chain ligase reaction, and isothermal amplification, although it will be appreciated that other amplification strategies might be employed in order to generate enough amplicon.

According to various embodiments, an enzyme that polymerizes nucleotide triphosphates into amplified fragments can be a heat-resistant DNA polymerases known in the art. Polymerases that can be used in the method of the invention comprise DNA polymerases from such organisms as *Thermus aquaticus, Thermus thermophilus, Thermococcus litoralis, Bacillus stearothermophilus, Thermotoga maritima* and *Pyrococcus* ssp. The enzyme can be isolated from source bacteria, produced by recombinant DNA technology or purchased from commercial sources. Exemplary DNA polymerases that can be used include those available from Applied Biosystems (Foster City, Calif.), for example, AmpliTaq Gold™ DNA polymerase; AmpliTaq™ DNA Polymerase; Stoffel fragment; rTth DNA Polymerase; and rTth DNA Polymerase XL. Other suitable polymerases that can be used include, but are not limited to, Tne, Bst DNA polymerase large fragment from *Bacillus stearothermophilus*, Vent and Vent Exo− from *Thermococcus litoralis*, Tma from *Thermotoga maritima*, Deep Vent and Deep Vent Exo− and Pfu from *Pyrococcus*, and mutants, variants and derivatives of the foregoing. For further discussion of polymerases, and applicable molecular biology procedures generally, see, Ausubel et al., Current Protocols in Molecular Biology, John Wiley & Sons, New York, 2001, and The Polymerase Chain Reaction, Mullis, K. B., F. Ferre, and R. A. Gibbs, Eds., Molecular Cloning: A Laboratory Manual, (3rd ed.) Sambrook, J. & D. Russell, Eds. Cold Spring Harbor Laboratory Press, Cold Spring Harbor, N.Y. (2001), all of which are incorporated herein in their entireties by reference.

Amplification reaction times, temperatures, and cycle numbers can be varied to optimize a particular reaction. Addition of additives to reduce stutter and reduce non-specific amplification can also be used as determined appropriate by one of skill in the art, for example, see US Patent Application Publication 2005/0112591 to Dimoski et al., which is incorporated herein in its entirety by reference.

According to various embodiments, one can incubate a reaction at a certain temperature following the last phase of the last cycle of PCR. In some embodiments, a prolonged extension phase can be selected. In other embodiments, an incubation at a low temperature (for example, 4° C.) can be selected. In various embodiments, temperature can be changed during introduction of reagents or alternatively, temperature can be changed at various areas along a conduit where a desired reaction can occur.

According to various embodiments, a conduit is provided that can comprise closed ends and a plurality of sample immiscible-fluid-discrete-volumes isolated from adjacent sample immiscible-fluid-discrete-volumes by spacing fluid that is immiscible with the plurality of sample immiscible-fluid-discrete-volumes, wherein at least two of the sample immiscible-fluid-discrete-volumes comprise reagents. The conduit can contain reagents attached to the inner surface of the conduit. In various embodiments the reagents in the conduit can be nucleic acids. The nucleic acids can be primers. The primers can be the same or different in each sample immiscible-fluid-discrete-volume.

According to various embodiments, a DNA library can be prepared for analysis. Genomic libraries have been prepared by a variety of methods, for example, restriction digestion and ligation, mechanical fragmentation and enzymatic "tailing," and PCR amplification using primers. Methods of library preparation are known in the art, for example, in Nucl. Acids Res. 25:781-786 (1997), Nucl. Acids Res. 17:3645-3653 (1989), both of which are incorporated herein in their entireties by reference.

Figure 11:
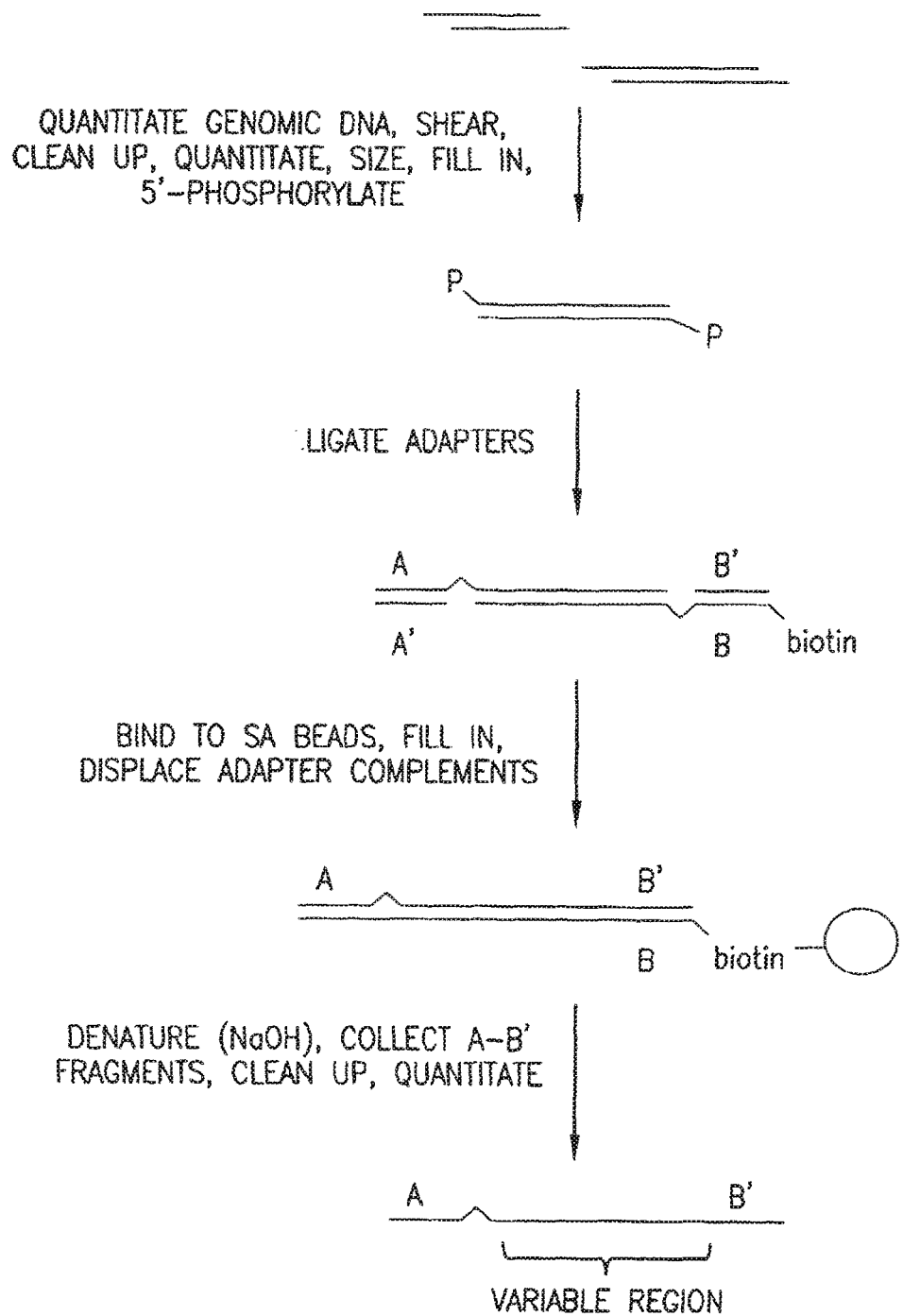
FIG. 11 illustrates a generation of a DNA library.

A library can be prepared enzymatically without first cloning DNA in bacteria. As illustrated in FIG. 11, DNA can be digested or sheared into appropriate sized fragments, for example, fragments of about 50 bp, 100 bp, about 200 bp, about 500 bp, about 1000, or about 2000 bp. Sheared DNA can be filled in by end repair using 5' phosphorylation and polymerization using a Klenow fragment of DNA polymerase, for example, see Kinzler et al., Nucleic Acids Res. 17:3645-3653 (1989), incorporated herein by reference, and adapters can then be ligated to ends of sized fragments for attachment to an appropriate surface. An adapter can comprise a sequence of interest attached to a biotin moiety that has been ligated to a DNA fragment. The biotin moiety permits a DNA fragment to bind to a surface, for example, a bead or a conduit coated with streptavidin.

According to various embodiments, biotin-streptavidin can be a suitable choice for attaching a nucleic acid to a surface for generation of a nucleic acid library, as well as for amplification and sequencing reactions in a conduit, because a biotin-streptavidin linkage can withstand large and rapid temperature changes experienced in performing such reactions. Attachment by other than a biotin-streptavidin linker can also be used. Such linkers should also be able to withstand large and rapid temperature changes. If, however, an isothermal method is used, stability to large and rapid temperature changes may not be necessary.

Unfilled portions of a DNA fragment can be filled in and the complement can be displaced by denaturation. Fragments of interest can be collected and quantitated. A collected fragment can include, for example, variable regions of genomic DNA.

According to various embodiments, nucleic acids generated by a library, for example, the library shown in FIG. 11, can be diluted by a limiting dilution procedure such that a concentration of a single molecule of interest per a given volume of liquid can be obtained. Nucleic acids obtained by any method can be diluted to a concentration of about one molecule per given volume prior to analysis. When a sample is diluted to this extent, some volumes may not have any nucleic acid molecules, while others can have more than 1 molecule. For example, in some embodiments, the majority of volumes can have a single molecule. According to various embodiments, the sample can be diluted such that at most about 40% of the immiscible-fluid-discrete-volumes produced from a sample in the process described below can comprise a single target nucleic acid sequence. In various other embodiments, less than about 37% of the immiscible-fluid-discrete-volumes produced can each comprise a single target nucleic acid sequence. In other embodiments, at least 1% or more, 5% or more, 10% or more, or 20% or more can comprise a single target nucleic acid sequence, for example, from about 5% to about 40%, or from about 10% to about 20%. One of skill in the art can appreciate how to prepare a solution by limiting dilution. After a sample is diluted by limiting dilution, a single nucleic acid molecule can be introduced into a conduit in an aqueous immiscible-fluid-discrete-volume. Not all aqueous immiscible-fluid-discrete-volumes formed from a nucleic acid solution theoretically diluted to one molecule per given volume will necessarily have a nucleic acid in every given volume. In various embodiments, about 10% or less, about 20% or less, or about 50% or less of the aqueous immiscible-fluid-discrete-volumes can have one nucleic acid molecule per given volume.

According to various embodiments, a banded or zebra pattern of aqueous immiscible-fluid-discrete-volumes comprising a single nucleic acid molecule, separated from one another by spacing fluid, can be prepared for flowing into a conduit or can be formed in the conduit. The conduit can comprise, for example, a plastic tube. The spacing fluid is immiscible with respect to the immiscible-fluid-discrete-volumes, for example, such that distinct immiscible-fluid-discrete-volumes can be formed that are separated from one another by spacing fluid. According to various embodiments, the conduit can comprise any type of channel including, but not limited to, a tube, a groove, a channel formed by opposing barriers, or the like.

According to various embodiments, immiscible-fluid-discrete-volumes can be prepared in a system. The system can comprise a spacing fluid introduction unit in fluid communication with at least one conduit, an aqueous sample fluid introduction unit in fluid communication with the at least one conduit, and a control unit adapted to control the flow of an aqueous sample fluid and of a spacing fluid from the aqueous sample fluid introduction unit and the spacing fluid introduction unit, respectively. The control unit can be adapted to introduce volumes of aqueous sample fluid and spacing fluid that respectively form immiscible-fluid-discrete-volumes in the at least one conduit. In some embodiments, each immiscible-fluid-discrete-volume can comprise a slug having an outer dimension equal to the maximum inner cross-sectional dimension of the conduit. In various embodiments, the aqueous sample fluid introduction unit and the spacing fluid introduction unit can comprise a single device in the system. Alternatively, any or all of the components of the system can be found in a single device rather than as separate units.

According to various embodiments, immiscible-fluid-discrete-volumes can be prepared at a junction by applying a fixed pressure to oil and aqueous solutions of interest that are in a conduit. Immiscible-fluid-discrete-volumes can form with a size and speed that is a function of the conduit, junction diameter, pressure for each fluid, and/or viscosity of each fluid.

Figure 12:
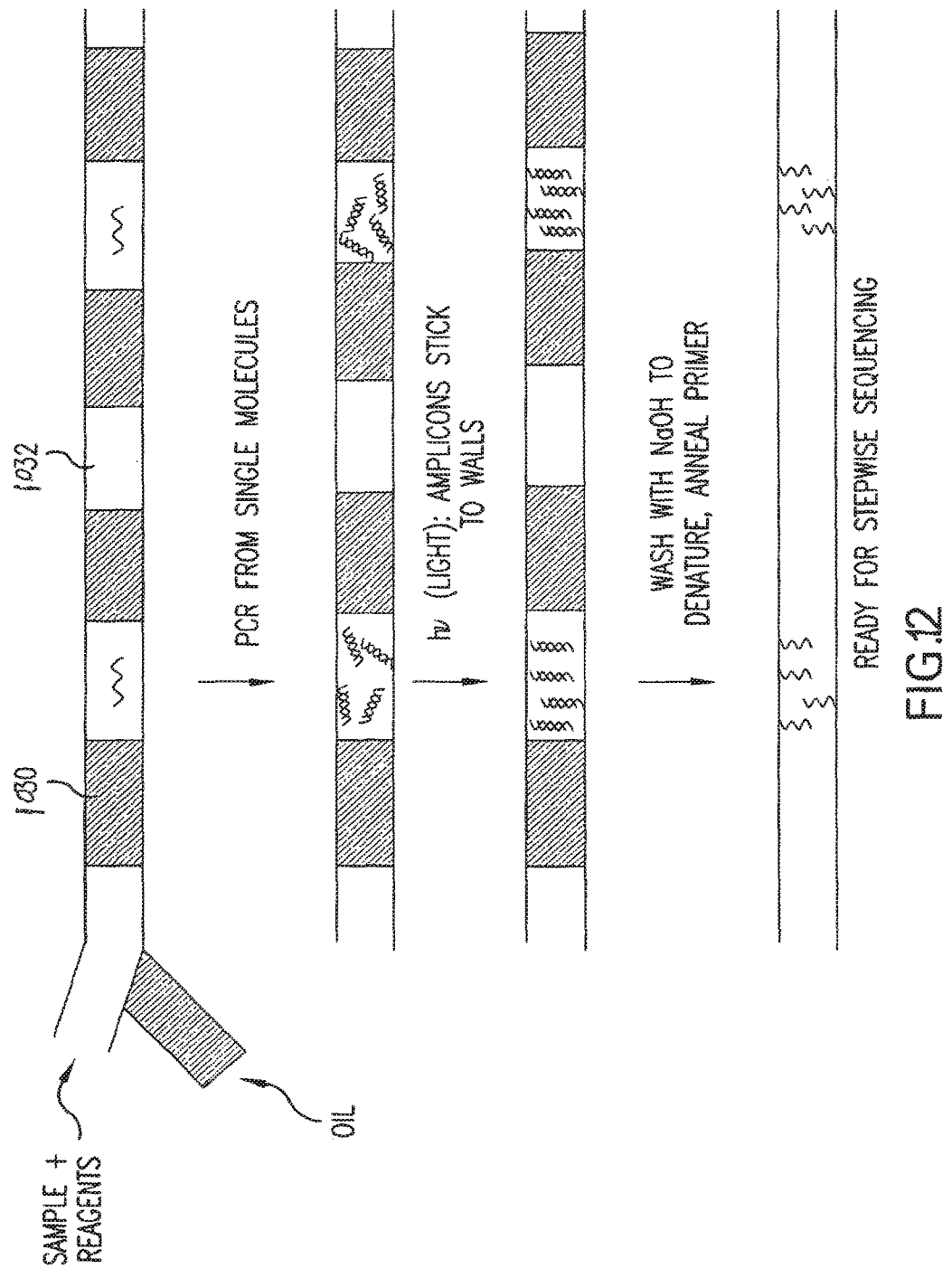
FIG. 12 illustrates a sample preparation for a stepwise sequencing reaction.

According to various embodiments, and as illustrated in FIG. 12, DNA can be prepared for stepwise sequencing. A DNA sample from a library can be diluted by limiting dilution to arrive at a concentration of a single DNA molecule per aqueous immiscible-fluid-discrete-volume 1032 that is flowed into a conduit with spacing fluid 1030. In some embodiments, the DNA can be diluted so that the number of DNA molecules contained per aqueous immiscible-fluid-discrete-volume can be mostly zero, some with one, and very few with two or more. Aqueous immiscible-fluid-discrete-volumes can comprise primers, a DNA target sample, PCR reagents, and fluorescent dyes, for example, SYBR green. In the conduit a single DNA molecule can be amplified.

According to various embodiments a sequencing procedure can use water-soluble rhodamine dye conjugates, for example, see U.S. Pat. No. 6,191,278 to Lee et al. (incorporated herein in its entirety by reference). According to other embodiments, dye-terminator chemistries (dRhodamine and Big-Dye™) can be employed. Big-Dye™ terminators as described, for example, in U.S. Pat. No. 5,800,996 to Lee et al., incorporated herein in its entirety by reference, can be used.

According to various embodiments, PCR can be performed in an aqueous immiscible fluid-discrete-volume in a conduit to amplify a nucleic acid molecule, although other methods can be used to amplify the nucleic acid molecule, for example, reverse transcriptase PCR (RT-PCR) or a ligase chain reaction. During amplification, a terminal moiety comprising, for example, a caged biotin, can be incorporated into the nucleic acid being synthesized or amplified such that an amplified nucleic acid (amplicon) can be treated to attach the nucleic acid to an inner surface of a conduit. The terminal moiety can be incorporated through the primers used in amplification. In some embodiments, the terminal moiety can be located at a position other than the 3' or 5' terminal of the polynucleotide of interest, provided the moiety can be used to attach the amplicons to a solid support. In various embodiments, a single DNA molecule can be attached first and then amplified. In some embodiments, the attachment can be to a flat plate, as described, for example, in connection with FIG. 2 of U.S. patent application Ser. No. 11/507,733, now U.S. Pat. No. 9,285,297.

Figure 13:
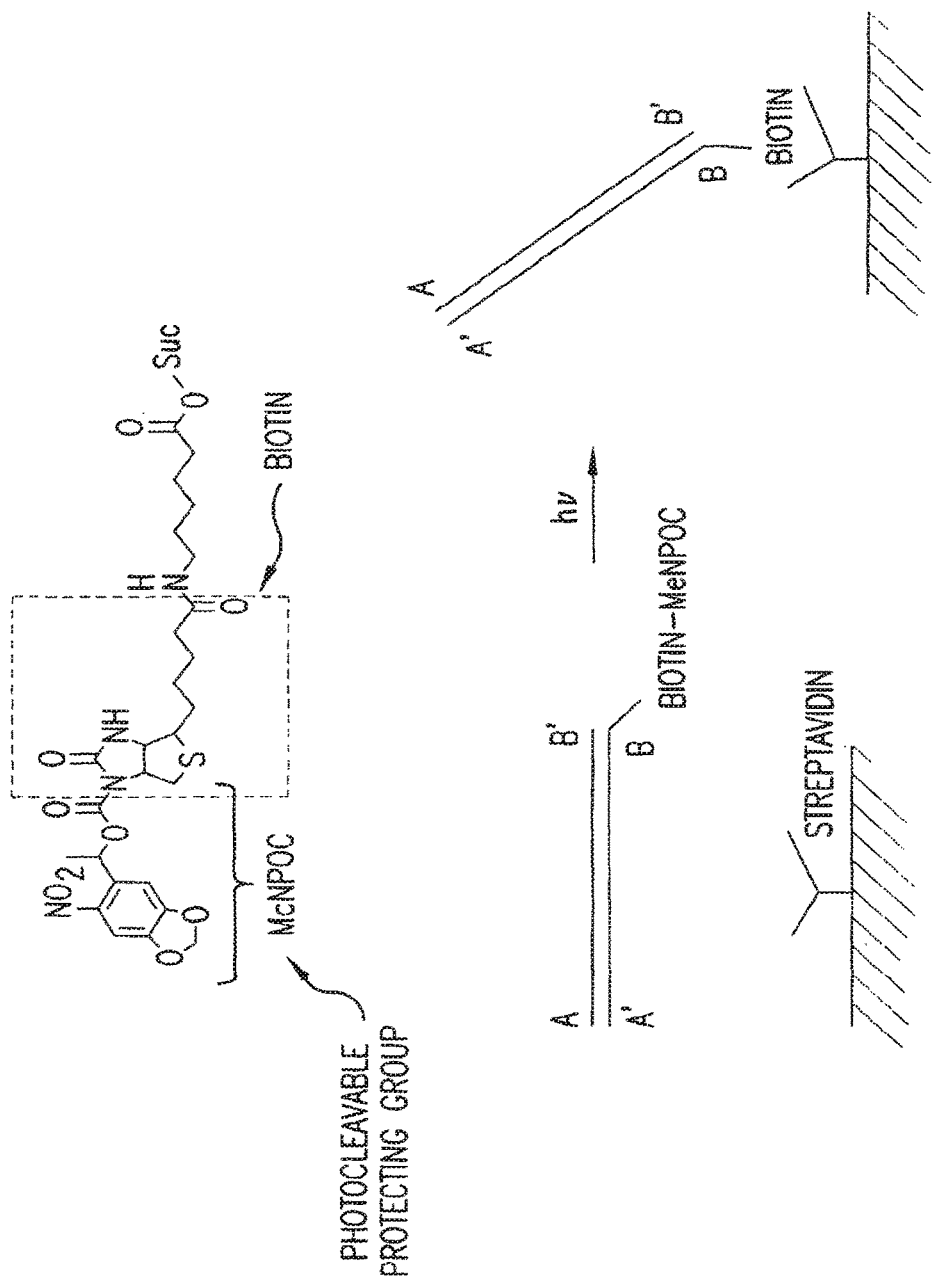
FIG. 13 illustrates a chemistry related to an immobilization of a PCR product in a conduit.

According to various embodiments, light can be used to deprotect a PCR reaction product comprising a "caged" moiety in order to attach a nucleic acid to the inner wall of the conduit. As illustrated in FIG. 13, "caged" biotin can be attached to DNA while amplifying a DNA molecule during a PCR reaction, for example, by using a primer having a caged biotin attached to one end of the oligonucleotide. The caged biotin can be a protected form of biotin that does not bind to streptavidin. Upon deprotection by UV light, biotin can regain it's affinity to streptavidin. An exemplary method for immobilizing a nucleic acid can be found, for example, in Bioconjugate Chem. 317:317-321 (1996), herein incorporated in its entirety by reference. In some embodiments, caging of biotin is not used but instead opto-electro-wetting is used to cause wetting of a conduit wall. In such embodiments, opto-electro-wetting can cause an immiscible-fluid-discrete-volume in a conduit to wet-out on the inner surface of the conduit and binding can be avoided until the opto-electro-wetting field is activated. Further details about generating such a voltage and the manipulation of fluid droplets by electro-wetting can be found, for example, in U.S. Pat. No. 6,629,826 B2 to Yoon et al., U.S. Pat. No. 6,958,132 to Chiou et al., and U.S. Pat. No. 6,911,132 to Pamula et al., each of which is incorporated herein in its entirety by reference.

According to various embodiments, a three component biotin-avidin-biotin linkage can be used. A biotin molecule can be first attached to a conduit surface. The surface can be treated with (3-amino-propyl)trimethoxysilan (3-ATPS)). The biotin molecule can then bind to an avidin, for example, streptavidin, and the avidin can bind to a biotin-modified oligonucleotide.

As illustrated in FIG. 12, following attachment, amplicons can be washed with NaOH to denature double-stranded molecules and a primer can be annealed to attached single-stranded amplicons by flowing appropriate reagents through the conduit. The attached amplicon can then be ready for stepwise sequencing. Conditions relating to stability and denaturation of attached DNA can be found, for example, in Soper et al., Anal. Chem. 70:4036-4043 (1998), which is herein incorporated, by reference, in its entirety. In various embodiments, the sample can be denatured and this can then be followed by flowing in the primers to be used in the annealing. In some embodiments, voltage, as opposed to light, or both, can be used to form an activating field useful for causing wetting-out of an aqueous sample on the inner surface of a conduit.

FIG. 13 illustrates chemistry of immobilization of a PCR product in a conduit using a caged biotin. A caged biotin comprising MeNPOC, a photocleavable protecting group, can be incorporated into an oligonucleotide. The caged biotin-comprising oligonucleotide can be exposed to an appropriate wavelength of light to form an oligonucleotide comprising an unprotected biotin. The biotin-comprising oligonucleotide can then bind to streptavidin attached to the inner wall of a conduit to form an attached oligonucleotide or attached amplicon. According to various embodiments the conduit, for example, a fused-silica conduit, can be derivatized with (aminoalkyl)silane prior to attachment of a nucleic acid. In various other embodiments, a conduit to which an amplicon is to be attached can comprise underivatized fused-silica, polytetrafluoroethylene, or the like. The conduit can comprise a transparent tube or a microchannel plate.

Figure 14:
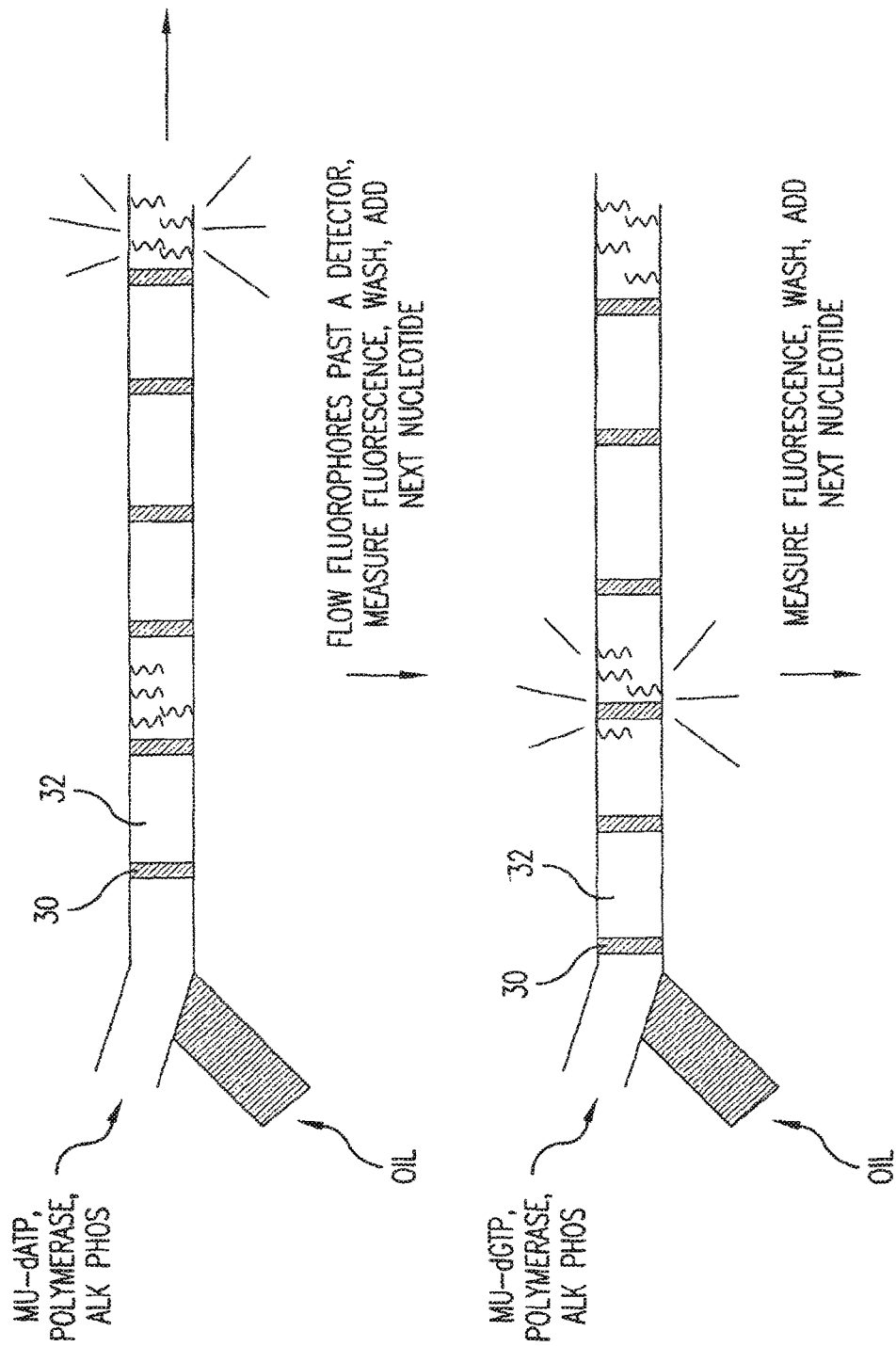
FIG. 14 illustrates a stepwise sequencing procedure in a conduit.

As illustrated in FIG. 14, reagents in an aqueous immiscible-fluid-discrete-volume 1032 can be flowed past an attached amplicon. The aqueous immiscible-fluid-discrete-volume can comprise a fluorophore, for example, 4-methylumbelliferyl-dATP, a polymerase, and an alkaline phosphatase. Alternative embodiments can comprise individual reagents in separate aqueous immiscible-fluid-discrete-volumes as determined by one of skill in the art based on results that one wishes to obtain. For example, an individual immiscible-fluid-discrete-volume can comprise a reagent for incorporation of a fluorophore, and additional immiscible-fluid-discrete-volumes can comprise alkaline phosphatase. In some embodiments, voltage, light, or both, can be used to form an activating field useful for causing wetting-out of an aqueous sample on the inner surface of a conduit, in the absence of which contamination of an attached amplicon can be avoided. Contamination can be avoided by preventing an aqueous liquid containing contaminants from wetting-out onto such an inner surface. Further details about generating such a voltage and the manipulation of fluid droplets by electro-wetting can be found, for example, in U.S. Pat. No. 6,629,826 B2 to Yoon et al., U.S. Pat. No. 6,958,132 to Chiou et al., and U.S. Pat. No. 6,911,132 to Pamula et al., each of which is incorporated herein in its entirety by reference.

According to various embodiments, a fluorophore-labeled nucleotide can bind or be incorporated into a complimentary sequence and fluorescence can be detected. Following detection, a fluorophore containing mixture or solution can be washed out of the conduit. In various embodiments, a solution to wash out the fluorophore can comprise an aqueous immiscible-fluid-discrete-volume that follows the fluorophore-containing immiscible-fluid-discrete-volume. Alternatively, in various embodiments, an entire conduit can be washed out between each newly added batch of fluorophore-labeled nucleotides. The process can be repeated until sufficient sequence information is obtained concerning the attached amplicon. DNA sequencing of an amplicon attached to an inner wall of a conduit using immiscible-fluid-discrete-volumes in a conduit can provide a convenient method of processing or analyzing small volumes. The addition of reagents can be performed by flowing immiscible-fluid-discrete-volumes past attached amplicons. Immiscible-fluid-discrete-volumes can be moved sufficiently slowly to allow their reagents to react with the attached sample. Excess template, primer, and salts can be washed out of the conduit as immiscible-fluid-discrete-volumes comprising the reagents move past the bound amplicon. Alternatively, additional aqueous immiscible-fluid-discrete-volumes can be flowed past an attached amplicon in order to wash out excess reagent.

According to various embodiments, immiscible-fluid-discrete-volumes containing each labeled base can be individually flowed past the attached amplicon. Following incorporation of the labeled base, the signal can be detected and the next base can be flowed past the amplicon. In some instances, multiple bases can be incorporated at the same time.

Figure 15:
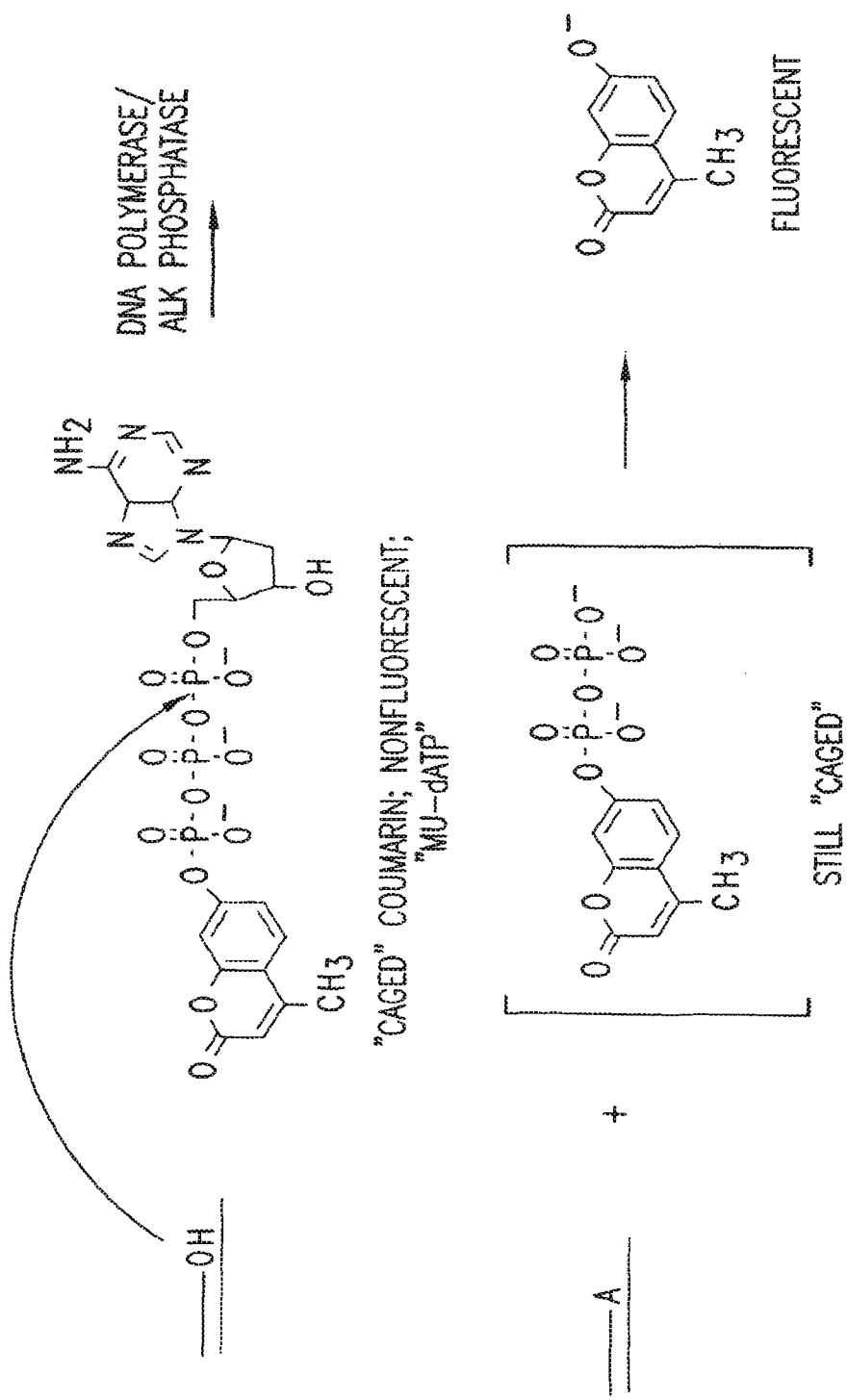
FIG. 15 illustrates a chemistry related to a use of a caged dye for stepwise sequencing.

FIG. 15 illustrates chemistry involved in stepwise fluorescent sequencing using gamma-labeled triphosphates with "caged" dyes (GE/Amersham). When a "caged" coumarin, nonfluorescent nucleotide becomes bound and thereafter becomes uncaged, the fluorescence of a labeled oligonucleotide can be detected. According to various embodiments, the methods and systems provided can be used for stepwise sequencing using a caged dye. In various embodiments, a caged dye can be used in methods other than stepwise sequencing.

FIG. 16 illustrates an integrated sample preparation/cycle-sequencing method. Targets can be prepared comprising A-B primers, SYBR green and a polymerase and can be diluted by limiting dilution to a single molecule per given volume. SYBR green, as well as other dyes known in the art can be used as deemed appropriate at other times in the process in order to generate a fluorescent signal to be detected. SYBR green and other dyes produce a change in fluorescent signal upon interacting with double-stranded nucleic acids, thereby permitting the quantitative or qualitative detection of an amplicon in an immiscible-fluid-discrete-volume of interest. Such information about the presence, absence, or quantity of an amplicon in an immiscible-fluid-discrete-volume of interest can be used to determine if further analysis of the immiscible-fluid-discrete-volume is desired. Target samples can be loaded into a conduit 1028 in the form of aqueous immiscible-fluid-discrete-volumes 1032 that are separated from one another by spacing fluid 1030. An amplification of target samples can occur within an aqueous immiscible-fluid-discrete-volume 1032 in a first thermal cycler 1034. In various embodiments, after flowing from thermal cycler 1034 following amplification, the target samples can be flowed past a detector. The target samples can be flowed past a detector either before or after addition of reagents at pumps 1036 or 1042. For example, see additional details in FIGS. 20 and 21. Those aqueous immiscible-fluid-discrete-volumes comprising an amplified target sample, for example, those samples fluorescing due to incorporation of SYBR green can be collected for further processing, while those immiscible-fluid-discrete-volumes that do not fluoresce can be sent to a waste collection. Immiscible-fluid-discrete-volumes that do not fluoresce do not necessarily have to be immediately sent to a waste collection but can instead proceed downstream through a processing conduit and be sent to waste collection at the end of the conduit. If moved all the way through a processing conduit and sent to waste at the end, the processing system can be controlled so that no additional reagents are added to those immiscible-fluid-discrete-volumes that do not fluoresce and no further analysis of such immiscible-fluid-discrete-volumes needs to be undertaken Similarly, immiscible-fluid-discrete-volumes containing amplicons derived from more than one template may also be sent to waste collection or otherwise prevented from being subjected to unnecessary further analysis. Further processing can comprise, for example, depositing each individual aqueous immiscible-fluid-discrete-volumes 1032 into a microtiter plate or microtiter tube, or depositing the aqueous immiscible-fluid-discrete-volume onto an assay chip.

In various embodiments, after flowing aqueous immiscible-fluid-discrete-volumes from the first thermal cycler 1034, shrimp alkaline phosphatase (SAP) and exonuclease, or other inactivating agents, can be added to each aqueous immiscible-fluid-discrete-volume 1032 from pump 1036 to form an extended aqueous immiscible-fluid-discrete-volume 1038 and inactivate the amplification reagents present in each aqueous immiscible-fluid-discrete-volume 1032. A valve 1040 can regulate or control flow of reagents into the aqueous immiscible-fluid-discrete-volumes 1032.

Each addition of reagents to an aqueous immiscible-fluid-discrete-volume 1032 as it flows through a conduit can result in a respective extended immiscible-fluid-discrete-volume 1038 having an increased volume. For the purposes of illustration only, the increase in volume is shown in an exaggerated form in several figures, for example, in FIGS. 16 and 17. In various embodiments, exonuclease and phosphatase can be heat inactivated before adding dNTP's.

As the extended aqueous immiscible-fluid-discrete-volumes 1038 flow through the conduit, sequencing reagents can be added to them via pump 1042 through a valve 1044. While valves 1040 and 1044 are shown in FIG. 16, according to various embodiments, valves need not be used. The resulting further extended aqueous immiscible-fluid-discrete-volume 1046 can then be further processed, for example, a sequencing reaction can then be performed in a second thermal cycler 1047, if required. In some embodiments, the further extended aqueous immiscible-fluid-discrete-volume can be split into two halves, and reagents for a forward sequencing reaction can be added to one half while reagents for a reverse sequencing reaction can be added to the other half. In some embodiments, reagents for a forward sequencing reaction and reagents for a reverse sequencing reaction can both be added to the further extended aqueous immiscible-fluid-discrete-volume with a universal sequence added to only one of the forward primers and the reverse primers. The sequencing reaction products can be detected by a detector 1048 and flowed into a collection chamber or a capillary electrophoresis apparatus 1049 for additional analysis. Samples can be collected, ethanol-precipitated, dissolved in formamide, HiDi-formamide, or deionized water and analyzed on a plate, for example, using capillary electrophoresis. Similar clean-up techniques can be carried out as part of many other processes described herein, for example, in the process depicted in either FIG. 3A or FIG. 12. In various embodiments, for example, an ABI 310, ABI 3130, ABI 3130xl, ABI 3700, ABI 3730, or ABI 3730xl capillary electrophoretic analyzer (available from Applied Biosystems, Foster City, Calif.) can be used for sequencing.

After samples have undergone a sequencing reaction, a sample or processed immiscible-fluid-discrete-volume can be "spit" out or dispensed into a well of a microtiter plate. A dispensed sample can have a volume of about 250 nl. In various embodiments smaller or larger volumes can be spit out.

Detection of a sample can depend on a number of factors that can be varied during the thermal cycling process. According to various embodiments, a sample can be cycled about 50 times in either thermal cycler 1034 or 1047. The number of cycles, however, can be increased or decreased in order to provide information as deemed appropriate to one of skill in the art. Cycle times and temperature per cycle can be adjusted as desired.

According to various embodiments, a single DNA molecule can be amplified in an immiscible-fluid-discrete-volume in a conduit, the amplified DNA molecule can then be attached to the inner wall of a conduit and a sequencing reaction can be performed on the attached DNA using appropriate primers. Results of sequencing reactions can be analyzed while the sequencing product is still attached to a conduit surface. In other embodiments, products of a sequencing reaction can be detached from a conduit surface and flowed downstream, or detected in the system as a quality control to determine which immiscible-fluid-discrete-volumes can be used for sequencing, for example, to be sent to an appropriate apparatus, for example, a capillary electrophoresis apparatus that can provide on-line analysis of sequencing fragments obtained from the sequencing reaction. In various other embodiments, the amplifying of a nucleic acid and its sequencing can be done without the molecule of interest being attached to an inner surface of a conduit surface.

TTP in a PCR reaction mixture can be replaced with dUTP. Such a replacement can permit control of inadvertent cross-over contamination of unwanted amplicons from other sources that could interfere with an amplification of interest. Use of dUTP in a PCR reaction allows for treatment of reaction mixes with uracil-N-gycosylase (UNG) to eliminate cross-over contamination. After UNG treatment, the UNG can be inactivated by heating to an appropriate temperature, for example, in second thermal cycler 1047.

FIG. 17 illustrates an approach to resequencing using a sample loading system.

Aspects of a resequencing protocol, for example, sample preparation for aqueous immiscible-fluid-discrete-volumes, can be similar to de novo sequencing as described for FIG. 16. Aqueous immiscible-fluid-discrete-volumes 1032 each comprising a respective PCR-specific primer pair can be prepared and flowed into a conduit 1028. Prior to flowing into or through a thermal cycler, genomic DNA from pump 1033 can be added to the aqueous immiscible-fluid-discrete-volumes 1032. After, thermal cycling, SAP and exonuclease can be added by pump 1036 to inactivate PCR reagents. Sequencing reagents can be added at pump 1042 and a sequencing reaction can occur whereby the sequencing reaction products are sequenced. Further extended immiscible-fluid-discrete-volumes 1046 comprising a sample can be detected by detector 1048 and flowed into an apparatus 1049 for analysis. Other reference numerals shown in FIG. 17 indicate features corresponding to those in FIG. 16. As in FIG. 16, the volume of the aqueous immiscible-fluid-discrete-volumes can increase with each set of added reagents.

According to various embodiments, pump 1033 can include a pre-amplification chamber whereby preamplification of a target or a group of targets can occur and portions of the preamplified product can be pumped into respective immiscible-fluid-discrete-volumes in a conduit. The method can coordinate timing between immiscible-fluid-discrete-volumes entering and being processed through the system and alignment of addressable locations in or on a collection device, for example, the wells of a multiwell tray. In various embodiments, the method or system can use or comprise a preloaded reagent-containing channel, for example, a conduit comprising preloaded reagents. Exemplary reagents that a conduit can be preloaded with can comprise, for example, zip code primers or target-specific primers. The use of zip code primers can be used in combination with a pre-amplification process and thus require smaller amounts of gDNA. Exemplary pre-amplification processes that can be used in such combination include those described, for example, in U.S. Patent Application No. 60/699,782 to Faulstich et al., filed Jul. 15, 2005, and in U.S. patent application Ser. No. 11/487,729 to Faulstich et al., filed Jul. 17, 2006, which are incorporated herein in their entireties by reference.

According to various embodiments, two immiscible fluids can form small immiscible-fluid-discrete-volumes or isolated or partitioned portions when mixed together. Reactions in partitioned sections have been discussed in U.S. Patent Publication 2004/0180346 to Anderson et al., incorporated by reference herein. Often, the partitioned sections can be found as microdroplets or globules or spheres in a non-constrained volume. Such partitioned sections have been used in various biochemical and molecular biology procedures. Ghadessy et al., Nature Biotech. 22: 755-759 (2004), Dressman et al., Proc. Natl. Acad. Sci. USA 100:8817-8822 (2003), and Utada et al., Science 308:537-541 (2005), all of which are incorporated by reference herein.

FIG. 18 illustrates a "T" junction 1054 that can be used according to various embodiments to generate immiscible-fluid-discrete-volumes spaced apart from one another by spacing fluid. In some embodiments, such a "T" junction 1054 can be used for adding additional reagents to already formed immiscible-fluid-discrete-volumes. "T" junction 1054 can comprise a substrate 1056 and, for example, polytetrafluoroethylene tubing, or fused silica capillaries. Fused silica can be used and can include a polyimide coating. Substrate 1056 can comprise, for example, a plexiglass block. According to various embodiments, an aqueous sample fluid solution 1029 and an oil 1031 can be pumped into the "T" junction 1054 from separate sources through two separate conduits 1050 and 1052, respectively. As the two liquids 1029 and 1031 merge together at "T" junction intersection 1058 they result in a plurality of immisciblefluid-discrete-volumes 1032 spaced apart from one another by oil 1030, and which move into and downstream in conduit 1060. In various embodiments, the pumping of the two liquids can be done simultaneously or alternatingly to result in the spaced-apart immiscible-fluid-discrete-volumes 1032. According to various embodiments, "T" junction 1054 can comprise flangeless fittings, nuts, ferrules, unions, and/or luer fittings. In various embodiments, shapes other than a "T" can be used for the junction, for example, a "Y" junction can be used.

According to various embodiments, material other than polytetrafluoroethylene can be used for the capillaries, tubing, channels, or other conduits described herein. The material can comprise, for example, silicone rubber, glass, butadiene rubber, other rubbers, nylon, fluoropolymer, for example, polyethyleneterephthalate.

According to various embodiments, the at least one aqueous sample fluid introduction unit (not shown) can be in fluid communication with conduit 1050 and at least one spacing fluid introduction unit (not shown) can be in fluid communication with conduit 1052. A control unit can be provided to control the introduction units.

According to various embodiments, downstream conduit 1060 can comprise an inner surface having a maximum inner cross-sectional dimension. The aqueous sample fluid introduction unit and the spacing fluid introduction unit can comprise separate units, each in fluid communication with respective conduits 1050 and 1052. The control unit can be adapted to control flow of an aqueous sample fluid and a spacing fluid from the aqueous sample fluid introduction unit and the spacing fluid introduction unit, respectively, and can be adapted to control injection of volumes of aqueous sample fluid and spacing fluid that respectively form aqueous immiscible-fluid-discrete-volumes in conduit 1060 wherein each immiscible-fluid-discrete-volume comprises an outer dimension that is equal to about 95% or more of the maximum inner cross-sectional dimension.

Fluids can be said to be immiscible in each other when they can be maintained as separate fluid phases under conditions being used. Immiscible fluids can also be said to be incapable of mixing with each other or attaining a homogeneous solution with each other. While oil and water are immiscible in each other, such a combination does not necessarily form aqueous immiscible-fluid-discrete-volumes when mixed or placed together. For example, oil and aqueous solution may merely form droplets or microdroplets in a larger volume but not necessarily an immiscible-fluid-discrete-volume.

Aqueous solutions and oil from separate sources can become a continuous single flowing liquid stream comprising distinct immiscible-fluid-discrete-volumes spaced-apart from one another by the oil and can exhibit a banded or zebra appearance or pattern. Such a pattern can be formed throughout the length of a conduit. In various embodiments, the aqueous immiscible-fluid-discrete-volumes can contain different reagents at different positions at a conduit. In other words, not all aqueous immiscible-fluid-discrete-volumes throughout a conduit or tube need to contain the same reagents.

In various embodiments, the immiscible-fluid-discrete-volumes can comprise solutions comprising DNA or DNA reaction reagents separated from adjacent immiscible-fluid-discrete-volumes by an oil or another liquid that is immiscible with respect to the immiscible-fluid-discrete-volumes. According to other embodiments, the immiscible-fluid-discrete-volumes can comprise non-DNA reagents that are soluble in the aqueous solutions.

Figure 19A:
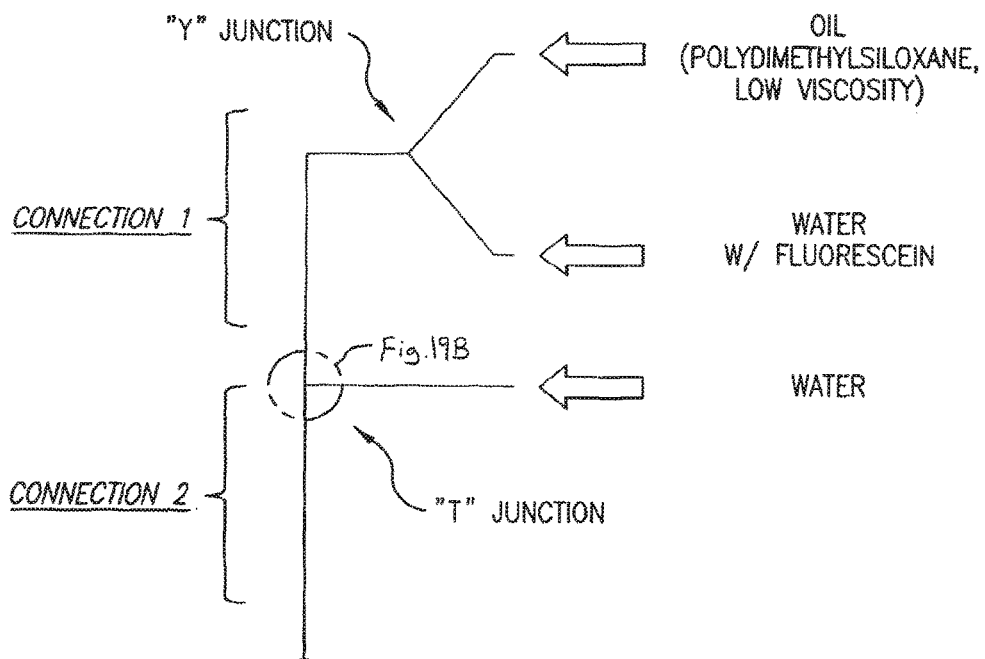
FIG. 19A illustrates a schematic for adding a third liquid to a conduit apparatus for generating aqueous immiscible-fluid-discrete-volumes.

FIG. 19A illustrates an exemplary system that provides the addition of a third liquid during the formation of immiscible-fluid-discrete-volumes. The system comprises a "Y" junction and a "T" junction, although any combination of "T's," "Y's," or other shaped junctions can be used, provided that immiscible-fluid-discrete-volumes can be formed for flowing into a conduit. In various embodiments, additional "T" or Y" junctions can be added to a sample preparation system to add additional reagents to already formed immiscible-fluid-discrete-volumes moving through a conduit, and thus form extended immiscible-fluid-discrete-volumes. The addition of such reagents can increase the volume of the immiscible-fluid-discrete-volume to which the reagent is added resulting in an extended immiscible-fluid-discrete-volume.

Figure 19B:
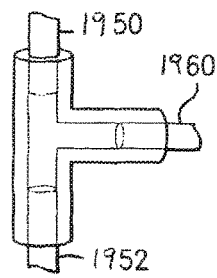
FIG. 19B illustrates an exploded view of a "T" junction.

FIG. 19B provides a close-up perspective view of an exemplary "T" junction formed from three conduits. As shown, conduits 1950 and 1952 form a "T" junction with conduit 1960.

Figure 19C:
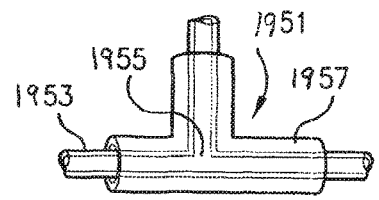
FIG. 19C illustrates an exploded view of "T" junction that can comprise two conduits.

FIG. 19C provides a close-up perspective view of another exemplary T" junction formed from the intersection of one conduit with another conduit. A junction 1951 can be formed with a first conduit 1953 by forming a hole 1955 through first conduit 1953 and through a retaining sleeve 1957 surrounding first conduit 1953.

According to various embodiments, the junction need not necessarily be as illustrated. Rather, the junction can be formed in any manner that provides a meeting of tubes or conduits such that fluid can flow from one conduit into another conduit. Such junctions can be used to form immiscible-fluid-discrete-volumes, dilute sample already in an aqueous segment, and/or to add reagents, solution, or reaction components to an already formed segment. According to various embodiments, an apparatus or system adapted to produce aqueous immiscible-fluid-discrete-volumes spaced-apart from one another by a spacing fluid, for example, by an oil, can be used as the front-end sample preparation procedure for a biochemical or molecular biology method that requires distinct samples having small volumes. Such samples can be, for example, less than about 100 µl, less than about 1 µl, less than about 500 nl, less than about 250 nl, or less than about 50 nl.

Figure 20:
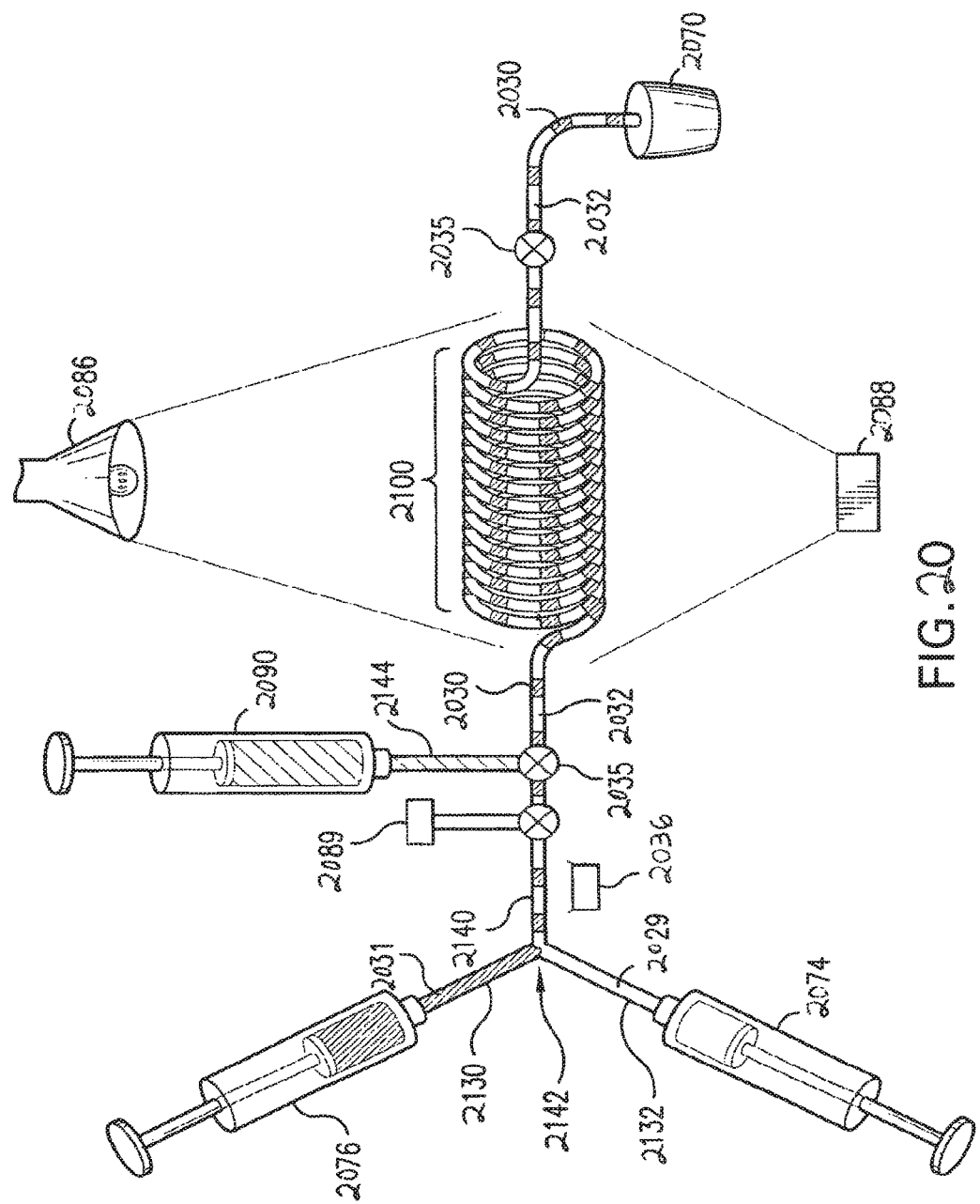
FIG. 20 illustrates a system for sample processing that can be used for step-wise sequencing.

According to various embodiments and as described above, a system is provided that can comprise at least one conduit comprising an inner surface and having a maximum inner cross-sectional dimension, an aqueous sample fluid introduction unit in fluid communication with the at least one conduit, a spacing fluid introduction unit in fluid communication with the at least one conduit, and a control unit adapted to flow an aqueous sample fluid and a spacing fluid from the aqueous sample fluid introduction unit and the spacing fluid introduction unit, respectively, and adapted to inject volumes of aqueous sample fluid and spacing fluid that respectively form immiscible-fluid-discrete-volumes of the aqueous sample fluid spaced-apart from one another by the spacing fluid in the at least one conduit, wherein each immiscible-fluid-discrete-volume comprises a dimension that is equal to at least about 95% the maximum inner cross-sectional dimension. Each of the aqueous sample fluid introduction unit and the spacing fluid introduction unit can comprise a separate unit in respective fluid communication with the at least one conduit FIG. 20 illustrates a system that can be used for stepwise sequencing. The system can comprise pumps 2074, 2076 and 2090, one or more conduits, a source of aqueous sample fluid 2029, a source of oil 2031, valves 2035, energy source 2086, a detecting apparatus 2088, and a waste container 2070. In various embodiments, the system can comprise a detector 2036 that can provide a signal for the signal to use in diverting unwanted sample to waste container 2089. When a detector is used for this purpose, an additional intersection can be inserted into the system that allows diversion of undesired immiscible-fluid-discrete-volumes into waste container 2089. Detector 2036 can either be in-line with the system such that the aqueous immiscible-fluid-discrete-volumes flow directly through the detector, or the immiscible-fluid-discrete-volumes can flow past a detector that is not in-line with the conduit or channel. In any of various embodiments, the system can comprise a detector-diverter system as deemed appropriate and placed wherever it is deemed necessary to discriminate between desired and undesired immiscible-fluid-discrete-volumes and to direct undesired immiscible-fluid-discrete-volumes to a waste container. In some embodiments, an output signal from a detector can be used to control one or more downstream introduction units. Desired immiscible-fluid-discrete-volumes can be detected, for example, by intercalation of SYBR green dye into DNA and the subsequent fluorescent detection of the SYBR green. Spacing fluid and undesired immiscible-fluid-discrete-volumes can be diverted to waste container 2089.

Detection of signals can be achieved using a detecting apparatus 2088, for example, using an optical or fluorescent detection system. For example, fluorescence-based signals can be detected using laser activated or laser induced fluorescence detection systems employing a laser light source emitting at an appropriate wavelength for activating a fluorescent indicator attached to a molecule to be detected. Other detection devices can be used. Fluorescence can then be detected using an appropriate detector element, for example, a photomultiplier tube (PMT) or CCD. Similarly, to detect colorimetric signals, spectrophotometric detection systems can be used comprising a light source, aimed at an immiscible-fluid-discrete-volume, which can provide a measurement of absorbance or transmissivity of the volume. In some embodiments, a refractive index detector can be used. According to various embodiments, a signal generated in the system can be monitored or detected downstream in the system by detecting apparatus 2088.

According to various embodiments, a sample can initially be diluted such that when formed into immiscible-fluid-discrete-volumes of a particular size less than one molecule is present per immiscible-fluid-discrete-volume. Each immiscible-fluid-discrete-volume can comprise, for example, a template sample and PCR reagents. The PCR reagents can comprise, for example, primers labeled at the 5' end with a caged form of biotin, DNA polymerase, magnesium, and buffer.

As shown in FIG. 20, oil 2031 can be pumped into a respective conduit 2130 from pump 2076 and an aqueous sample fluid solution 2029 comprising a target DNA can be pumped into a respective conduit 2132 from pump 2074, to form immiscible-fluid-discrete-volumes of the aqueous sample fluid spaced-apart from one another by the oil and which exhibit a banded or zebra pattern in conduit 2140 downstream of a junction 2142 of the two respective conduits 2130 and 2132.

At the "T" or "Y" intersection aqueous immiscible-fluid-discrete-volumes can be formed by a solenoid acting as a pulsator and pushing against flexible tubing in a pulsed pattern at a specific frequency. The solenoid can be synchronized to one or more rates of flow. Either oil or an aqueous solution can be flowed in the flexible tubing. Small vibrations of the solenoid can create immiscible-fluid-discrete-volumes spaced-apart from one another by the oil spacing fluid. For example, a frequency of 1 khz can be used to pulse the solenoid. Other frequencies, however, can be used as deemed appropriate by one of skill in the art, for a desired analysis. In some embodiments, the frequency can be matched to the rate of formation of an immiscible-fluid-discrete-volume, or it can be a multiple thereof.

The target sample can be amplified to form amplicons by thermal cycling the DNA in the aqueous immiscible-fluid-discrete-volumes at a coiled section 2100 of conduit 2140. The temperature of coiled section 2100 can be maintained or changed in a temperature-controlled environment (not shown). The inner surface of conduit 2140, or portions thereof, can be coated with streptavidin. After thermal cycling, the caged biotin is uncaged with UV radiation emitted from energy source 2086 to form double stranded amplicons attached to the inner surface of the conduit in coiled section 2100. To effect wetting-out of the aqueous immiscible-fluid-discrete-volume for the purpose of facilitating attachment to the inner surface of conduit 2140 and thus to the streptavidin coated thereon, conduit 2140 can be provided with activatable regions configured to cause electro-wetting or opto-electro-wetting of the aqueous immiscible-fluid-discrete-volume. Further details about the manipulation of fluids by electro-wetting can be found, for example, in U.S. Pat. No. 6,629,826 B2 to Yoon et al., U.S. Pat. No. 6,958,132 to Chiou et al., and U.S. Pat. No. 6,911,132 to Pamula et al., each of which is incorporated herein in its entirety by reference.

In some embodiments, a denaturing solution, for example, an NaOH solution, can thereafter be introduced from a pump 2090 through a conduit 2144 and a valve 2035 and into the system in the form of additional aqueous immiscible-fluid-discrete-volumes or as a continuous stream (not shown). The immiscible-fluid-discrete-volumes or stream of the NaOH solution can be flowed past the double-stranded attached amplicons to denature the attached double-stranded amplicons and form single-stranded attached amplicons.

Stepwise sequencing reagents (for example, 4-methylumbelliferyl-dATP, DNA polymerase, alkaline phosphatase) can then be introduced from pump 2074 or from an additional source (not shown), and oil can be introduced from pump 2076, to introduce additional oil spacing fluid and aqueous reagent-containing immiscible-fluid-discrete-volumes 2032 that can be flowed past the attached amplicons in coiled section 2100. Fluorescence released from attached fluorophore-labeled nucleotides can be detected by imaging the conduit with detection device 2088. The system can comprise a separate excitation source 2086 or the excitation source can be part of an integrated detection system. In various embodiments, detection device 2088 can be located downstream of coiled section 2100 of the conduit such that fluorescence can be detected in individual immiscible-fluid-discrete-volumes as they flow past detection device 2088. Excess reagent solution or already analyzed immiscible-fluid-discrete-volumes can be sent to waste collector 2070.

In order to obtain sequence information, the stepwise addition of sequencing reagents and their detection as attached fluorescent nucleotides can be repeated sequentially with 4-methylumbelliferyl-dATP, 4-methylumbelliferyl-dCTP, 4-methylumbelliferyl-dGTP, and 4-methylumbelliferyl-TTP. In various embodiments, the system can detect multiple bases, for example, multiple incorporations of dGTP if the template comprises repeated cytosines ("C"s).

According to various embodiments, methods and apparatus are provided for cycle sequencing. A method is provided comprising contacting an aqueous sample fluid in a conduit with a non-aqueous spacing fluid that is immiscible with the aqueous sample, to form a plurality of discrete volumes of the aqueous sample, herein also referred to as immiscible-fluid-discrete-volumes, separated from one another by the non-aqueous spacing fluid. The aqueous sample fluid can comprise a plurality of target nucleic acid sequences, wherein at least one of the immiscible-fluid-discrete-volumes comprises a first immiscible-fluid-discrete-volume that contains one target nucleic acid sequence. The method can comprise amplifying the target nucleic acid sequence in the first immiscible-fluid-discrete-volume in the conduit to form an amplicon; and subjecting the amplicon to a nucleic acid sequencing reaction in the conduit. FIGS. 21 and 22 illustrate systems that can be used for such cycle sequencing.

Figure 21A:
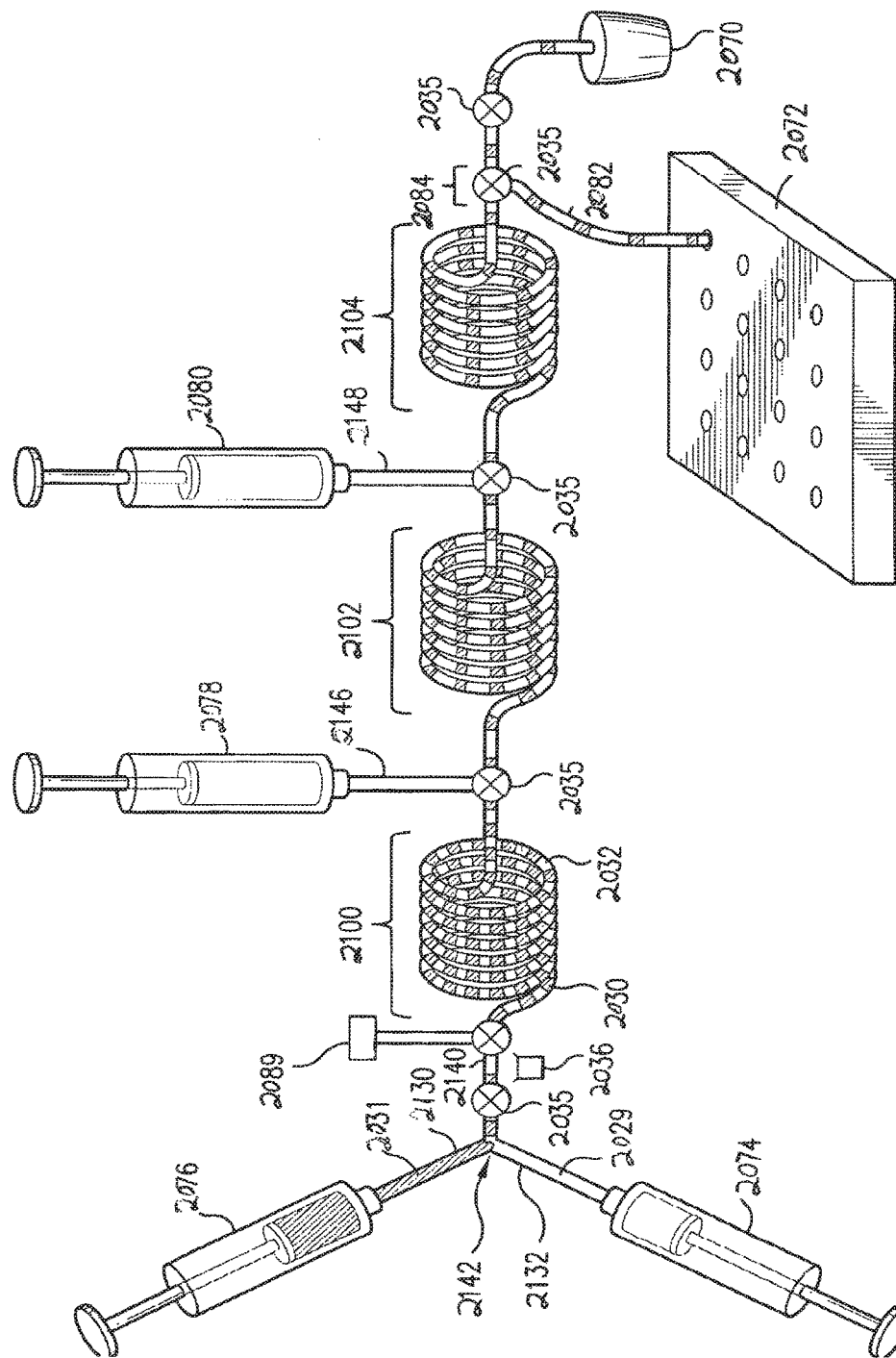
FIG. 21A illustrates a system for sample processing that can be used for cycle sequencing.
Figure 22:
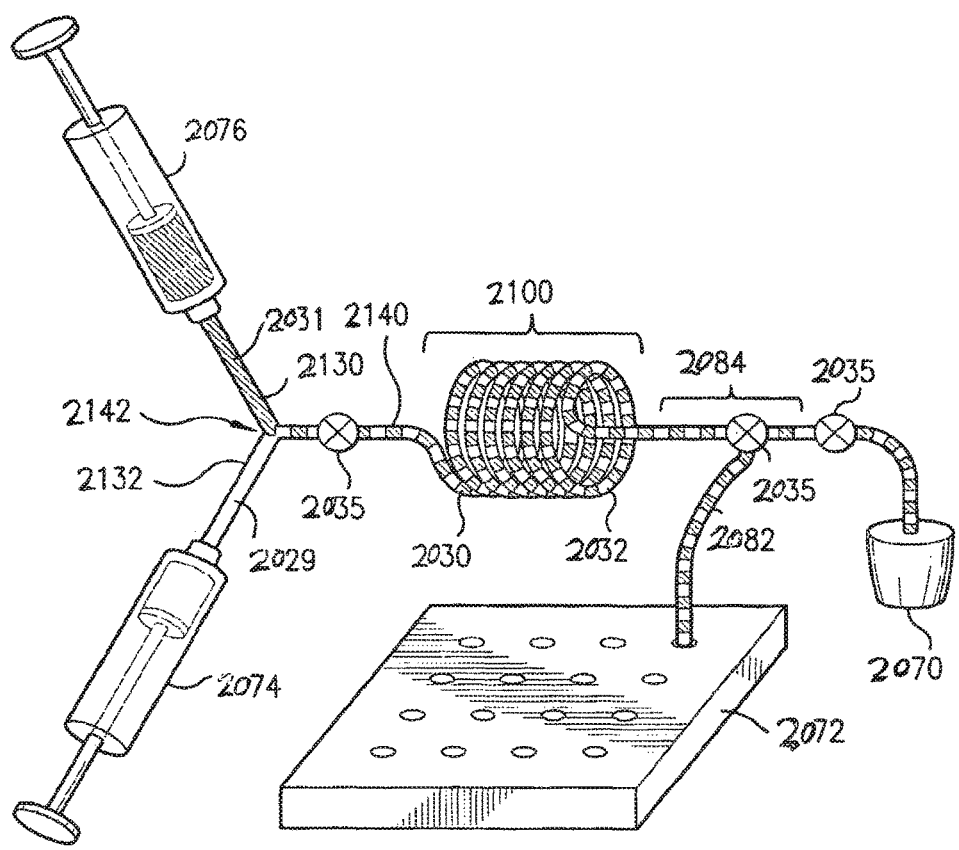
FIG. 22 illustrates a system for nucleic acid amplification.

FIG. 21A illustrates a system that can be used for cycle sequencing. The system can comprise pumps 2074, 2076, 2078, and 2080, one or more conduits, valves 2035, a detecting region 2084, a multiwell plate 2072, and a waste container 2070. Similar to FIG. 20, a detector-diverter system comprising a detector 2036 and a waste container 2089 can be part of the system. Those reference numerals that are the same as the numerals in FIG. 20 represent similar components as shown in FIG. 20. According to various embodiments, immiscible-fluid-discrete-volumes spaced-apart from one another by an immiscible spacing fluid, can be prepared. The sample can be diluted to less than one molecule per aqueous immiscible-fluid-discrete-volume. An aqueous immiscible-fluid-discrete-volume can comprise a template sample and PCR reagents. The PCR reagents can comprise, for example, primers, DNA polymerase, magnesium, buffer, and an intercalating dye.

Oil 2031 can be pumped into a conduit 2130 from pump 2076. Pumps 2074, 2076, 2078, and 2080 can each comprise a servomotor, stepper motor, syringe, piston pump, and/or the like. The temperatures of coiled sections 2100, 2102, and 2104 can each independently be maintained or changed, as deemed appropriate, in a temperature-controlled environment (not shown). An aqueous sample-containing solution 2029 can be pumped into a conduit 2132 from pump 2074. The immiscible-fluid-discrete-volumes resulting from merging the aqueous sample-containing solution and the oil can form a banded or zebra pattern of immiscible-fluid-discrete-volumes downstream of junction 2142 of conduits 2130, 2132. The sample can be amplified to form amplicons by thermal cycling the aqueous immiscible-fluid-discrete-volumes 2032 in coiled section 2100 of conduit 2140.

As aqueous sample-containing immiscible-fluid-discrete-volumes comprising amplicons flow through the tubing, shrimp alkaline phosphatase (SAP) and exonuclease (exo) can be added to the aqueous sample-containing immiscible-fluid-discrete-volumes from pump 2078 through conduit 2146 and its corresponding valve 2035. For example, the aqueous immiscible-fluid-discrete-volumes, including any SAP and exonuclease added thereto, can be incubated for 30 minutes at 37° C. to break down single-stranded DNA and dNTP's, then for 15 minutes at 80° C. to break down the SAP and exo, in coiled section 2102, for example, in a temperature controlled environment or oven (not shown).

After the above treatment, the incubated aqueous immiscible-fluid-discrete-volumes are flowed downstream in conduit 2140 and a solution comprising a forward or reverse sequencing primer, dye terminators, deoxynucleotides, and DNA polymerase (BigDye™ terminators v 3.1—available from Applied Biosystems, Foster City, Calif.) can be added to the incubated aqueous immiscible-fluid-discrete-volumes from pump 2080 through conduit 2148 and its corresponding valve 2035. A cycle sequencing reaction of the incubated, aqueous immiscible-fluid-discrete-volumes can be performed in coiled section 2104 housed in a thermal cycling apparatus (not shown).

After thermal cycling, the resultant aqueous immiscible-fluid-discrete-volumes can exhibit increased fluorescence due to the intercalating dye, that is, an indication that the PCR was positive, which in turn indicates that a template molecule was present and amplified. Alternatively, this can be done prior to introduction of dye terminators. For example, as noted earlier, a detector-discrimination system can be inserted into the system either before or after coiled section 2100.

Each aqueous immiscible-fluid-discrete-volume showing a positive result can be dispensed into multiwell plate 2072 through conduit 2082. At detection region 2084, immiscible-fluid-discrete-volumes that do not demonstrate fluorescence can be directed to waste container 2070. According to various embodiments, a signal generated in the apparatus can be monitored or detected by a detecting apparatus (not shown) disposed adjacent to detection region 2084. While valves 2035 are shown, the system does not have to include any such valves at all. Detecting in detection region 2084 can be used to generate one or more control signals that can be used to locally control the individual valves.

Detection of signals can be achieved using an optical detection system. For example, fluorescence based signals can be detected using laser activated or laser induced fluorescence detection systems employing a laser light source at an appropriate wavelength for activating a fluorescent indicator attached to a molecule to be detected. LED's, halogen bulbs, or other light sources can instead be used. Fluorescence can then be detected using an appropriate detector element, for example, a photomultiplier tube (PMT), photodiode, or CCD. Similarly, detectors adapted to detect colorimetric signals and/or spectrophotometric signals can be employed and can comprise, for example, a light source aimed at an immiscible-fluid-discrete-volume, which can provide a measurement of absorbance, refractive index, and/or transmissivity of the immiscible-fluid-discrete-volume or its contents.

According to various embodiments, nucleic acids in samples from multiwell plate 2072 can be analyzed, for example, using capillary gel electrophoresis, microchip electrophoresis, slab gel electrophoresis, or other analyzers.

According to various embodiments, amplicons from multiwell plate 2072 can be analyzed in a sieving or non-sieving medium. Amplification reactions can also be analyzed by denaturing samples and separating bands of analytes using a capillary electrophoresis protocol, for example, in an ABI PRISM™ 310 genetic analyzer, or by separating bands of analytes on a 4.5%, 29:1 acrylamide:bis acrylamide, 8 M urea gel prepared for an ABI 377 Automated Fluorescence DNA Sequencer, or in a higher throughput florescence-based automated capillary electrophoresis instruments such as the ABI 3100, ABI 3700, and ABI 3730xl (all available from Applied Biosystems, Foster City, Calif.). Sequence data can be analyzed with sequencing analysis Software from Applied Biosystems. In some embodiments of the present teachings, for example, the PCR products or sequencing reaction products can be analyzed by capillary electrophoresis as described in U.S. Pat. No. 5,891,313 to Johnson et al., which is incorporated herein in its entirety by reference. In some embodiments, genotyping can be carried out as described in Wenz, H. et al. (1998) Genome Res. 8:69-80, which is incorporated herein in its entirety by reference. In some embodiments of the present teachings, for example, the PCR products can be analyzed by slab gel electrophoresis as described in Christensen, M. et al. (1999) Scand. J Clin. Lab. Invest. 59(3):167-177, which is also incorporated herein in its entirety by reference. Instead, or additionally, fragments can be analyzed by chromatography (for example, size exclusion chromatography (SEC)).

Figure 21B:
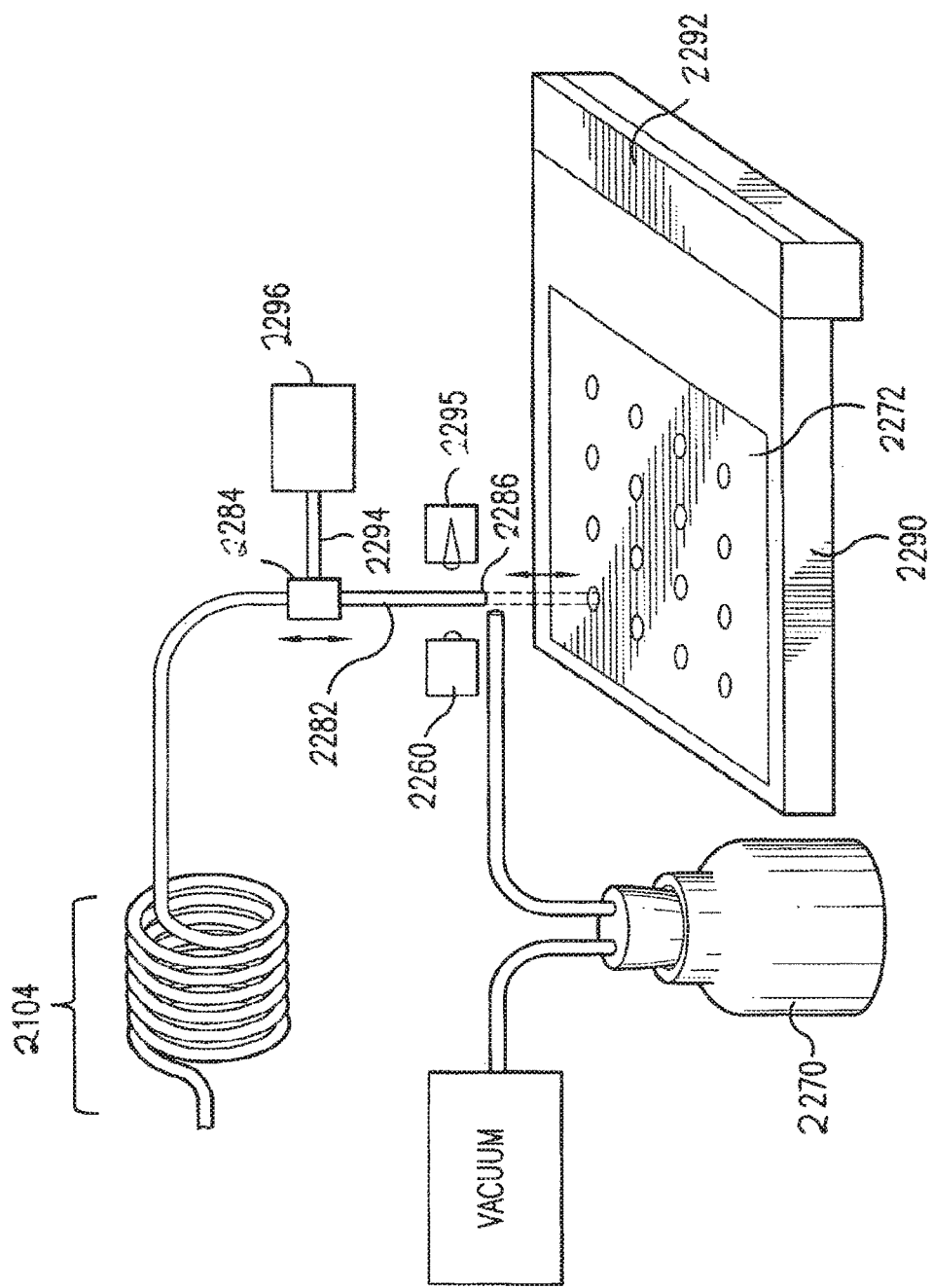
FIG. 21B illustrates a device for collecting samples and waste following cycle sequencing.

According to various embodiments as exemplified in FIG. 21B, a device for sample collection is provided that can be used with the system described above. Such a system can also be used in other embodiments as deemed appropriate by one of skill in the art. Coiled section 2104 as illustrated in FIG. 21A can connect to a sample collection device. In the exemplary system shown, a drive arm 2294 and a conduit holder 2284 can together position a conduit end 2286 in a first position, in a second position, and/or in additional positions. The collection device can comprise an excitation or illumination source 2260 and a detector 2295. A signal from the detector can be used to control drive arm 2294 and drive unit 2296. In some embodiments, excitation source 2260 can comprise a white-light source if, for example, detector 2295 comprises a spectrophotometric detector. Detector 2295 can comprise, for example, a PMT or CCD. At first position, conduit end 2286 can be positioned so that immiscible-fluid-discrete-volumes expelled from conduit end 2286 can be vacuumed into waste receptacle 2270. At the second position, conduit end 2286 can be positioned so that immiscible-fluid-discrete-volumes expelled from conduit end 2286 can be deposited in a receptacle for example, into microtiter plate 2272 as shown. Microtitre plate 2272 can be moved by a carriage 2290 and a drive unit 2292 to align different wells with different respective immiscible-fluid-discrete-volumes expelled from conduit end 2286. In an alternative embodiment, a similar system comprising a diverter can be provided, for example, a controllable, valved "Y" intersection, to direct desired immiscible-fluid-discrete-volumes in a first direction, for example, to a downstream conduit system, and in a second direction, for example, to a waste receptacle. Such a diverter, for example, can be used in the system illustrated in FIG. 21A or FIG. 20 at detector 2036.

FIG. 22 illustrates a system for nucleic acid amplification. The system is similar to that illustrated in FIG. 21A and uses the same numerical designations as FIG. 21A, however, the additional thermal cycling areas, for example, coiled sections 102 and 104 are eliminated. In various embodiments, the system can be used for PCR, oligonucleotide ligase reactions, or any methods comprising multiple small volume samples. Detection of PCR products in real-time can be carried out with a real-time PCR detector, for example, a 7900HT real-time PCR detector (Applied Biosystems, Foster City, Calif.), for example, inside coiled sections 102 and 104, or in a multi-well tray after aqueous sample small volumes have been processed and discharged from the conduit.

Figure 23:
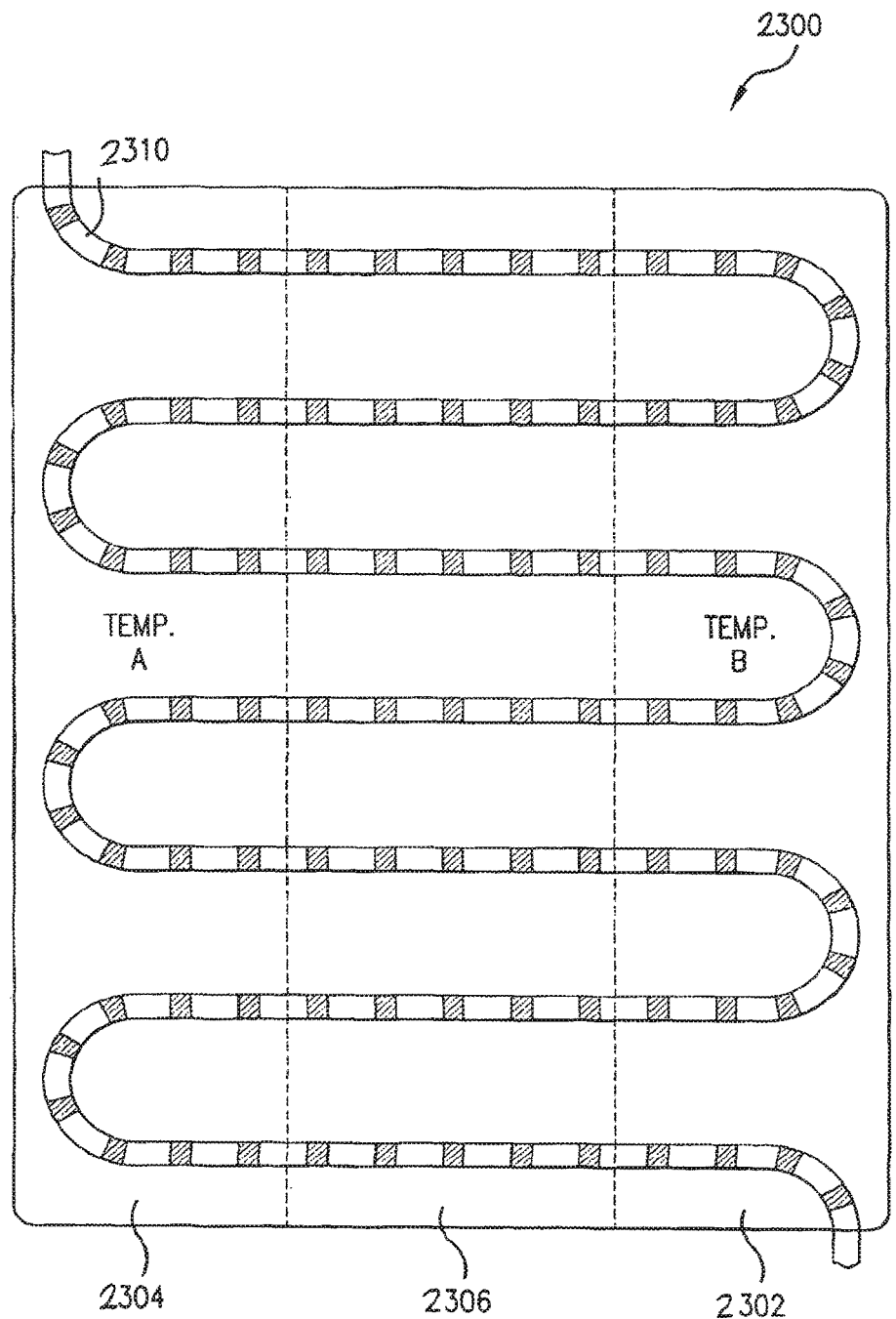
FIG. 23 illustrates a thermal block device for use in various embodiments.
Figure 24:
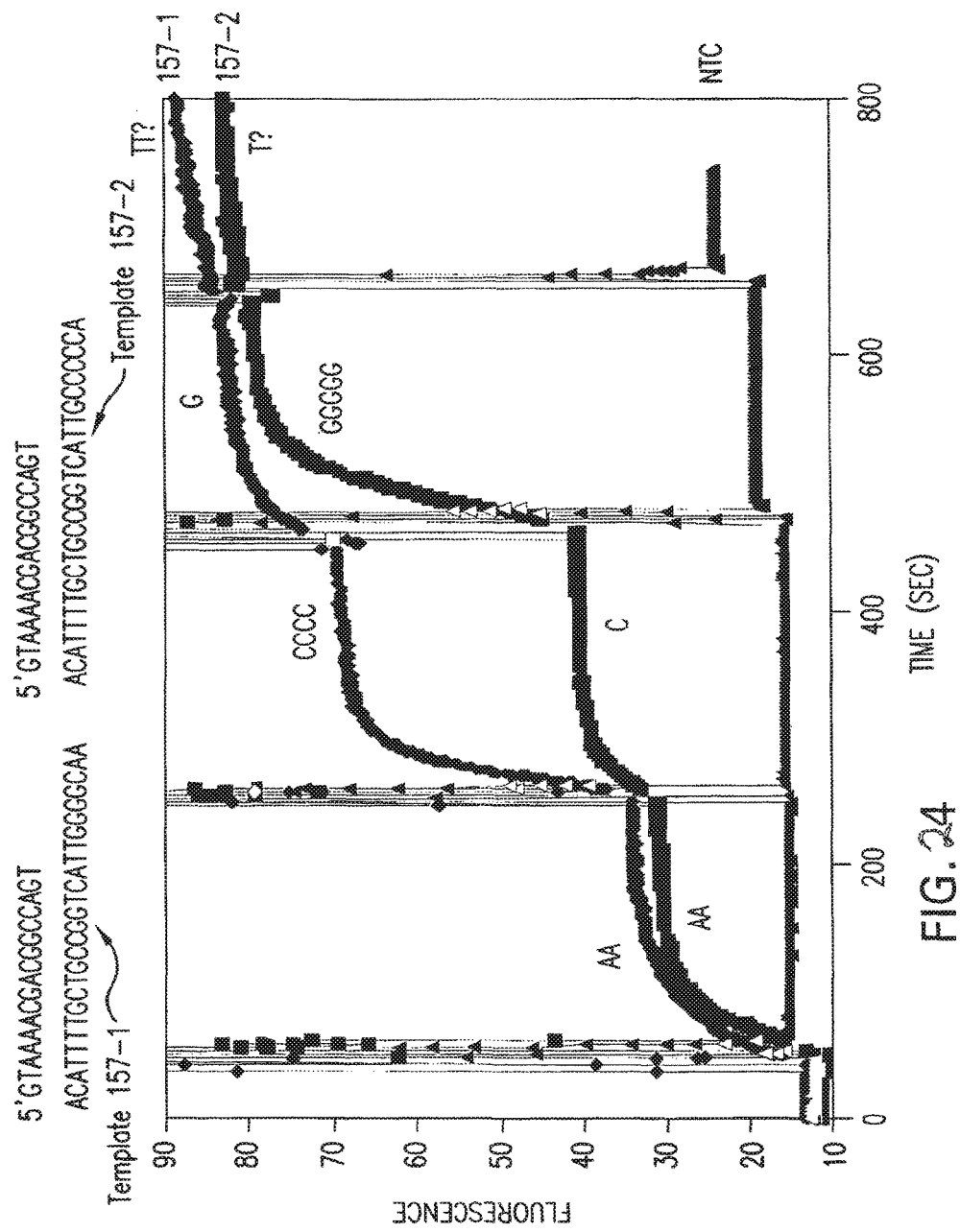
FIG. 24 illustrates step-wise sequencing results obtained in a fluorometer.
Figure 25A:
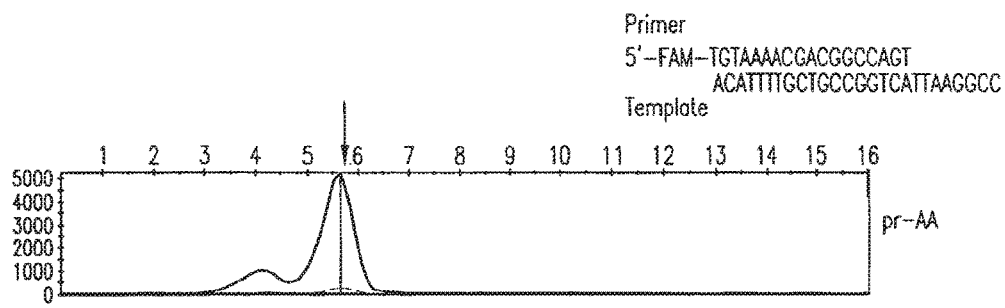
FIGS. 25A-25D illustrates stepwise sequencing results obtained in an Applied Biosystems 3130 sequencer.
Figure 25B:
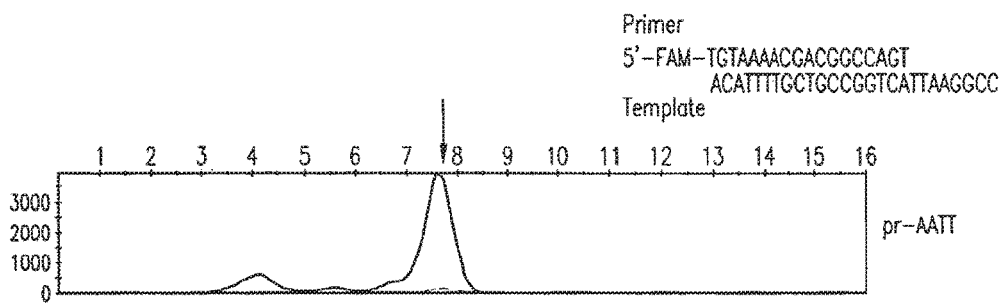
Figure 25C:
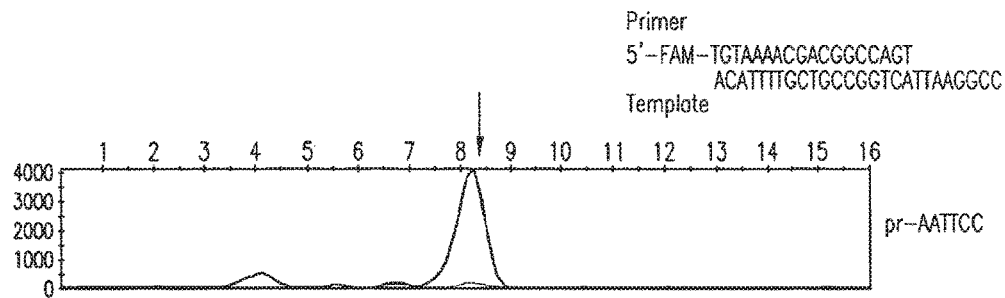
Figure 25D:
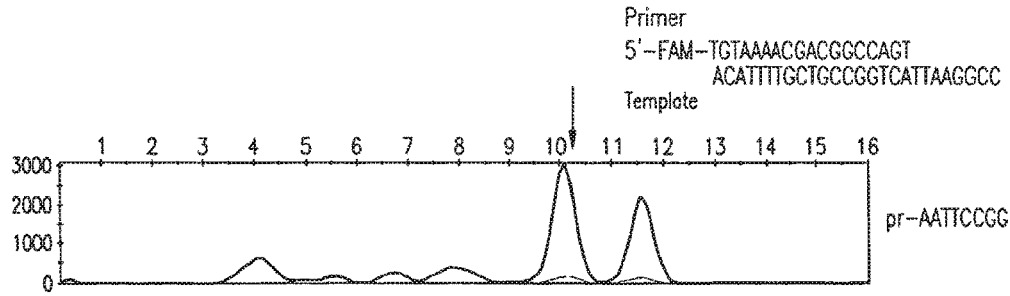

FIG. 23 illustrates a thermal device 2300 that can be used according to various embodiments of the present teachings. Thermal device 2300 can be used in conjunction with or replace various thermal cycling devices or temperature controlled environments, for example, at coiled sections 2100, 2102, or 2104 of the system depicted in FIG. 20 or FIG. 21A. According to various embodiments, thermal device 2300 can comprise thermally conducting blocks 2302 and 2304, and a thermally insulating block 2306. Other arrangements of thermally conducting and thermally insulating blocks can also be used as deemed appropriate. Thermally conducting blocks 2300 and 2302 can comprise, for example, stainless steel, aluminum, other metal materials, a thermally conductive polymer, a polymer filled with thermally conductive filler, or the like.

Thermal device 2300 can comprise a conduit 2310. Conduit 2310 can be used directly for reactions or a second conduit can be placed on thermal device 2300 in conduit 2310. For example, thermal device 2300 can comprise a grooved channel for accommodating conduit 2310 as illustrated, or can comprise a conduit formed therein, for example a covered channel, and appropriate fittings for communication with a conduit. Thermal blocks 2302 and 2304 can comprise heating fluid channels formed therein or can be heated by other heating devices, such as by convective heat, conductive heat and/or radiant heat. For example, one or more Peltier devices can be used to heat thermal blocks 2302 and 2304. Temperatures can be adjusted as deemed appropriate by one of skill in the art for the method of interest. For example, Temperature "A" can be 65° C., while Temperature "B" can be 94° C.

According to various embodiments, a thermal device can comprise any configuration that will permit regulation of different temperatures as required for the reactions or analyses of interest. Such regulation can be produced, for example, by heating an aqueous immiscible-fluid-discrete-volume in place and changing temperatures of the stationary immiscible-fluid-discrete-volume, or by flowing an aqueous immiscible-fluid-discrete-volume through different temperature regulating devices. For example, two different temperature controlled plates can be used and a conduit can be placed between them. Alternatively a conduit can loop through an oven or plates having different temperatures. In various embodiments, a conduit can wrap around a cylinder having different temperature zones.

Figure 27:
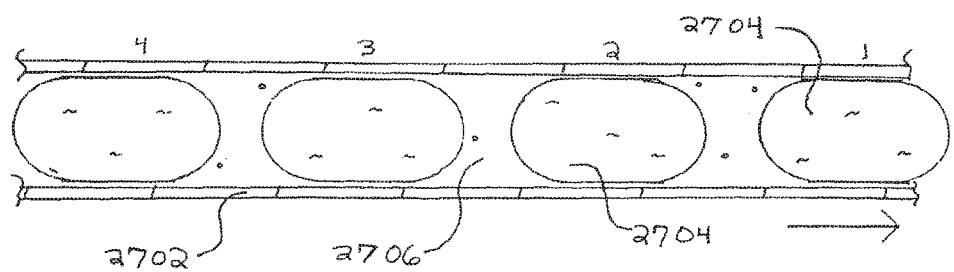
FIG. 27 is a cross-sectional view of a conduit having therein a plurality of slugs of a set.

As shown in FIG. 27, according to various embodiments of the present teachings, a set of immiscible-fluid-discrete-volumes 2704 can be generated according to various techniques described herein, to create a series of aqueous sample fluid or other discrete fluid volumes. According to various embodiments as shown in FIG. 27, the immiscible-fluid-discrete-volumes 2704 can be separated by a spacing fluid 2706, such as oil. According to embodiments as also illustrated in FIG. 27, the immiscible-fluid-discrete-volumes 2704 can be formed in a conduit 2702, such as a capillary, tube, microfluidic channel, groove, electro-wetting path, or other fluid path or conduit.

According to various embodiments in one regard, tracking and identification of individual samples within a sequence of immiscible-fluid-discrete-volumes 2704 is of significant importance in high-throughput parallel sample processing, for example such as PCR cycling, and other sample processing applications. For a series of individual volumes formed or transmitted in conduit 2702, it is helpful or necessary to specify and track the identity of each individual fluid volume entity or groups of associated volumes. One technique for the identification of individual volumes formed in conduit 2702 is to number or label immiscible-fluid-discrete-volumes 2704, for example by ordinal numbering from a fiducial marker or reference point. According to embodiments as illustratively shown in FIG. 27, an example for the ordering of immiscible-fluid-discrete-volumes 2704 is to consider the first fluid volume in immiscible-fluid-discrete-volumes 2704 to be the first of a series, and number the volumes following that volume (labeled volume 1) in order with reference to that initial volume. Thus for example, in a conduit 2702 containing 100 individual volumes, each individual volume can have a unique number starting from a first volume of immiscible-fluid-discrete-volumes 2704 to the last, creating a sequence: 1, 2, 3, 4, . . . , 100.

Figure 28:
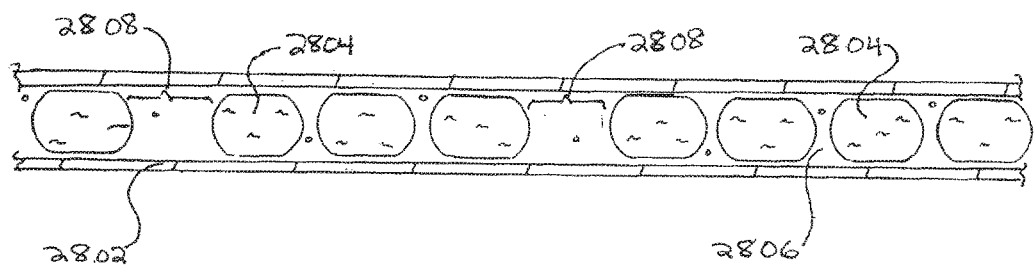
FIG. 28 is a cross-sectional view of a conduit having therein a plurality of sets of slugs and showing fiducial markers between the sets.

According to various embodiments, a fiducial marker or reference point can generally be generated with or represented by various physical characteristics of immiscible-fluid-discrete-volumes 2704, spacing fluid 2706, or their combination to encode information regarding the identity, content, origin, or other characteristics of each or a group of the immiscible-fluid-discrete-volumes 2704. As used herein, "fiducial marker" or "fiducial markers" can refer to any marker, identifier, reference point, calibrating point, reporter, label, tag, or other marker or markers. As shown in FIG. 28, fiducial markers 2808 can, for example, be included within a sequence of immiscible-fluid-discrete-volumes 2804 separated generally by spacing fluid 2806, such as oil, in a conduit 2802. According to embodiments as illustrated in FIG. 28, the spacing, length, or amount of oil 2806 interposed between different groupings of immiscible-fluid-discrete-volumes 2804 can be used to form fiducial markers 2808. That is, according to embodiments as shown, the immiscible-fluid-discrete-volumes 2804 can generally be separated by a nominal, comparatively short, regular distance. Between sets of immiscible-fluid-discrete-volumes 2804 having distinct identities or other characteristics or groupings, however, a longer spacing of spacing fluid 2806, such as a length of spacing fluid 2806 that is twice as great, or more or less, as the nominal regular spacing, can be interposed between the groups of immiscible-fluid-discrete-volumes 2804 to create or form fiducial markers 2808. Thus, the length of spacing fluid 2806, the length of individual aqueous volumes in immiscible-fluid-discrete-volumes 2804, or the length of the combination of spacing fluid 2806 and immiscible-fluid-discrete-volumes 2804, can be used to create, form, or represent fiducial markers 2808.

In embodiments as shown, the spacing of spacing fluid 2806 between groups of immiscible-fluid-discrete-volumes 2804 forms or defines fiducial markers 2808. In the case of individual fluid volumes in a conduit 2802 that are uniformly spaced, a variation in the length of spacing fluid between immiscible fluid volumes provides an identification of a fiducial marker point, for instance, from which fluid volume numbering can be referenced.

As shown in FIG. 29, for example, according to various embodiments, groups of immiscible-fluid-discrete-volumes 2904 separated by fiducial markers 2920 formed as lengths of spacing fluid 2906 in conduits 2902 can represent different batches, groups, or sets of fluid volumes, for instance, groups of aqueous volumes containing different samples, treated with different primers, or otherwise associated or identified as a set. According to various embodiments, a deviation in the length of spacing fluid 2906 between individual fluid volumes of immiscible-fluid-discrete-volumes 2904 from the nominal regular spacing can be used, for example, to define fiducial markers 2920, or more generally, encode information into the fiducial makers 2920 related to associated fluid volumes or other entities. According to various embodiments, conduits 2902 can be, for example, separate conduits, or can be one conduit configured in a looping configuration (not shown), such as a capillary arranged in a S-shaped configuration.

As shown in FIG. 30, according to embodiments of the present teachings, rather than or in addition to using the length of the spacing fluid, the length of selected individual fluid volumes in a set of immiscible-fluid-discrete-volumes 3004 can be used to form or define fiducial markers 3012. According to embodiments as shown in FIG. 30, conduit 3002 can receive a set of immiscible-fluid-discrete-volumes 3004, each discrete aqueous volume of which can have a defined nominal length. According to embodiments as shown, the size or length of selected individual fluid volume in immiscible-fluid-discrete-volumes 3004 can be enlarged, reduced, or otherwise altered to act as fiducial markers 3012. According to various embodiments, the length of fiducial markers 3012 can thereby be a parameter representing the identity of the fiducial markers 3012, immiscible-fluid-discrete-volumes 3004, or associated fluid volumes.

Figure 31:
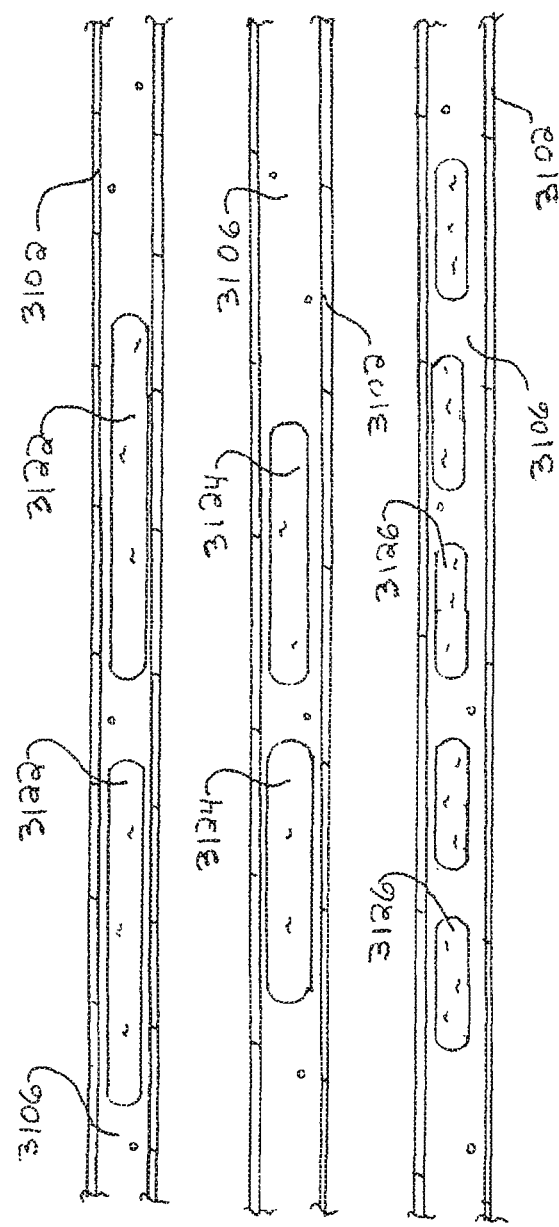
FIG. 31 is a cross-sectional view of three conduits each having therein a different set of slugs, wherein the length of each slug of a set of slugs is the same as the lengths of the others in the set, and the length is different than the length of each slug of a different set of slugs.

As shown in FIG. 31, according to various embodiments of the present teachings, a set of immiscible-fluid-discrete-volumes 3122, immiscible-fluid-discrete-volumes 3124, and immiscible-fluid-discrete-volumes 3126 can each be formed by individual fluid volumes having a different nominal length for each set. According to various embodiments as shown, each volume in the immiscible-fluid-discrete-volumes 3122 can have a first length, each volume in the immiscible-fluid-discrete-volumes 3124 can have a second, illustratively shorter, length, and each volume in immiscible-fluid-discrete-volumes 3126 can have a third, again shorter length. According to various embodiments, separate batches of aqueous or other fluid volumes can therefore be identified and tracked, without the necessity of separate fiducial markers in the form of elongated spacing fluid. According to various embodiments in one regard, if two or more fluid volumes merge, a longer fluid volume will result which also reduces the total number of fluid volumes by one less than the number that merged. This activity does not prevent the other fluid volumes from being identified by their ordinal count or other identification or numbering, for example, their numbering from either end or both ends of a set of immiscible-fluid-discrete-volumes.

Figure 32:
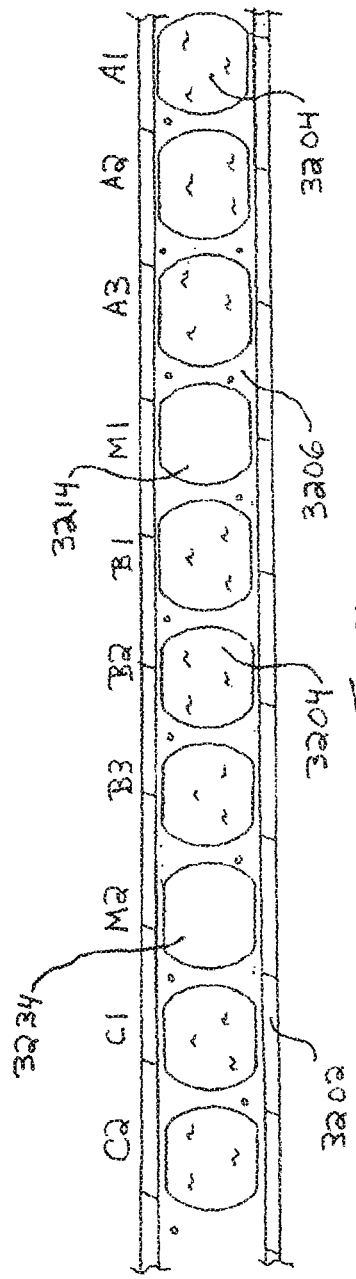
FIG. 32 is a cross-sectional view of a conduit having therein a plurality of sets of slugs and showing fiducial markers between the sets, wherein each fiducial marker has a different reporter molecule than one or more other fiducial markers.

As shown in FIG. 32, according to various embodiments of the present teachings, besides the lengths of spacing fluid and individual fluid volumes, and their relative spacing, the content, physical, or chemical characteristics of individual fluid volumes can also be used to form fiducial markers 3234. As shown in FIG. 32, a set of immiscible-fluid-discrete-volumes 3204 can be generated in spacing fluid 3206, such as oil, separated by first fiducial marker 3214 and second fiducial marker 3234, each in the form of fluid volumes loaded with reporter molecules. The reporter molecules loaded in first fiducial marker 3214 and second fiducial marker 3234 can, for example, each provide unique signals to discern the identity of associated fluid volumes. Reporter molecules that may be provided in each of fiducial markers 3214 and fiducial marker 3234 can comprise, for example, color dye, fluorescent dye, caged dye, quantum dots, particles such as gold, silver, and silicon dioxide, and the like.

Figure 33:
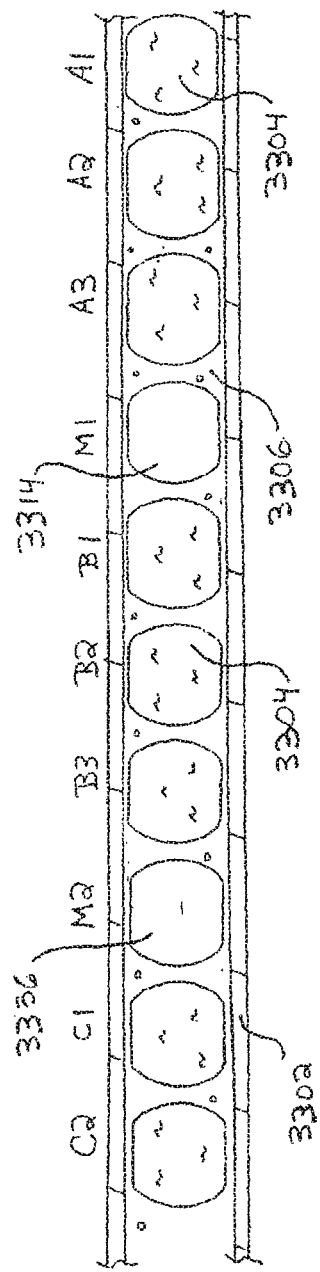
FIG. 33 is a cross-sectional view of a conduit having therein a plurality of sets of slugs and showing fiducial markers between the sets, wherein each fiducial marker has the same reporter molecule as one or more other fiducial markers, but in different concentrations.

According to various embodiments, rather than or in addition to using different reporter molecules in different fiducial markers, a variable level or amount of one reporter loaded into a set of fiducial markers can provide multiple signal identification levels. For example, if fiducial markers 3234 are loaded with FAM fluorescent dye with a concentration of 1×µM, 3×µM, and 6×µM, fiducial markers 3234 can offer three levels of detectable signal due to different emitted fluorescent intensities. Thus, according to embodiments as illustrated in FIG. 33, first fiducial marker 3314 can have a first signal intensity level, while second fiducial marker 3236 can have a second, distinct signal intensity level. As compared to embodiments, for example, illustrated in FIG. 32, according to embodiments illustrated in FIG. 33, the same reporter molecule or other chemical modifier can be used to form different fiducial markers, such as the illustrated first fiducial marker 3314 and second fiducial marker 3336, without the use of separate dyes or other reporter molecules in different fiducial markers.

Figure 34:
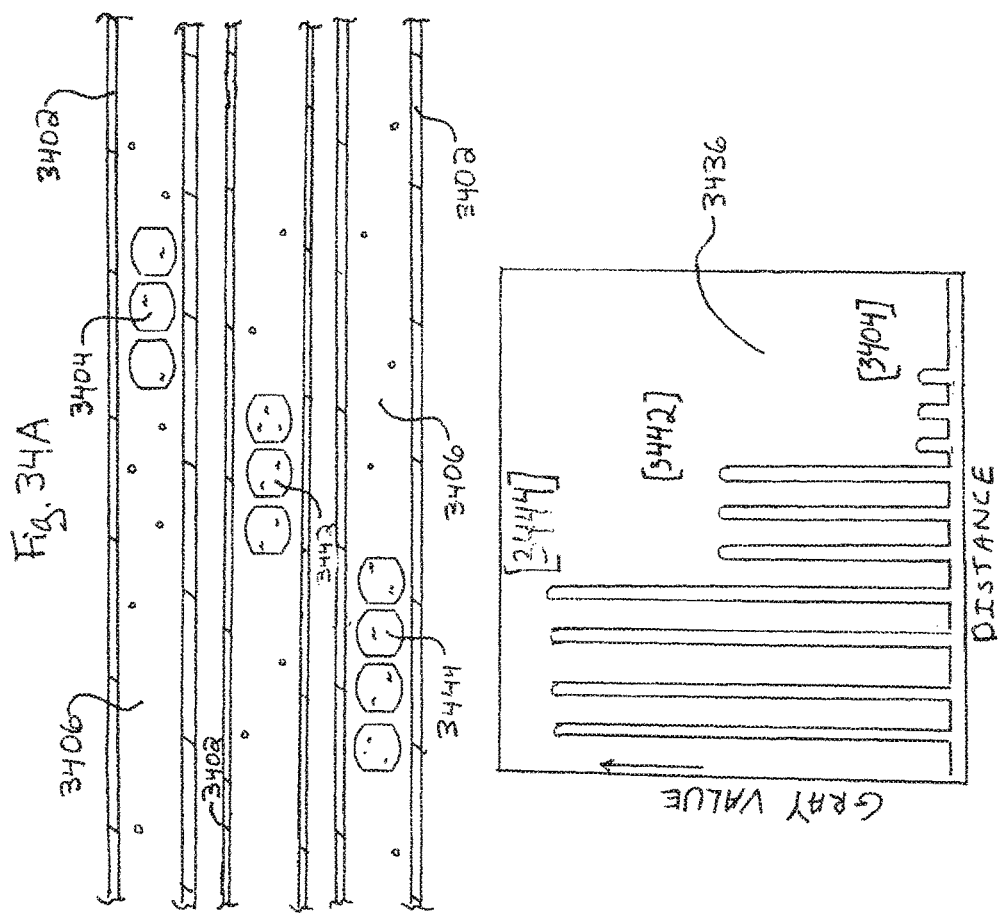
FIG. 34A is a cross-sectional view of three conduits each having therein a different set of aqueous fiducial markers, wherein each set has markers that contain a different concentration of reporter molecules relative to the concentrations in fiducial markers of the other sets.
FIG. 34B is a graph showing the detected reporter intensities exhibited by the fiducial markers shown in FIG. 34A.

According to embodiments of the present teachings as illustrated in FIG. 34A, first fiducial markers 3404 can be loaded with dye or other material to emit a first, comparatively lower intensity value compared to the emitted second signal of second fiducial markers 3442 contained in another batch or set of fluid volumes. Second fiducial markers 3442 in turn emit a lower-intensity signal than the intensity of an emitted third signal of third fiducial markers 3444 illustrated in the lower-most set of immiscible-fluid-discrete-volumes, according to varying reporter concentration. FIG. 34B illustrates a detected signal intensity (shown in gray scale value) corresponding to first fiducial markers 3404, second fiducial markers 3442, and third fiducial markers 3444. According to embodiments as shown in FIG. 34B, separate aqueous sample fluid volumes are not illustrated, for clarity. According to various embodiments as shown in FIG. 34A and elsewhere, aqueous fluid volumes can contain both sample and reporter molecules, or aqueous sample fluid volumes can be generated or maintained as entirely separate fluid objects from fiducial markers.

Figure 35:
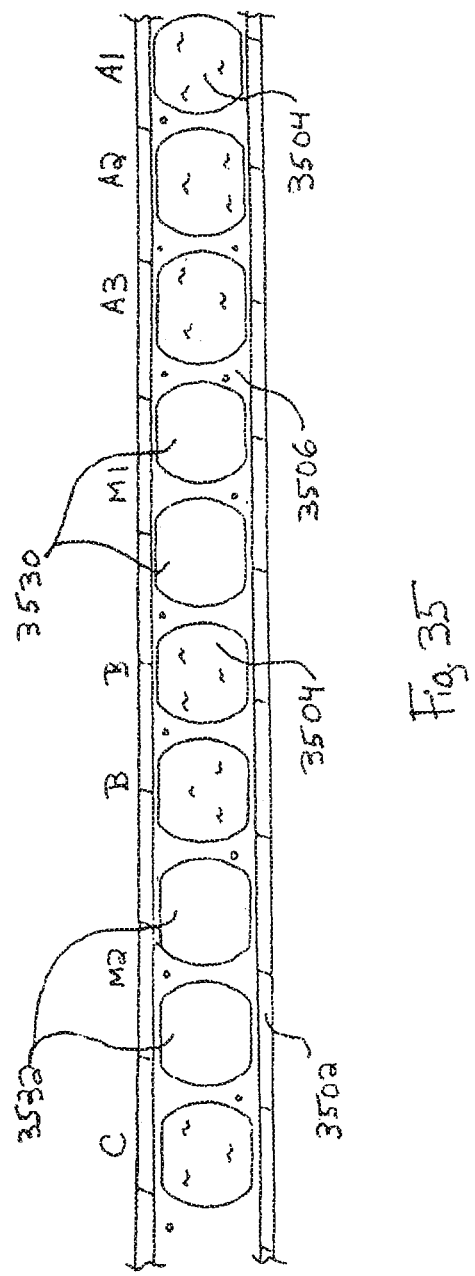
FIG. 35 is a cross-sectional view of a conduit having therein a plurality of sets of slugs and showing fiducial markers between the sets, wherein a pair of aqueous fiducial markers separates each set.

As shown in FIG. 35, according to various embodiments of the present teachings, a fiducial marker system using multiple fluid volumes can be used. According to embodiments as shown in FIG. 35, fiducial markers using two consecutive fluid volumes are illustrated, but it will be appreciated that other numbers of fluid volumes, and fluid volumes that are not consecutive, can also be used. According to embodiments as shown, immiscible-fluid-discrete-volumes 3504 spaced-apart from one another by spacing fluid 3506 can be separated or identified with first fiducial marker 3530 and second fiducial marker 3532, each of which comprises two discrete fluid volumes containing reporter molecules. According to various embodiments, both fluid volumes of each of first fiducial marker 3530 and second fiducial marker 3532 can contain the same reporter molecule or molecules, or can contain different reporter molecules or combinations of reporter molecules. According to various embodiments, the reporter molecules of first fiducial marker 3530 can be the same as the reporter molecules of second fiducial marker 3532, or in various embodiments, the reporter molecule or molecules used in each fiducial marker can be different. If each of fiducial marker 3530 and fiducial marker 3532 is used as a reference for a group of 40 discrete fluid volumes, the number of samples tracked, with a 3-volume and 2-volume fiducial marker system, are 69, 120 and 5,760, respectively.

According to various embodiments of the present teachings, fiducial markers can employ reporter molecules that are activatable to generate signals, rather than fixed in their signal-generating characteristics. For example, fiducial markers using photoactivatable fluorescent dyes that are colorless and non-fluorescent until photolyzed with UV light can be employed. According to various embodiments, examples of commercial caged dye are CMNB-caged carboxyfluorescein and CMNCBZ-caged carboxy-q-rhodamine, which materials are commercially available from Invitrogen. Use of fiducial markers with activatable characteristics permits selective temporal and special resolution of marking operations, through programmable timing and uncaging of the fluid volumes. This, among other things, allows fiducial markers to be generated on-the-fly, instead of using pre-programmed or hard-wired fiducial markers or molecules.

According to various embodiments of the present teachings, in general, the use of multiple reporter molecules to form a fiducial marker each having multiple possible loading or signal levels can provide a higher level of possible unique permutations with which to identify immiscible-fluid-discrete-volumes. The number of unique fiducial markers that can be generated using diverse reporter molecules can be calculated as follows: each reporter molecule j offers $S_j$ number of distinguishable and non-overlapping signals. For example, Rhodamine dye offers 3 signal levels from concentration of 2×μM, 5×μM, 9×μM. If n reporter molecules are used in a fluid volume, the number of unique signals generated is the product of the number of signals each reporter generates $\Pi S_j$, j=1 to n, for each fluid volume. If the number of fluid volumes used as a fiduciary marker is p, the total number of permutations is the quantity ($\Pi S_j$, j=1 to n) raised to the $p^{th}$ power.

From FIGS. 27-35 and the description thereof, it is apparent that the present teachings provide a system comprising a plurality of sample immiscible-fluid-discrete-volumes in a conduit, the immiscible-fluid-discrete-volumes being spaced-apart from one another by a spacing fluid that is immiscible with respect to the immiscible-fluid-discrete-volumes; and at least one fiducial marker, the at least one fiducial marker identifying at least one volume of the immiscible-fluid-discrete-volumes. In some embodiments, the at least one fiducial marker comprises a first spacing between two adjacent sample immiscible-fluid-discrete-volumes of the plurality of sample immiscible-fluid-discrete-volumes that differs from a spacing between two or more other adjacent sample immiscible-fluid-discrete-volumes of the plurality. In some embodiments the at least one fiducial marker comprises an aqueous immiscible-fluid-discrete-volume that is immiscible with the spacing fluid and contains one or more reporter molecules that are not present in the sample immiscible-fluid-discrete-volumes. In some embodiments the at least one fiducial marker comprises two or more aqueous immiscible-fluid-discrete-volumes that are each immiscible with the spacing fluid and that each contain one or more reporter molecules, wherein the concentrations of the reporter molecules are different in the two or more aqueous immiscible-fluid-discrete-volumes. In some embodiments the at least one fiducial marker comprises two or more aqueous immiscible-fluid-discrete-volumes that are each immiscible with the spacing fluid and that each contain one or more reporter molecules, wherein each of the two or more aqueous immiscible-fluid-discrete-volumes contains at least one reporter molecule that is different from at least one reporter molecule in at least one other of the two or more aqueous immiscible-fluid-discrete-volumes.

From FIGS. 27-35 and the description thereof, it is apparent that the present teachings provide a system comprising a first set of immiscible-fluid-discrete-volumes and a second set of immiscible-fluid-discrete-volumes, in a conduit, the immiscible-fluid-discrete-volumes of each set being spaced-apart from one another by a spacing fluid that is immiscible with respect to the immiscible-fluid-discrete-volumes; wherein the immiscible-fluid-discrete-volumes of the first set each have a first length, the immiscible-fluid-discrete-volumes of the second set each have a second length, and the first length and second length are different from one another. In some embodiments, the system can further comprise at least one additional set of immiscible-fluid-discrete-volumes spaced-apart from one another by the spacing fluid wherein each additional set of immiscible-fluid-discrete-volumes is immiscible with the spacing fluid and each immiscible-fluid-discrete-volume of each respective additional set has a length that differs from the first length and the second length.

EXAMPLES

Aspects of the present teachings may be further understood in light of the following examples, which should not be construed as limiting the scope of the present teachings in any way.

Example 1—Stepwise Sequencing

Stepwise sequencing reactions were performed in an Eppendorf tube on sequences using two different synthetic templates 157-1 (TTGGGGAA) and 157-2 (TTGCCCCT). The reaction solution comprised a Tris buffer (tris pH 8.1, $Mg^{2+}$, $Mn^{2+}$, isocitrate), pre-annealed primer/template (0.01 µM/0.04 µM), Klenow (5 U), and shrimp alkaline phosphatase (4 U) in 100 Small volumes (1 µl) of 4-methylumbelliferyl-dATP (20 µM), 4-methylumbelliferyl-dTTP (50 µM), 4-methylumbelliferyl-dCTP (10 µM), and 4-methylumbelliferyl-dGTP (5 µM) were added at intervals of 200 seconds to give final concentrations as indicated in each nucleotide. A control indicated as NTC that contained neither template nor primer was also run in the experiment. Results are shown in FIG. 22. The fluorescent signals illustrate that the complements of the single stranded portions of the template have been determined from a stepwise sequencing reaction. It will be noted that the signal can go off-scale when the fluorometer is opened.

FIGS. 23A-23D provide the results of a similar experiment processed on an Applied Biosystems 3130 sequencer. A final volume of 100 µl was prepared in an Eppendorff tube. The reaction solution comprised a Tris buffer (tris pH 8.1, $Mg^{2+}$, $Mn^{2+}$, isocitrate), pre-annealed primer/template (0.01 µM/0.04 µM), Klenow (5 U), and shrimp alkaline phosphatase (4 U) in 100 µl. Small volumes (1 µl) of 4-methylumbelliferyl-dATP (20 µM), 4-methylumbelliferyl-dTTP (50 µM), 4-methylumbelliferyl-dCTP (10 µM), and 4-methylumbelliferyl-dGTP (5 µM) were added at intervals of 300 seconds to give final concentration of 20 µM in each nucleotide. After each addition, 2 µl was removed and added to 20 µl HiDi-formamide (Applied Biosystems PN 4311320). Samples were run on an Applied Biosystems 3130 sequencer. The arrows shown in FIGS. 25A-25D indicate the expected peak determined by a separate experiment (results not shown) in which the mobilities of synthetic dye-labeled oligos of the sequences shown were established. Each of FIGS. 25A-25D presents additional sequence information concerning the complement of the single-stranded portion of the template provided. It can be seen in FIG. 25D that the full-sequence of the complement of the single stranded portion of the template has been obtained.

Example 2—Cycle Sequencing

An approach to cycle sequencing comprised making an equimolar mixture of targets comprising primer sequences on each end. Target sequences were diluted to a concentration of a single molecule per aqueous immiscible-fluid-discrete-volume and the aqueous immiscible-fluid-discrete-volumes, spaced-apart from one another by an immiscible spacing fluid and comprising single molecules, were flowed into a conduit. Single molecules were amplified by PCR in the conduit to form amplicons. The amplicons were then dispensed into a multiwell tray. Shrimp alkaline phosphatase (SAP) and exonuclease were added to each immiscible-fluid-discrete-volume, followed by heat treatment to kill enzymatic activity. Dye terminator reagents were added to each immiscible-fluid-discrete-volume and cycle sequencing was performed. Sequencing reaction products were precipitated and further analyzed. Other approaches can also be used.

A sequencing experiment was performed using six target sequences (SEQ ID NOS. 3-8). The experiment comprised a) preparing an aqueous immiscible-fluid-discrete-volume comprising target sequences (SEQ ID NOS. 3-8) and primers (SEQ ID NOS. 1-2), b) loading immiscible-fluid-discrete-volumes comprising the target sequences and primer, along with spacing fluid, into a conduit, 3) amplifying the target sequences, and 4) sequencing the amplicons obtained from amplification of target sequences.

TABLE 1

Sequences Used in Sequencing Experiment
DNA sequences (from the 5' end):

HB fwd primer
HB rev primer
Target T1
Target T2
Target T3
Target T4
Target T5
Target T6

A 1-mL disposable syringe containing 200 µL of a solution consisting of 2×SYBR green master mix (Applied Biosystems Product. No. 4309159, 100 µL), HB fwd primer (0.2 mM), HB rev primer: (0.2 mM), BSA (0.048%), an equimolar mixture of targets T1-T6 (2000 copies total), and water was placed in a Sage syringe pump model 351. SYBR green master mix contains a DNA intercalating dye-SYBR green that, upon binding to double stranded DNA generated during PCR amplification, can show enhanced fluorescence at 520 nm emission. A second dye in the mix, ROX, was used as a fluorescence reference at 620 nm emission.

A second 1-mL disposable syringe containing 0.3 mL polydimethylsiloxane oil having a viscosity of 5 centistokes (Sigma Aldrich Product No. 317667) was placed in the syringe pump. The syringes were connected to the two arms of a "T" fitting (Upchurch Product No. P-714) via polytetrafluoroethylene tubing (Upchurch Product No. 1907, O.D.=1/16", I.D.=0.02") and PEEK flangeless fittings (Upchurch Product No. P-136 (nut), P-200x (ferrule), P-631 (union), P-624 (luer)).

To the stem of the "T" fitting was attached a 25 cm length of polytetrafluoroethylene tubing. The two fluids were simultaneously injected into the "T" fitting, resulting in immiscible-fluid-discrete-volumes spaced-apart from one another by spacing fluid, to form 14 total immiscible-fluid-discrete-volumes per centimeter. The ends of the tubing were capped using a nut, ferrule, union, and plug (Upchurch P-316).

The tubing was looped once and pressed into two grooves of a 75×85 mm aluminum plate. The plate had grooves spaced at 3.2 mm to snugly hold the tubing. The plate was clamped onto an Applied Biosystem 9700 thermal cycler, mounted on a X-Y stage under LabVIEW (National Instruments) software control.

The plate was heated for 120 seconds at 51° C., 630 seconds at 97.2° C., followed by 50 cycles of 30 seconds at 97.2° C. and 77 seconds at 61.2° C. Fifty millimeters of the tubing was scanned once during each cycle at 61.2° C. via an argon ion laser. The laser light was focused with a 10× microscope objective with a numerical aperture of 0.3. The fluorescence signal that returned through the microscope objective was filtered through a long pass filter transmitting light at 500 nm and higher.

A dichroic filter reflected light between 500-575 nm to a first photomultiplier tube (PMT). Light above 575 nm was transmitted to a second PMT. The ratio of the first and second PMT signals at each cycle was recorded as an amplification curve. The final scan after 50 cycles of 50 mm of the tubing (out of the 14 cm that had been thermally cycled) indicated that approximately 13 out of 31 aqueous immiscible-fluid-discrete-volumes showed significantly more signal than the segments at the start, which was considered evidence of amplification. Each immiscible-fluid-discrete-volume was calculated to have a volume of 140 nL containing an initial concentration of 1.4 targets/immiscible-fluid-discrete-volume.

After thermal cycling, one end of the tubing was connected to a syringe pump and the other end held by a mechanical arm with X-Y-Z control over a 384-well plate. Each well of the plate held 5 µL of water. The aqueous immiscible-fluid-discrete-volumes were distinguished from the oil by their fluorescence by viewing with blue LED excitation through a 540 nm long pass filter. When an aqueous immiscible-fluid-discrete-volume reached the end of the tubing, the mechanical arm was lowered into a well of the 384-well plate below the top surface of the plate, effectively removing the immiscible-fluid-discrete-volume from the tip of the tubing.

All the immiscible-fluid-discrete-volumes were dispensed in this manner, without attempting to distinguish positive immiscible-fluid-discrete-volumes (containing amplicon) from negative ones. Approximately 96 wells were filled with immiscible-fluid-discrete-volumes.

To each well was added 1 µL of buffer (Tris, 50 mM, pH 6.8) containing shrimp alkaline phosphatase (0.3 units) and exonuclease I (6 units). After incubating at 37° C. for 30 minutes, the temperature was raised to 80° C., for 15 minutes, to heat-kill the enzymes. To each well was added BigDye™ v.3.1 (Applied Biosystems Product No. 4337454) terminator reaction solution (2 µL), 5× sequencing buffer (3 µL), HB fwd primer (1 µL of 5 µM), and water (8 µL). The plate was placed in an Applied Biosystems 9700 thermal cycler and subjected to the following thermal cycle: 60 seconds at 96° C., followed by 50 cycles of 10 seconds at 96° C., 5 seconds at 50° C., and 4 minutes at 60° C.

The samples, now at 20 µL, were pipetted into a 96-well plate. To each well was added 5 µL EDTA (125 mM) and ethanol (60 µL). After incubating at room temperature for 15 minutes, the plate was centrifuged on a SORVALL RC SC Plus centrifuge with Rotor 29 at 4000 rpm for 30 minutes at 4° C. The ethanol was removed, the samples washed with 70-30 ethanol-water, dried, and resuspended in 20 µL of deionized water. The samples were run on an Applied Biosystems 3130xl capillary electrophoretic sequencer with 36 cm capillaries filled with POP7 polymer (Applied Biosystems). Injection was at 2.4 kv for 150 seconds.

Figure 26A:
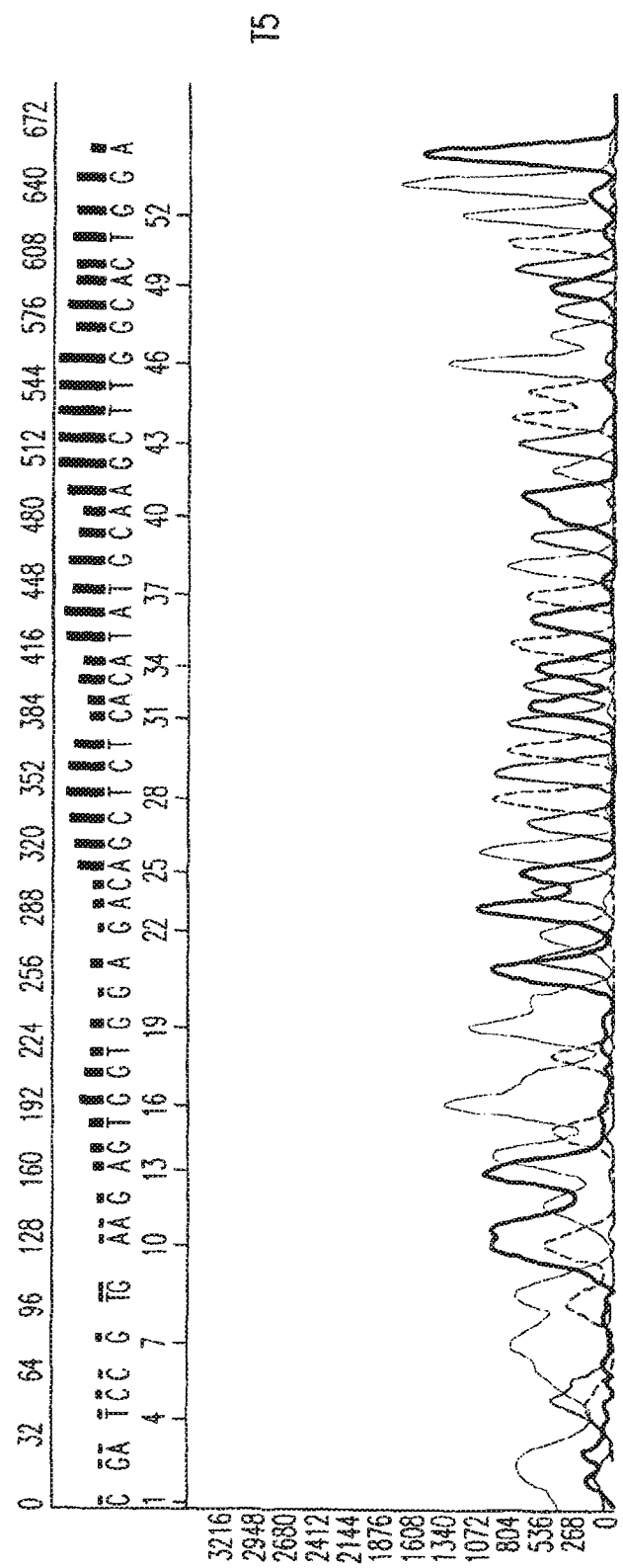
FIGS. 26A-26C illustrates representative results obtained from a cycle-sequencing experiment.
Figure 26B:
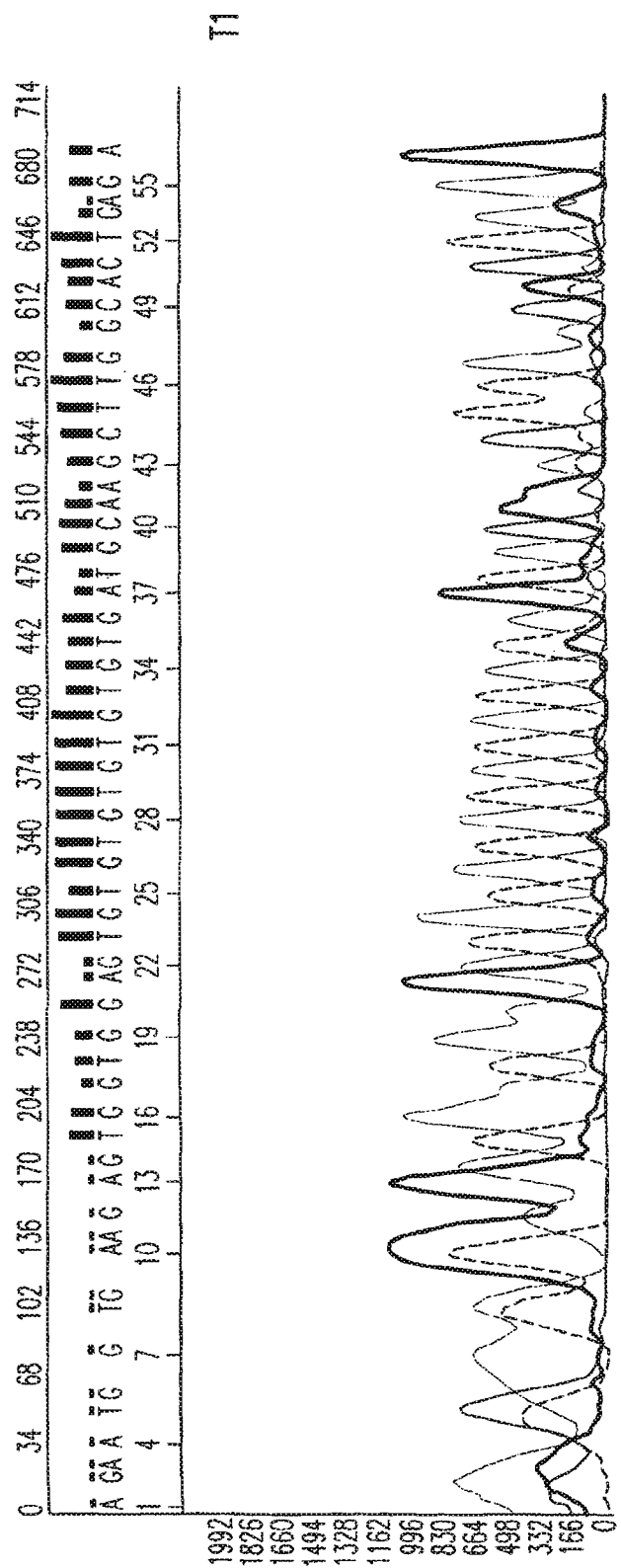
Figure 26C:
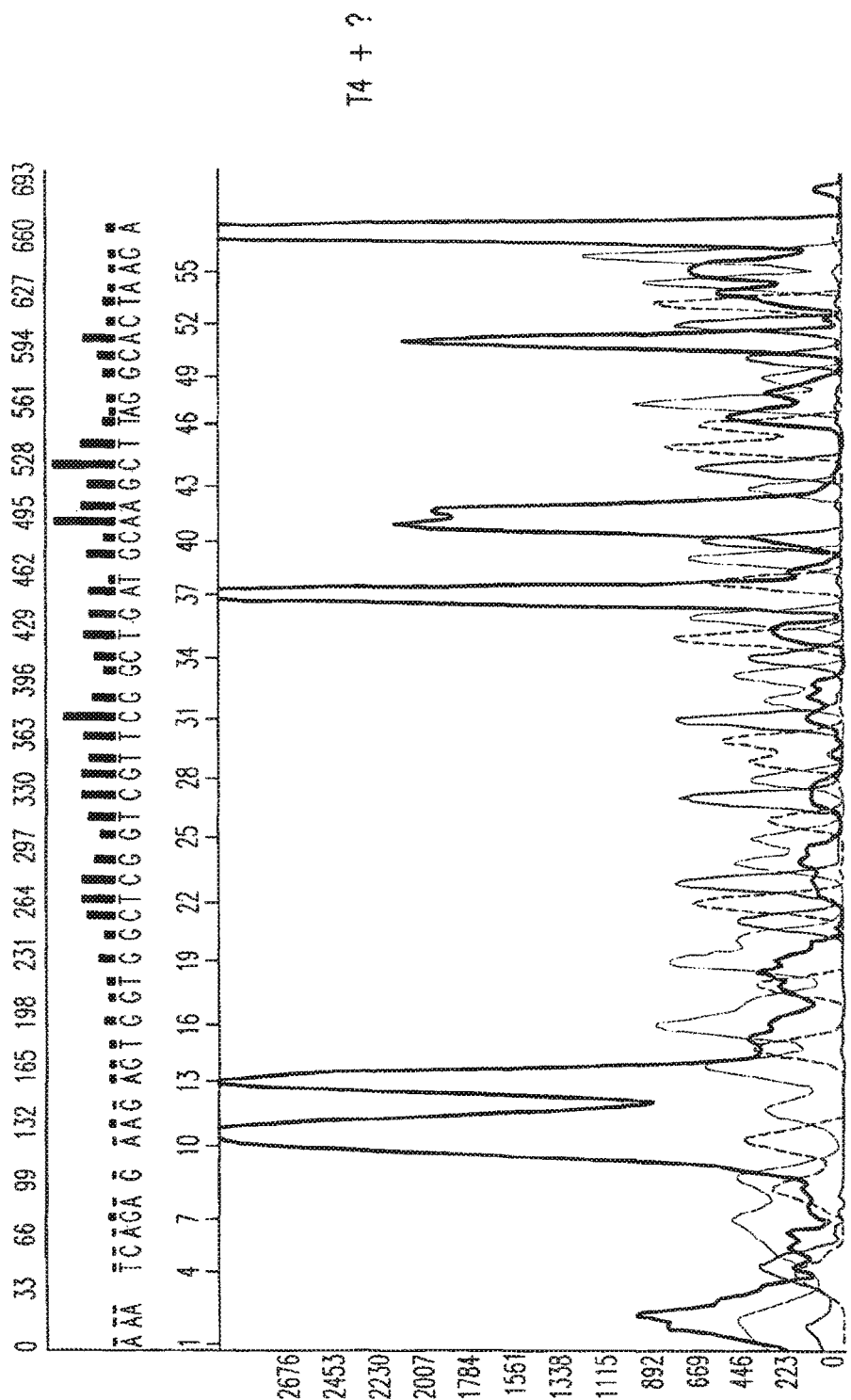

Representative results of the experiment are shown in FIGS. 26A-26C which illustrate electropherograms of sequenced immiscible-fluid-discrete-volumes. The assignment of the targets (for example, T1, T2, T3, etc.) is shown on the right in each figure. FIGS. 26A and 26B show sequencing results for targets T5 and T1, respectively. One of the electropherograms, FIG. 26C, shows multiple products—T4—and an undetermined target sequence. The results demonstrate the feasibility of sequencing single target molecules in multiple aqueous immiscible-fluid-discrete-volumes having a calculated concentration of 1.4 targets per 40 nl immiscible-fluid-discrete-volume.

Example 3—Fiducial Markers

According to various embodiments, two fluorescent dyes can be used as a reporter molecule in fluid volumes: Cy3 and Cy5. The level of distinguishable signals received from Cy3 and Cy5 are 3 and 2, respectively. For each volume, the number of possible signals generated is 3×2=6. If three fluid volumes are used as a fiducial marking, the total number of permutations is $(6)^3=216$. If each fiducial marker is used as a reference to identify a group of 40 fluid volumes, the number of samples that can be tracked is 216×40=8,640 samples. In this example, the number of reporter samples is 3×2=6, composed of the possible combinations of the two dyes with different signal levels. These examples assume the use of dummy volumes to generate fiducial markers. The 6-reporter configurations can generate 216 permutations for a 3-volume fiducial marker system. According to various embodiments, a combination of different sample tracing methods enables a larger sample tracking capability. For example, the simultaneous implementation of fluorescent dyes along with use of the length of fluid volumes to define fiducial markers provides an extra dimension or parameter to generate a higher number of permutations. According to various embodiments, the length of spacing fluid can be utilized as a parameter combined with other tracing variables.

Example 4—Fiducial Markers

Similar to Example 3, two fluorescent dyes can be used as a set of distinct reporter markers in fiducial volumes: Cy3 and Cy5. The level of distinguishable signals from Cy3 and Cy5 are 3 and 2, respectively. For each fluid volume, two defined lengths of the fluid volume can be utilized. For each fluid volume, the number of possible permutations is therefore 3×2×2=12. If three fluid volumes are used as variables to generate a fiduciary marker, the number of possible permutations is $(12)^3=1,728$. If two fluid volumes are used instead, $(12)^2=144$ permutations are possible for the resulting fiduciary markers.

Example 5—Fiducial Markers

According to various embodiments of the present teachings, in an application for generation of immiscible-fluid-discrete-volumes where volumes are generated by bringing together a stream of spacing fluid and a stream of aqueous liquid, the content of each aqueous fluid volume is essentially the same. In this case, generation of fiducial markers is not the same as the case of fluid volumes that are generated with flexible or selectable content. In applications such as these, the use of an activatable reporter molecule can offer the flexibility to generate fiducial markers on-the-fly, and alter those marker assignments during processing as desired.

According to various embodiments, various applications using immiscible-fluid-discrete-volumes require individual sample tracking of the content of the fluid volumes, including DNA resequencing applications, such as Variant$^{SEQ}$ (available from Applied Biosystems Inc., Foster City, Calif.), in which the content of individual fluid volumes needs to be traced to or associated with the sequencing information. In each fluid volume, the primer sets and genomic template that are present must be tracked to map the sequencing data. In a scenario where many genomic DNA samples are subjected to the same group of primer sets, it must be known where the start and end of each group of primer sets are located, and which genomic DNA is added to each group of fluid volumes. Sample tracking techniques as described herein enable fluid volume identification for these applications. In further applications of genotyping and real-time polymerase chain reaction (PCR) for gene expression, among others, the content of individual fluid volumes needs to be traceable as well. Similar to resequencing applications, the identification of which DNA template goes into which fluid volume needs to be traceable for these applications as well. According to embodiments of the present teachings in a further regard, a further advantage of sample tracing capability as disclosed herein is an ability to trace fluid volumes that undergo volume splitting. In de novo and resequencing (Variant SEQ™) applications, for example, it is desired to collect both the forward and reverse sequence information from the same template. The technique of fluid volume splitting by passing the volumes through a tee into two streams conserves the fiducial markers, which allows sample tracking after the volumes are split.

Example 6—Zip Codes

Step 1: Multiplex ligation reactions: 256 zip coded ligation probes, universal forward primers (FP), and 256 universal reverse primers (RP), were ligated together in the presence of cDNA, or other nucleic acid sample to be reacted with T4 DNA ligase to form a maximum of 65536 possible ligation products that have 8 oligonucleotides of a uniquely determined sequence. The 3' ends of the Zip-RPs were blocked by an NH2 group to prevent spurious ligation and to prevent primer extension in later steps. The NH2 group was chosen for convenience of oligomer synthesis. Other modifications to the 3' end that achieve the same purpose can be used, for example, a 3' dideoxy modification. The Zip-RPs underwent a kinase reaction to add a phosphate group to the Zip-RPs 5' ends. Then T4 DNA ligase connected the Zip-FPs and the Zip-RPs to the amplified target sequences. Primers are synthesized with target specific regions, or alternatively with target specific regions, and zip coded tails.

Step 2, Pre-PCR: 256 Zip-RPs, that were complementary to the sequences on the Zip-RP probes, were used as were primers that have the same sequences as the Zip-RP probes, to amplify ligation products 65536-fold (16 cycles), to allow the following sample splitting for readout PCR. Amplification reaction will occur as a result of target specific primers; this can be either done in a batch lot as a pre-amplification with primers that have target specific tails, followed by amplification using zipcode primers in individual slugs, or by amplifying directly using target specific primers. In either case, the primers used in the individual slugs need to have additional universal tails, so that the forward and reverse sequencing reactions do not need individually matched primers for each slug.

PCR readout: The abundance of each particular 8 nucleotide sequence was measured by SYBR Green detection in a single-plex reaction with the corresponding Zip-RPs and Zip-FPs. In the case of 256 FPs and 256 RPs, this corresponded to 65536 PCR reactions (256×256).

Alternative PCR readout: Primers Zip-FP1 through Zip-FP256 were placed in a first sample withdrawing conduit to generate 256 immiscible-fluid-discrete-volumes. To each immiscible-fluid-discrete-volume was added Zip-RP256 from a second plate. After suitable reagents had been added to all 256 immiscible-fluid-discrete-volumes, the second sample withdrawing conduit indexed to Zip-RP258 so that it could add this primer to the next round of 256 immiscible-fluid-discrete-volumes generated from the first sample withdrawing conduit. The process was repeated until all 65536 combinations were generated. Downstream, the pre-amplified ligation product was added at a T-junction to each immiscible-fluid-discrete-volume. The immiscible-fluid-discrete-volumes were subjected to thermal cycling and SYBR green detection to quantitate the amount of each 8 nucleotide sequence present in the original sample. Quantitation was conducted by both real-time PCR and by an end point reading with SYBR green. For end point readings, long-linear conversion was used because RP-zip has limited concentration, for example, 20-50 NM, while FP-zip has a 1 uM concentration.

Other embodiments of the present teachings will be apparent to those skilled in the art from consideration of the present specification and practice of the present teachings disclosed herein. It is intended that the specification and examples be considered as exemplary only and not be limiting of the claims. All cited references, patents, and patent applications are incorporated in their entireties herein by reference.

What is claimed is:

1. A method comprising:
within a first conduit having a circular cross section having a maximum dimension, flowing a sample including a first plurality of aqueous droplets comprising a single molecule of a target nucleic acid sequence and a second plurality of aqueous droplets containing no molecules of the target nucleic acid sequence, the aqueous droplets being separated within the conduit by an immiscible fluid that is immiscible with the aqueous droplets, the aqueous droplets having a maximum dimension that is less than the maximum dimension of the first conduit;
amplifying the target nucleic acid sequence in each of the first plurality of aqueous droplets to form an amplicon;
while flowing the aqueous droplets within a second conduit, using a fluorescent signal detector to detect and identify the first plurality of aqueous droplets by detecting fluorescence from the first plurality of aqueous droplets.

2. A method comprising:
sequentially contacting an aqueous sample fluid in a conduit with a non-aqueous spacing fluid that is immiscible with the aqueous sample fluid, to form discrete volumes of the aqueous sample fluid separated from one another by the non-aqueous spacing fluid, the aqueous sample fluid comprising a target nucleic acid sequence, wherein a first plurality of the discrete volumes contains at least one molecule of the target nucleic acid sequence and a second plurality of the discrete volumes contains no molecules of the target nucleic acid sequence;
amplifying the target nucleic acid sequence in one or more of the first plurality of discrete volumes to form an amplicon; and
in a second conduit, detecting a fluorescence signal from the amplicon in each of the one or more first plurality of discrete volumes; and
based on the detecting, discriminating between the first plurality of discrete volumes and the second plurality of discrete volumes.

3. The method of claim 2, wherein the contacting comprises continuously flowing at least one of the aqueous sample fluid and the non-aqueous spacing fluid into the conduit.

4. The method of claim 2, further comprising sorting the second plurality of discrete volumes from the first plurality of discrete volumes.

5. The method of claim 2, wherein less than 37% of the discrete volumes comprise a single molecule of the target nucleic acid sequence.

6. The method of claim 5, wherein 1% or more of the discrete volumes comprise a single molecule of the target nucleic acid sequence.

7. The method of claim 5, wherein 10% or more of the discrete volumes comprise a single molecule of the target nucleic acid sequence.

8. The method of claim 1, wherein less than 37% of aqueous droplets comprise a single molecule of the target nucleic acid sequence.

9. The method of claim 8, wherein 1% or more of aqueous droplets comprise a single molecule of the target nucleic acid sequence.

10. The method of claim 8, wherein 10% or more of aqueous droplets comprise a single molecule of the target nucleic acid sequence.

11. The method of claim 1, wherein the aqueous droplets and the immiscible fluid form a plurality of emulsified droplets, the method further comprising:

dispensing emulsified droplets from an end of the conduit and into one or more containers; and thermal cycling the container and the emulsified droplets in a thermal cycler.

12. The method of claim 11, wherein the containers comprises wells of a multiwell plate.

13. The method of claim 11, wherein at least some of the emulsified droplets have a volume that is less than about 50 nanoliters.

14. The method of claim 11, wherein at least some of the emulsified droplets have a volume of between about 1 femtoliter and 1 nanoliter.

15. The method of claim 11, further comprising, for at least some of the first plurality of aqueous droplets, detecting with a detector the amplicon or a derivative thereof in a second conduit.

16. The method of claim 11, wherein the detector is a fluorescent signal detector.

17. The method of claim 11, further comprising, after thermal cycling in the thermal cycler, running the sample through a capillary.

18. The method of claim 11, further comprising, after thermal cycling in the thermal cycler, running the sample through on a capillary electrophoretic sequencer.

* * * * *